United States Patent
Stump et al.

(10) Patent No.: US 8,148,390 B2
(45) Date of Patent: Apr. 3, 2012

(54) MONOCYCLIC ANILIDE SPIROLACTAM CGRP RECEPTOR ANTAGONISTS

(75) Inventors: Craig A. Stump, Pottstown, PA (US);
Ian M. Bell, Harleysville, PA (US);
Harold G. Selnick, Ambler, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 138 days.

(21) Appl. No.: 12/530,898

(22) PCT Filed: Mar. 7, 2008

(86) PCT No.: PCT/US2008/003078
§ 371 (c)(1),
(2), (4) Date: Feb. 9, 2010

(87) PCT Pub. No.: WO2008/112159
PCT Pub. Date: Sep. 18, 2008

(65) Prior Publication Data
US 2010/0152216 A1    Jun. 17, 2010

Related U.S. Application Data

(60) Provisional application No. 60/906,399, filed on Mar. 12, 2007.

(51) Int. Cl.
*A61K 31/513* (2006.01)
*A61K 31/4184* (2006.01)
*A61K 31/437* (2006.01)
*A61P 25/06* (2006.01)
*C07D 403/12* (2006.01)
*C07D 471/10* (2006.01)
*C07D 491/107* (2006.01)
*C07D 471/20* (2006.01)

(52) U.S. Cl. ........ 514/274; 514/389; 514/278; 544/230; 546/15; 548/301.1

(58) Field of Classification Search .................. None
See application file for complete search history.

(56) References Cited

U.S. PATENT DOCUMENTS

| | | | |
|---|---|---|---|
| 7,192,954 B2 | 3/2007 | Bell et al. | |
| 7,625,901 B2 | 12/2009 | Wood et al. | |
| 7,629,338 B2 | 12/2009 | Wood et al. | |
| 7,659,300 B2 | 2/2010 | Bell et al. | |
| 2010/0056498 A1 | 3/2010 | Wood et al. | |

FOREIGN PATENT DOCUMENTS

| | | |
|---|---|---|
| WO | 2004082605 A2 | 9/2004 |
| WO | WO 2004083187 | 9/2004 |
| WO | 2006031610 A2 | 3/2006 |
| WO | WO 2007133491 | 11/2007 |
| WO | WO2008020902 | 2/2008 |

OTHER PUBLICATIONS

Tepper et al., Headache, (Sep. 2008), p. 1259-1268.*
Supplementary European Search Report and Search Opinion for counterpart European patent application No. EP 08 72 6587, (2011).

* cited by examiner

*Primary Examiner* — Yong Chu
(74) *Attorney, Agent, or Firm* — Nicole M. Beeler; Gerard M. Devlin

(57) ABSTRACT

The present invention is directed to compounds of Formula I:

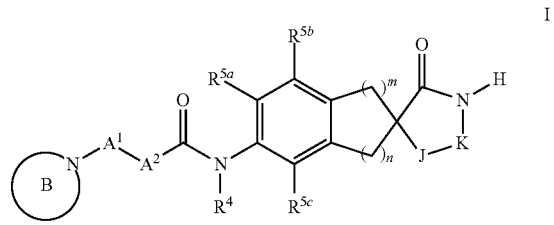

(where variables $A^1$, $A^2$, B, J, K, m, n, $R^4$, $R^{5a}$, $R^{5b}$ and $R^{5c}$ are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

19 Claims, No Drawings

MONOCYCLIC ANILIDE SPIROLACTAM CGRP RECEPTOR ANTAGONISTS

CROSS-REFERENCE TO RELATED APPLICATIONS

This application claims priority under 35 U.S.C. §119(e) of U.S. provisional application Ser. No. 60/906,399, filed Mar. 12, 2007.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human $\alpha$-CGRP-(8-37), a fragment of CGRP that lacks seven N-terminal amino acid residues, is a selective antagonist of $CGRP_1$, whereas the linear analogue of CGRP, diacetamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extracranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

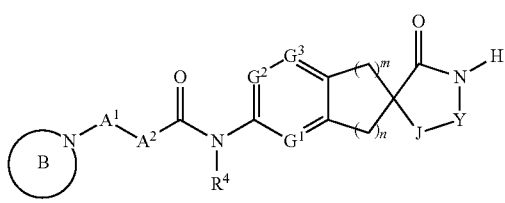

wherein:
B is a heterocycle selected from the group consisting of:

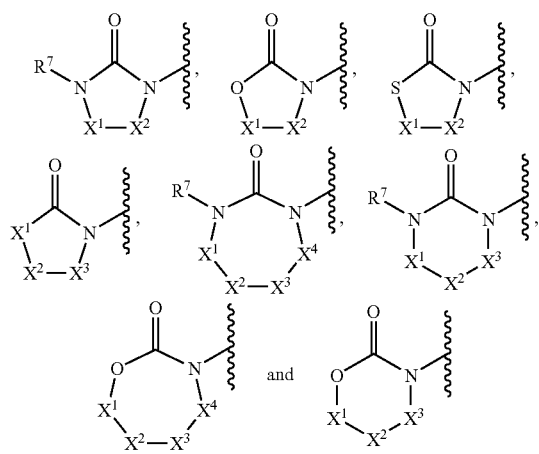

wherein $X^1$, $X^2$, $X^3$ and $X^4$ are each carbon, and one of $X^1$, $X^2$, $X^3$ and $X^4$ present on B is spirally substituted to form a ring or ring system selected from:
 indanyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, 2,3,4,5-tetrahydro-1-benzoxepinyl, 2,3,4,5-tetrahydro-1H-1-benzazepinyl, 2,3,4,5-tetrahydro-1-benzothiepinyl, 1,3,4,5-tetrahydro-2-benzoxepinyl, 2,3,4,5-tetrahydro-1H-2-benzazepinyl, 1,3,4,5-tetrahydro-2-benzothiepinyl, 1,2,4,5-tetrahydro-3-benzoxepinyl, 2,3,4,5-tetrahydro-1H-3-benzazepinyl, 1,2,4,5-tetrahydro-3-benzothiepinyl, cycloheptyl, morpholinyl, tetrahydropyranyl, tetrahydrofuranyl, thiepanyl, oxepanyl and azepanyl,
which ring or ring system is unsubstituted or substituted with one or more substituents each independently selected from:
 (a) —$C_{1-6}$alkyl, which is unsubstituted or substituted with 1-3 substituents where the substituents are independently selected from: halo, hydroxy, —$OC_{1-6}$alkyl, —$C_{3-6}$cycloalkyl, —$CO_2R^9$, —$NR^{10}R^{11}$, —$SO_2R^{12}$, —$CONR^{10a}R^{11a}$, phenyl and heterocycle, wherein said heterocycle is selected from: pyridyl, pyrimidinyl, pyrazinyl, pyridazinyl, piperidinyl, piperazinyl, pyrrolidinyl, thienyl, and morpholinyl,
 (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{3-6}$cycloalkyl, —$C_{1-6}$alkyl which is unsubstituted or substituted with 1-6 fluoro, and —$OC_{1-6}$alkyl which is unsubstituted or substituted with 1-6 fluoro, halo, or hydroxyl,
 (c) —$SO_2R^{12}$,
 (d) hydroxy,
 (e) —$OC_{1-6}$alkyl, which is unsubstituted or substituted with 1-5 halo,
 (f) —$COR^{12}$,
 (g) —$NR^{10}R^{11}$,
 (h) halo,
 (i) —CN,
 (j) —$CONR^{10a}R^{11a}$, and
 (k) oxo,
 (l) —$C_{3-6}$cycloalkyl,
and wherein the remaining members of the group $X^1$, $X^2$, $X^3$ and $X^4$ present on B are each independently unsubstituted or substituted with one or two substituents selected from $R^1$ and $R^2$, where:
 $R^1$ and $R^2$ are each independently selected from:
 (1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
  (f) —$CO_2R^9$, and
  (g) —$CONR^{10a}R^{11a}$,
 (2) —$C_{3-6}$cycloalkyl, which is unsubstituted or substituted with 1-7 substituents each independently selected from: halo, hydroxy, —$OC_{1-6}$alkyl, trifluoromethyl and phenyl,
 (3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
  (a) —$C_{1-6}$alkyl, which is unsubstituted or substituted with 1-6 fluoro, (b) halo,
(c) hydroxy,
(d) —$OC_{1-6}$alkyl, which is unsubstituted or substituted with 1-6 fluoro,
(e) —$C_{3-6}$cycloalkyl,
(f) phenyl which is unsubstituted or substituted with 1-5 substituents each independently selected from: —$C_{1-6}$ alkyl, —O—$C_{1-6}$alkyl, halo, hydroxyl and trifluoromethyl,
(g) —$CO_2R^9$,
(h) —$NR^{10}R^{11}$,
(i) —$CONR^{10a}R^{11a}$, and
(j) —$SO_2R^{12}$,
(4) halo,
(5) hydroxy,
(6) —$OC_{1-6}$alkyl, which is unsubstituted or substituted with 1-5 halo,
(7) —CN,
(8) —$CO_2R^9$,
(9) —$NR^{10}R^{11}$,
(10) —$SO_2R^{12}$, and
(11) —$CONR^{10a}R^{11a}$;
or, wherein $X^1$, $X^2$, $X^3$ and $X^4$ are each carbon, and one of $X^1$, $X^2$, $X^3$ and $X^4$ present on B is —(C=O)—,
wherein another one or two of the members of the group $X^1$, $X^2$, $X^3$ and $X^4$ present on B is optionally spirally substituted to form a ring or ring system selected from:

cyclopropyl, cyclobutyl, cyclopentyl, cyclohexyl, cycloheptyl, cyclooctyl, indanyl, azetidinyl, pyrrolidinyl, piperidinyl, piperazinyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, 2,3,4,5-tetrahydro-1-benzoxepinyl, 2,3,4,5-tetrahydro-1H-1-benzazepinyl, 2,3,4,5-tetrahydro-1-benzothiepinyl, 1,3,4,5-tetrahydro-2-benzoxepinyl, 2,3,4,5-tetrahydro-1H-2-benzazepinyl, 1,3,4,5-tetrahydro-2-benzothiepinyl, 1,2,4,5-tetrahydro-3-benzoxepinyl, 2,3,4,5-tetrahydro-1H-3-benzazepinyl, 1,2,4,5-tetrahydro-3-benzothiepinyl, morpholinyl, tetrahydropyranyl, tetrahydrofuranyl, thiepanyl, oxepanyl and azepanyl, which ring is unsubstituted or substituted with one or more substituents each independently selected from:
(a) —$C_{1-6}$alkyl, which is unsubstituted or substituted with 1-3 substituents where the substituents are independently selected from: halo, hydroxy, —$OC_{1-6}$alkyl, —$C_{3-6}$cycloalkyl, —$CO_2R^9$, —$NR^{10}R^{11}$, —$SO_2R^{12}$, —$CONR^{10a}R^{11a}$ phenyl and heterocycle, wherein said heterocycle is selected from: pyridyl, pyrimidinyl, pyrazinyl, pyridazinyl, piperidinyl, piperazinyl, pyrrolidinyl, thienyl, and morpholinyl,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{3-6}$cycloalkyl, —$C_{1-6}$alkyl which is unsubstituted or substituted with 1-6 fluoro, and —$OC_{1-6}$alkyl which is unsubstituted or substituted with 1-6 fluoro, halo, or hydroxyl,
(c) —$SO_2R^{12}$,
(d) hydroxy,
(e) —$OC_{1-6}$alkyl, which is unsubstituted or substituted with 1-5 halo,
(f) —$COR^{12}$,
(g) —$NR^{10}R^{11}$,
(h) halo,
(i) —CN,
(j) —$CONR^{10a}R^{11a}$,
(k) oxo,
(l) —$C_{3-6}$cycloalkyl, and wherein the remaining members of the group $X^1$, $X^2$, $X^3$ and $X^4$ present on B are each independently unsubstituted or substituted with one or more substituents selected from $R^1$ and $R^2$, where $R^1$ and $R^2$ are independently selected from:
(1) —$C_{1-6}$alkyl, which is unsubstituted or substituted with 1-7 substituents each independently selected from:
(a) halo,
(b) hydroxy,
(c) —$OC_{1-6}$alkyl,
(d) —$C_{3-6}$cycloalkyl,
(e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl and —$OCF_3$,
(f) —$CO_2R^9$, and
(g) —$CONR^{10a}R^{11a}$;
(2) —$C_{3-6}$cycloalkyl, which is unsubstituted or substituted with 1-7 substituents each independently selected from: halo, hydroxy, —$OC_{1-6}$alkyl, trifluoromethyl and phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
(a) —$C_{1-6}$alkyl, which is unsubstituted or substituted with 1-6 fluoro,
(b) halo,
(c) hydroxy,
(d) —$OC_{1-6}$alkyl, which is unsubstituted or substituted with 1-6 fluoro,
(e) —$C_{3-6}$cycloalkyl,
(f) phenyl which is unsubstituted or substituted with 1-5 substituents each independently selected from: —$C_{1-6}$ alkyl, —$OC_{1-6}$alkyl, halo, hydroxyl and trifluoromethyl,
(g) —$CO_2R^9$,
(h) —$NR^{10}R^{11}$,
(i) —$CONR^{10a}R^{11a}$, and
(j) —$SO_2R^{12}$,
(4) halo,
(5) hydroxy,
(6) —$OC_{1-6}$alkyl, which is unsubstituted or substituted with 1-5 halo,
(7) —CN,
(8) —$CO_2R^9$,
(9) —$NR^{10}R^{11}$,
(10) —$SO_2R^{12}$, and
(11) —$CONR^{10a}R^{11a}$;

$A^1$ and $A^2$ are each independently selected from:
(1) a bond, and
(2) —$CR^{13}R^{14}$—,
wherein one of $A^1$ and $A^2$ is optionally absent;
$G^1$, $G^2$, and $G^3$ are each independently selected from:

(1) —C($R^5$)=,
(2) —N=, and
(3) —($N^+$—$O^-$)=;

J is independently selected from:
(1) =C($R^{6a}$)—,
(2) —$CR^{13}R^{14}$—,
(3) —N($R^{15}$)—, and
(4) —C(=O)—;

Y is independently selected from:
(1) =C($R^{6b}$)—,
(2) —$CR^{13}R^{14}$—,
(3) —C(=O)—,
(4) —$SO_2$—,
(5) =N—, and
(6) —N($R^{6b}$)—;

$R^4$ is selected from:
(1) hydrogen,
(2) —$C_{1-6}$alkyl, which is unsubstituted or substituted with 1-5 substituents each independently selected from:
 (a) halo,
 (b) —$C_{3-6}$cycloalkyl,
 (c) —$CF_3$, and
 (d) —$OC_{1-6}$alkyl, which is unsubstituted or substituted with 1-5 halo,
(3) —$C_{3-6}$cycloalkyl,
(4) benzyl, and
(5) phenyl;

$R^5$ is selected from:
(1) hydrogen,
(2) —$C_{1-6}$alkyl, which is unsubstituted or substituted with 1-7 substituents each independently selected from:
 (a) halo,
 (b) hydroxy,
 (c) —$OC_{1-6}$alkyl,
 (d) —$C_{3-6}$cycloalkyl,
 (e) phenyl,
 (f) —$CONR^{10a}R^{11a}$,
 (g) —$CO_2R^9$, and
 (h) —$NR^{10}R^{11}$,
(3) —$C_{3-6}$cycloalkyl,
(4) phenyl, which is unsubstituted or substituted with 1-3 substituents each independently selected from:
 (a) —$C_{1-4}$alkyl, which is unsubstituted or substituted with 1-3 fluoro,
 (b) halo,
 (c) hydroxy, and
 (d) —O—$C_{1-6}$alkyl, which is unsubstituted or substituted with 1-6 fluoro,
(5) halo,
(6) hydroxy,
(7) —$OC_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$, and
(14) —($NR^{10a}$)$CO_2R^9$;

$R^{6a}$ and $R^{6b}$ are each independently selected from:
(1) hydrogen;
(2) —$C_{1-4}$alkyl, which is unsubstituted or substituted with 1-5 substituents each independently selected from:
 (a) halo,
 (b) —O—$C_{1-6}$alkyl,
 (c) —$C_{3-6}$cycloalkyl, and
 (d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$,
(3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from:
 (a) —$C_{1-4}$alkyl which is unsubstituted or substituted with 1-5 fluoro,
 (b) halo,
 (c) hydroxy,
 (d) —O—$C_{1-4}$alkyl which is unsubstituted or substituted with 1-5 fluoro,
 (e) —$C_{3-6}$cycloalkyl, and
 (f) phenyl,
(4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$;

or where $R^{6a}$ and $R^{6b}$ and the atom(s) to which they are attached are joined to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
 (a) —$C_{1-6}$alkyl which is unsubstituted or substituted with 1-3 substituents each independently selected from:
  (i) halo,
  (ii) hydroxy,
  (iii) —O—$_{1-6}$alkyl,
  (iv) —$C_{3-6}$cycloalkyl,
  (v) phenyl or heterocycle, wherein heterocycle is selected from: pyridyl, pyrimidinyl, pyrazinyl, pyridazinyl, piperidinyl, piperazinyl, pyrrolidinyl, thienyl, or morpholinyl, which phenyl or heterocycle is unsubstituted or substituted with 1-5 substituents each independently selected from: —$C_{1-6}$ alkyl, —O—$C_{1-6}$alkyl, halo, hydroxy, trifluoromethyl and —$OCF_3$,
  (vi) —$CO_2R^9$,
  (vii) —$NR^{10}R^{11}$,
  (viii) —$SO_2R^{12}$,
  (ix) —$CONR^{10a}R^{11a}$, and
  (x) —($NR^{10a}$)$CO_2R^9$,
 (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents are each independently selected from: —$C_{1-6}$alkyl which is unsubstituted or substituted with 1-6 fluoro, halo, hydroxy, —O—$C_{1-6}$ alkyl, which is unsubstituted or substituted with 1-6 fluoro and —$C_{3-6}$cycloalkyl, (c) halo,
(d) —SO$_2$R$^{12}$,
(e) hydroxy,
(f) —O—C$_{1-6}$alkyl, which is unsubstituted or substituted with 1-5 halo,
(g) —CN,
(h) —COR$^{12}$,
(i) —NR$^{10}$R$^{11}$,
(j) —CONR$^{10a}$R$^{11a}$,
(k) —CO$_2$R$^9$,
(l) —(NR$^{10a}$)CO$_2$R$^9$,
(m) —O(CO)NR$^{10a}$R$^{11a}$,
(n) —(NR$^9$)(CO)NR$^{10a}$R$^{11a}$, and
(O) oxo;

R$^7$ is selected from:
(1) hydrogen;
(2) —C$_{1-4}$alkyl, which is unsubstituted or substituted with 1-5 substituents where the substituents are each independently selected from:
  (a) halo,
  (b) —OC$_{1-6}$alkyl,
  (c) —C$_{3-6}$cycloalkyl,
  (d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from: —CN, C$_{1-6}$alkyl, —OC$_{1-6}$alkyl, halo, hydroxy, trifluoromethyl and —OCF$_3$,
  (e) —COR$^{12}$,
  (f) —NR$^{10}$R$^{11}$,
  (g) —CONR$^{10a}$R$^{11a}$,
  (h) —CO$_2$R$^9$,
  (i) —(NR$^{10a}$)CO$_2$R$^9$,
  (j) —O(CO)NR$^{10a}$R$^{11a}$,
  (k) —(NR$^9$)(CO)NR$^{10a}$R$^{11a}$,
  (l) —CN, and
  (m) hydroxy,
(3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from:
  (a) —C$_{1-4}$alkyl which is unsubstituted or substituted with 1-5 fluoro,
  (b) halo,
  (c) hydroxy,
  (d) —OC$_{1-6}$alkyl which is unsubstituted or substituted with 1-5 fluoro,
  (e) —C$_{3-6}$cycloalkyl, and
  (f) phenyl, and
  (g) —CN,
(4) —C$_{3-6}$cycloalkyl, which is unsubstituted or substituted with 1-7 substituents each independently selected from: halo, hydroxy, —OC$_{1-6}$alkyl, trifluoromethyl and phenyl;

R$^9$ is independently selected from:
(1) hydrogen,
(2) —C$_{1-6}$ alkyl, which is unsubstituted or substituted with 1-6 substituents, substituents each independently selected from:
  (a) halo,
  (b) hydroxy,
  (c) —OC$_{1-6}$alkyl, which is unsubstituted or substituted with 1-5 halo,
  (d) —C$_{3-6}$cycloalkyl, and
  (e) phenyl, which is unsubstituted or substituted with 1-5 substituents each independently selected from:
    (i) —C$_{1-4}$alkyl,
    (ii) —OC$_{1-6}$alkyl,
    (iii) halo,
    (iv) trifluoromethyl, and
    (v) —OCF$_3$,
(3) —C3-6cycloalkyl, which is unsubstituted or substituted with 1-6 substituents, substituents each independently selected from:
  (a) halo,
  (b) hydroxy,
  (c) —O—C$_{1-6}$alkyl, which is unsubstituted or substituted with 1-5 halo,
  (d) —C$_{1-6}$alkyl, which is unsubstituted or substituted with 1-5 halo, and
  (e) phenyl,
(4) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
  (a) halo,
  (b) —C$_{1-6}$alkyl, which is unsubstituted or substituted with 1-5 halo
  (c) —OC$_{1-6}$alkyl, which is unsubstituted or substituted with 1-5 halo
  (d) —C$_{3-6}$cycloalkyl,
  (e) oxo,
  (f) —CN,
  (g) hydroxy, and
  (h) phenyl;

R$^{10}$ and R$^{11}$ are each independently selected from:
(1) hydrogen,
(2) —C$_{1-6}$alkyl, which is unsubstituted or substituted with 1-6 substituents each independently selected from:
  (a) halo,
  (b) hydroxy,
  (c) —OCF$_3$,
  (d) —C$_{3-6}$cycloalkyl, and
  (e) phenyl,
(3) —C$_{4-6}$cycloalkyl,
(4) phenyl, which is unsubstituted or substituted with 1-5 substituents each independently selected from:
  (a) —C$_{1-6}$alkyl, which is unsubstituted or substituted with 1-5 halo,
  (b) —OC$_{1-6}$alkyl, which is unsubstituted or substituted with 1-5 halo,
  (c) halo,
  (d) hydroxy,
  (e) trifluoromethyl,
  (f) —OCF$_3$, and
  (g) —CN,
(5) benzyl, which is unsubstituted or substituted with 1-5 substituents each independently selected from:
  (a) —C$_{1-6}$alkyl, which is unsubstituted or substituted with 1-5 halo,
  (b) —OC$_{1-6}$alkyl, which is unsubstituted or substituted with 1-5 halo, (c) halo, and
(d) trifluoromethyl,
(6) —COR$^9$, and
(7) —SO$_2$R$^{12}$;

$R^{10a}$ and $R^{11a}$ are each independently selected from:
(1) hydrogen,
(2) —C$_{1-6}$alkyl, which is unsubstituted or substituted with 1-6 substituents each independently selected from:
 (a) —O—C$_{1-6}$alkyl, which is unsubstituted or substituted with 1-5 halo,
 (b) halo,
 (c) hydroxy,
 (d) —OCF$_3$,
 (e) —C$_{3-6}$cycloalkyl, and
 (f) phenyl,
(3) —C$_{5-6}$cycloalkyl, which is unsubstituted or substituted with 1-5 halo,
(4) phenyl, which is unsubstituted or substituted with 1-5 substituents each independently selected from:
 (a) —C$_{1-6}$alkyl, which is unsubstituted or substituted with 1-5 halo,
 (b) —OC$_{1-6}$alkyl, which is unsubstituted or substituted with 1-5 halo,
 (c) halo,
 (d) hydroxy,
 (e) trifluoromethyl,
 (f) —OCF$_3$, and
 (g) —CN,
(5) benzyl, which is unsubstituted or substituted with 1-5 substituents each independently selected from:
 (a) —C$_{1-6}$alkyl, which is unsubstituted or substituted with 1-5 halo,
 (b) —OC$_{1-6}$alkyl, which is unsubstituted or substituted with 1-5 halo,
 (c) halo, and
 (d) trifluoromethyl, or where $R^{10a}$ and $R^{11a}$ join to form a ring selected from azetidinyl, pyrrolidinyl, piperidinyl, azepanyl, piperazinyl and morpholinyl, which ring is unsubstituted or substituted with 1-5 substituents each independently selected from:
(1) —C$_{1-6}$alkyl, which is unsubstituted or substituted with 1-5 halo,
(2) —O—C$_{1-6}$alkyl, which is unsubstituted or substituted with 1-5 halo,
(3) halo
(4) hydroxy
(5) phenyl, which is unsubstituted or substituted with 1-5 substituents each independently selected from:
 (a) —C$_{1-4}$alkyl, which is unsubstituted or substituted with 1-3 halo,
 (b) —O—C$_{1-4}$alkyl, which is unsubstituted or substituted with 1-3 halo, and
 (c) halo,
(6) benzyl, which is unsubstituted or substituted with 1-5 substituents each independently selected from:
 (a) —C$_{1-4}$alkyl, which is unsubstituted or substituted with 1-3 halo,
 (b) —OC$_{1-4}$alkyl, which is unsubstituted or substituted with 1-3 halo, and
 (c) halo,
(7) —COR$^9$, and
(8) —SO$_2$R$^{12}$;

$R^{12}$ is selected from:
(1) —C$_{1-6}$alkyl, which is unsubstituted or substituted with 1-6 fluoro,
(2) —C$_{3-6}$cycloalkyl,
(3) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
 which phenyl or heterocycle is unsubstituted or substituted with 1-5 substituents each independently selected from:
 (a) —C$_{1-6}$alkyl, which is unsubstituted or substituted with 1-5 halo,
 (b) —O—C$_{1-6}$alkyl, which is unsubstituted or substituted with 1-5 halo,
 (c) halo,
 (d) hydroxy,
 (e) trifluoromethyl,
 (f) —OCF$_3$,
 (g) —CN, and
 (h) benzyl, which is unsubstituted or substituted with 1-5 substituents each independently selected from:
  (i) —C$_{1-6}$alkyl, which is unsubstituted or substituted with 1-5 halo,
  (ii) —O—C$_{1-6}$alkyl, which is unsubstituted or substituted with 1-5 halo,
  (iii) halo, and
  (iv) trifluoromethyl;

$R^{13}$ and $R^{14}$ are each independently selected from:
(1) hydrogen,
(2) C$_{1-6}$alkyl, which is unsubstituted or substituted with 1-5 substituents each independently selected from:
 (a) —C$_{3-6}$cycloalkyl,
 (b) —OC$_{1-6}$alkyl,
 (c) halo,
 (d) hydroxy, and
 (e) phenyl,
(3) hydroxy, and
(4) halo;

$R^{15}$ is selected from:
(1) hydrogen,
(2) —C$_{1-6}$alkyl which is unsubstituted or substituted with 1-7 substituents where the substituents are independently selected from:
 (a) halo,
 (b) hydroxy,
 (c) —O—C$_{1-6}$alkyl,
 (d) —C$_{3-6}$cycloalkyl,
 (e) phenyl, and
 (f) —NR$^{10}$R$^{11}$;
(3) phenyl or heterocycle, wherein heterocycle is selected from: pyridyl, pyrimidinyl, pyrazinyl, or thienyl, which is unsubstituted or substituted with 1-5 substituents where the substituents are independently selected from:
 (a) —C$_{1-6}$alkyl,
 (b) —O—C$_{1-6}$alkyl,
 (c) halo,
 (d) hydroxy, and
 (e) trifluoromethyl;

m is 1 or 2; and
n is 1 or 2.

An embodiment of the present invention includes compounds of the formula Ia:

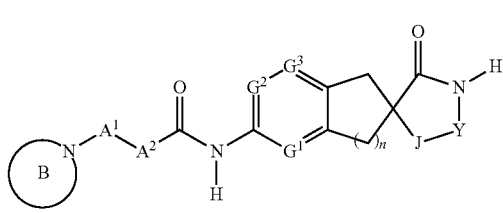

Ia wherein $A^1$, $A^2$, B, $G^1$, $G^2$, $G^3$, J, Y, and n are defined herein;

and pharmaceutically acceptable salts thereof and individual enantiomers and diastereomers thereof.

Another embodiment of the present invention includes compounds of the formula Ib:

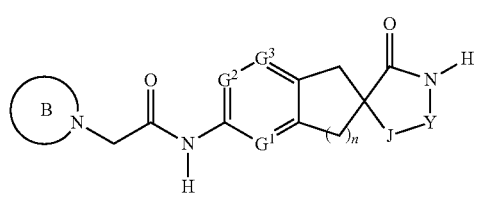

Ib wherein B, $G^1$, $G^2$, $G^3$, J, Y, and n are defined herein;

and pharmaceutically acceptable salts thereof and individual enantiomers and diastereomers thereof.

Another embodiment of the present invention includes compounds of the formula Ic:

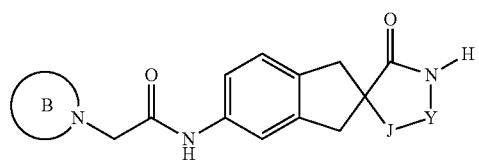

Ic wherein B, J, and Y are defined herein;

and pharmaceutically acceptable salts thereof and individual enantiomers and diastereomers thereof.

Another embodiment of the present invention includes compounds of the formula Id:

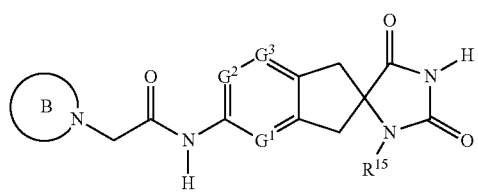

Id wherein B, $G^1$, $G^2$, $G^3$, and $R^{15}$ are defined herein;
and pharmaceutically acceptable salts thereof and individual enantiomers and diastereomers thereof.

Another embodiment of the present invention includes compounds of the formula Ie:

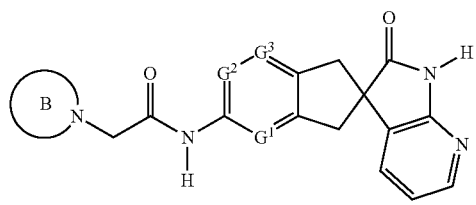

Ie wherein B, $G^1$, $G^2$, and $G^3$ are defined herein;

and pharmaceutically acceptable salts thereof and individual enantiomers and diastereomers thereof.

Another embodiment of the present invention includes compounds of the formula If:

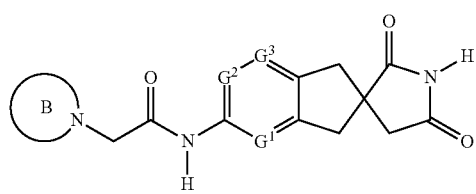

If wherein B, $G^1$, $G^2$, and $G^3$ are defined herein;

and pharmaceutically acceptable salts thereof and individual enantiomers and diastereomers thereof.

Another embodiment of the present invention includes compounds of the formula Ig:

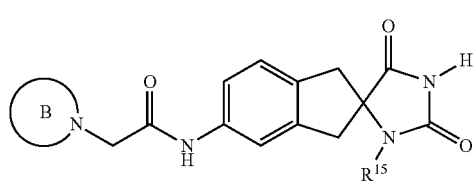

Ig wherein B and $R^{15}$ are defined herein;

and pharmaceutically acceptable salts thereof and individual enantiomers and diastereomers thereof.

Another embodiment of the present invention includes compounds of the formula Ih:

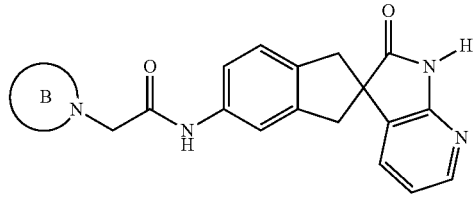

Ih wherein B is defined herein;

and pharmaceutically acceptable salts thereof and individual enantiomers and diastereomers thereof.

Another embodiment of the present invention includes compounds of the formula Ii:

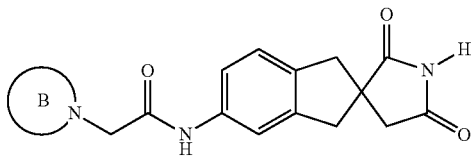

wherein B is defined herein;
and pharmaceutically acceptable salts thereof and individual enantiomers and diastereomers thereof.

In an embodiment of the present invention B is selected from the group consisting of:

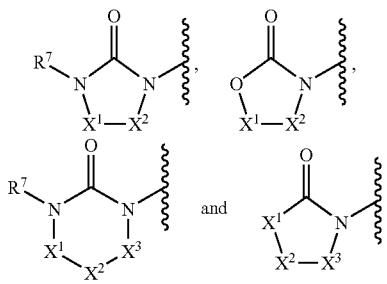

wherein $R^7$ is defined herein and $X^1$, $X^2$, and $X^3$ are each carbon, and one of $X^1$, $X^2$, and $X^3$ present on B is spirally substituted to form a ring or ring system selected from:
  indanyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, cycloheptyl, morpholinyl and tetrahydropyranyl,
  which ring is unsubstituted or substituted with one to seven substituents each independently selected from:
    (a) —$C_{1-4}$alkyl, which is unsubstituted or substituted with 1-3 substituents where the substituents are independently selected from: halo, hydroxy, —$OC_{1-6}$alkyl, and —$C_{3-6}$cycloalkyl,
    (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{1-6}$alkyl which is unsubstituted or substituted with 1-6 fluoro, and —$OC_{1-6}$alkyl which is unsubstituted or substituted with 1-6 fluoro, halo, or hydroxyl,
    (c) hydroxy,
    (d) —$OC_{1-6}$alkyl, which is unsubstituted or substituted with 1-5 halo,
    (e) halo,
    (f) —CN, and
    (g) —$C_{3-6}$cycloalkyl,
  and wherein the remaining members of the group $X^1$, $X^2$ and $X^3$ present on B are each independently unsubstituted or substituted with one or more substituents selected from $R^1$ and $R^2$, where:

$R^1$ and $R^2$ are each independently selected from:
  (1) —$C_{1-4}$alkyl, which is unsubstituted or substituted with 1-4 substituents each independently selected from:
    (a) halo,
    (b) hydroxy,
    (c) —O—$C_{1-6}$alkyl,
    (d) —$C_{3-6}$cycloalkyl, and
    (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl,
      which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
  (2) —$C_{3-6}$cycloalkyl, which is unsubstituted or substituted with 1-7 substituents each independently selected from: halo, hydroxy, —$OC_{1-6}$alkyl, trifluoromethyl and phenyl,
  (3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
    (a) —$C_{1-4}$alkyl, which is unsubstituted or substituted with 1-4 fluoro,
    (b) halo,
    (c) hydroxy,
    (d) —$OC_{1-3}$alkyl, which is unsubstituted or substituted with 1-3 fluoro,
    (e) —$C_{3-6}$cycloalkyl,
  (4) halo,
  (5) hydroxy,
  (6) —$OC_{1-6}$alkyl, which is unsubstituted or substituted with 1-5 halo,
  (7) —CN,
  (8) —$CO_2R^9$,
  (9) —$NR^{10}R^{11}$,
  (10) —$SO_2R^{12}$, and
  (11) —$CONR^{10a}R^{11a}$.

In another embodiment of the present invention, B is:

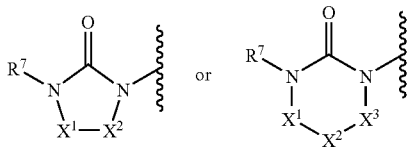

wherein $R^7$ is defined herein and $X^1$, $X^2$, and $X^3$ are each carbon, and one of $X^1$, $X^2$, and $X^3$ present on B is spirally substituted to form a ring or ring system selected from:
  indanyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, thiochromanyl, 6,7,8,9-tetrahydro-5H-benzo[7]annulenyl and cycloheptyl,
  which ring or ring system is unsubstituted or substituted with one to five substituents each independently selected from:
    (a) —$C_{1-4}$alkyl, which is unsubstituted or substituted with 1-4 substituents each independently selected from: halo, hydroxy, —$OC_{1-6}$alkyl, and —$C_{3-6}$cycloalkyl,
    (b) hydroxy, (c) —OC$_{1-4}$ alkyl, which is unsubstituted or substituted with 1-4 halo,
(d) halo, and
(e) —CN, and wherein the remaining members of the group X$^1$, X$^2$ and X$^3$ present on B are each independently unsubstituted or substituted with one or more substituents selected from R$^1$ and R$^2$, where:

R$^1$ and R$^2$ are each independently selected from:
(1) —C$_{1-4}$alkyl, which is unsubstituted or substituted with 1-4 substituents each independently selected from:
  (a) halo,
  (b) hydroxy,
  (c) —O—C$_{1-6}$alkyl,
  (d) —C$_{3-6}$cycloalkyl, and
  (e) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, which phenyl or heterocycle is unsubstituted or substituted with 1-5 substituents each independently selected from: —C$_{1-6}$alkyl, —OC$_{1-6}$alkyl, halo, hydroxy, trifluoromethyl, —CN, and —OCF$_3$,
(2) —C$_{3-6}$cycloalkyl, which is unsubstituted or substituted with 1-7 substituents each independently selected from: halo, hydroxy, —OC$_{1-6}$alkyl, trifluoromethyl and phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
  (a) —C$_{1-4}$alkyl, which is unsubstituted or substituted with 1-4 fluoro,
  (b) halo,
  (c) hydroxy,
  (d) —OC$_{1-3}$alkyl, which is unsubstituted or substituted with 1-3 fluoro, and
  (e) —C$_{3-6}$cycloalkyl,
(4) halo,
(5) hydroxy,
(6) —OC$_{1-6}$alkyl, which is unsubstituted or substituted with 1-5 halo, and
(7) —CN.

In an embodiment of the present invention B is selected from the group consisting of:

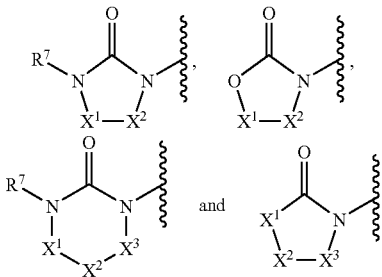

wherein R$^7$ is defined herein and X$^1$, X$^2$ and X$^3$ are each carbon, and one of X$^1$, X$^2$, and X$^3$ present on B is —(C═O)—,
wherein another one of the members of the group X$^1$, X$^2$ and X$^3$ present on B is optionally spirally substituted to form a ring or ring system selected from:

cyclopropyl, cyclobutyl, cyclopentyl, cyclohexyl, cycloheptyl, cyclooctyl, indanyl, azetidinyl, pyrrolidinyl, piperidinyl, piperazinyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, morpholinyl, tetrahydropyranyl, tetrahydrofuranyl, thiepanyl, oxepanyl and azepanyl, which ring is unsubstituted or substituted with one to seven substituents each independently selected from:
  (a) —C$_{1-4}$alkyl, which is unsubstituted or substituted with 1-3 substituents where the substituents are independently selected from: halo, hydroxy, —OC$_{1-6}$alkyl, —C$_{3-6}$cycloalkyl phenyl and heterocycle, wherein said heterocycle is selected from: pyridyl, pyrimidinyl, pyrazinyl, pyridazinyl, piperidinyl, piperazinyl, pyrrolidinyl, thienyl, and morpholinyl,
  (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —C$_{3-6}$cycloalkyl, —C$_{1-6}$alkyl which is unsubstituted or substituted with 1-6 fluoro, and —OC$_{1-6}$alkyl which is unsubstituted or substituted with 1-6 fluoro, halo, or hydroxyl,
  (c) hydroxy,
  (d) —OC$_{1-6}$alkyl, which is unsubstituted or substituted with 1-5 halo,
  (e) halo,
  (f) —CN, and
  (g) —C$_{3-6}$cycloalkyl, and wherein the remaining members of the group X$^1$, X$^2$ and X$^3$ present on B are each independently unsubstituted or substituted with one or more substituents selected from R$^1$ and R$^2$, where R$^1$ and R$^2$ are each independently selected from:
(1) —C$_{1-4}$alkyl, which is unsubstituted or substituted with 1-4 substituents each independently selected from:
  (a) halo,
  (b) hydroxy,
  (c) —O—C$_{1-6}$alkyl,
  (d) —C$_{3-6}$cycloalkyl, and
  (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —C$_{1-6}$alkyl, —OC$_{1-6}$alkyl, halo, hydroxy, trifluoromethyl, —CN, and —OCF$_3$,
(2) —C$_{3-6}$cycloalkyl, which is unsubstituted or substituted with 1-7 substituents each independently selected from: halo, hydroxy, —OC$_{1-6}$alkyl, trifluoromethyl and phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
  (a) —C$_{1-4}$alkyl, which is unsubstituted or substituted with 1-4 fluoro,
  (b) halo, (c) hydroxy,
(d) —$OC_{1-6}$alkyl, which is unsubstituted or substituted with 1-3 fluoro, and
(e) —$C_{3-6}$cycloalkyl,
(4) halo,
(5) hydroxy,
(6) —$OC_{1-6}$alkyl, which is unsubstituted or substituted with 1-5 halo,
(7) —CN,
(8) —$CO_2R^9$,
(9) —$NR^{10}R^{11}$,
(10) —$SO_2R^{12}$, and
(11) —$CONR^{10a}R^{11a}$.

Another embodiment of the present invention includes compounds wherein B is:

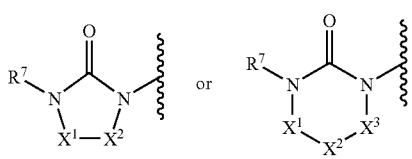

wherein $R^7$ is defined herein and $X^1$, $X^2$ and $X^3$ are each carbon, and one of $X^1$, $X^2$ and $X^3$ present on B is —(C=O)—, wherein another one of the members of the group $X^1$, $X^2$ and $X^3$ present on B is optionally spirally substituted to form a ring or ring system selected from:
  cyclopropyl, cyclobutyl, cyclopentyl, cyclohexyl, cycloheptyl, indanyl, azetidinyl, pyrrolidinyl, piperidinyl, piperazinyl, azaindanyl, 1,2,3,4-tetrahydronaphthalenyl, 5,6,7,8-tetrahydroquinolinyl, chromanyl, thiochromanyl, 6,7,8,9-tetrahydro-5H-benzo[7]annulenyl, morpholinyl, tetrahydropyranyl, thiepanyl, oxepanyl and azepanyl which ring is unsubstituted or substituted with one to five substituents each independently selected from:
  (a) —$C_{1-4}$alkyl, which is unsubstituted or substituted with 1-4 substituents where the substituents are independently selected from: halo, hydroxy, —$OC_{1-6}$alkyl, or —$C_{3-6}$cycloalkyl,
  (b) hydroxy,
  (c) —$OC_{1-4}$alkyl, which is unsubstituted or substituted with 1-4 halo,
  (d) halo, and
  (e) —CN,
and wherein the remaining members of the group $X^1$, $X^2$ and $X^3$ present on B are each independently unsubstituted or substituted with one or more substituents selected from $R^1$ and $R^2$, where:
$R^1$ and $R^2$ are each independently selected from:
  (1) —$C_{1-4}$alkyl, which is unsubstituted or substituted with 1-4 substituents each independently selected from:
    (a) halo,
    (b) hydroxy,
    (c) —O—$C_{1-6}$alkyl,
    (d) —$C_{3-6}$cycloalkyl, and
    (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
  (2) —$C_{3-6}$cycloalkyl, which is unsubstituted or substituted with 1-7 substituents each independently selected from: halo, hydroxy, —$OC_{1-6}$alkyl, trifluoromethyl and phenyl,
  (3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
    (a) —$C_{1-4}$alkyl, which is unsubstituted or substituted with 1-4 fluoro,
    (b) halo,
    (c) hydroxy,
    (d) —$OC_{1-3}$alkyl, which is unsubstituted or substituted with 1-3 fluoro, and
    (e) —$C_{3-6}$cycloalkyl,
  (4) halo,
  (5) hydroxy,
  (6) —$OC_{1-6}$alkyl, which is unsubstituted or substituted with 1-5 halo, and
  (7) —CN.

In an embodiment of the present invention B is 2-oxo-imidazolinyl.

In an embodiment of the present invention B is 2,4-dioxo-imidazolyl.

In an embodiment of the present invention B is 2,4-dioxo-dihydropyrimidinyl

In an embodiment of the present invention $R^1$ and $R^2$ are independently selected from:
  (1) $C_{1-6}$alkyl, which is unsubstituted or substituted with 1-5 substituents selected from: $C_{3-6}$cycloalkyl, halo and phenyl,
  (2) —$C_{3-6}$cycloalkyl, which is unsubstituted or substituted with 1-7 substituents each independently selected from: halo, hydroxy, —$OC_{1-6}$alkyl, trifluoromethyl and phenyl,
  (3) phenyl, which is unsubstituted or substituted with 1-5 substituents selected from: $C_{1-6}$alkyl, —O—$C_{1-6}$alkyl, halo, —OH and —$CF_3$, and,
  (4) heterocycle, wherein heterocycle is selected from: pyridyl, pyrimidinyl, pyrazinyl and thienyl, which heterocycle is unsubstituted or substituted with 1-5 substituents each independently selected from: $C_{1-6}$alkyl, —O—$C_{1-6}$alkyl, halo, —OH and —$CF_3$.

In an embodiment of the present invention $A^1$ is a bond.

In an embodiment of the present invention $A^2$ is —$CH_2$—.

In an embodiment of the present invention $G^1$, $G^2$, and $G^3$ are each independently selected from: —$C(R^5)$= and —N=, wherein $R^5$ is defined herein.

In an embodiment of the present invention $G^1$, $G^2$, and $G^3$ are —$C(R^5)$=, wherein $R^5$ is defined herein.

In an embodiment of the present invention $G^1$ is —N=, and $G^2$ and $G^3$ are —$C(R^5)$=, wherein $R^5$ is defined herein.

In an embodiment of the present invention $G^2$ is —N=, and $G^1$ and $G^3$ are —$C(R^5)$=, wherein $R^5$ is defined herein.

In an embodiment of the present invention $G^3$ is —N=, and $G^1$ and $G^2$ are —$C(R^5)$=, wherein $R^5$ is defined herein.

In an embodiment of the present invention J is =$C(R^{6a})$—, —$N(R^{15})$—, or —$CH_2$—, wherein $R^{6a}$ and $R^{15}$ are defined herein.

In an embodiment of the present invention J is =$C(R^{6a})$— or —$CH_2$—, wherein $R^{6a}$ is defined herein.

In an embodiment of the present invention J is —$N(R^{15})$—, wherein $R^{15}$ is defined herein.

In an embodiment of the present invention Y is =C($R^{6b}$)—, —CH$_2$— or —C(=O)—; wherein $R^{6b}$ is defined herein.

In an embodiment of the present invention Y is —CH$_2$—.

In an embodiment of the present invention Y is —C(=O)—.

In an embodiment of the present invention Y is =C($R^{6b}$)—; wherein $R^{6b}$ is defined herein.

In an embodiment of the present invention $R^4$ is selected from: hydrogen and —C$_{1-6}$alkyl, which is unsubstituted or substituted with fluoro.

In an embodiment of the present invention $R^4$ is hydrogen.

In an embodiment of the present invention $R^5$ is selected from hydrogen, C$_{1-6}$alkyl and halo.

In an embodiment of the present invention $R^5$ is selected from hydrogen and halo.

In an embodiment of the present invention $R^5$ is hydrogen.

In an embodiment of the present invention $R^{6a}$ and $R^{6b}$ are independently selected from:
  (1) hydrogen;
  (2) —C$_{1-4}$alkyl, which is unsubstituted or substituted with 1-3 substituents each independently selected from: halo, —O—C$_{1-6}$alkyl, —C$_{3-6}$cycloalkyl and phenyl,
  (3) phenyl or heterocycle, wherein heterocycle is selected from: pyridyl, pyrimidinyl, pyrazinyl, thiazolyl, oxazolyl, tetrahydrofuryl, piperidinyl, and morpholinyl, which phenyl or heterocycle is unsubstituted or substituted with 1-3 substituents each independently selected from: —C$_{1-4}$alkyl, which is unsubstituted or substituted with 1-3 fluoro, —O—C$_{1-4}$alkyl, which is unsubstituted or substituted with 1-3 fluoro, halo and hydroxy,
  (4) halo,
  (5) —NR$^{10}$R$^{11}$,
  (6) hydroxy, and
  (7) —O—C$_{1-4}$alkyl, which is unsubstituted or substituted with 1-3 halo.

In an embodiment of the present invention $R^{6a}$ and $R^{6b}$ are each independently selected from:
  (1) hydrogen;
  (2) —C$_{1-4}$alkyl which is unsubstituted or substituted with 1-3 fluoro, and
  (3) phenyl or heterocycle, wherein heterocycle is selected from: pyridyl, pyrimidinyl, pyrazinyl, thiazolyl, oxazolyl, tetrahydrofuryl, piperidinyl, and morpholinyl.

In an embodiment of the present invention $R^{6a}$ and $R^{6b}$ and the atom(s) to which they are attached are joined to form a ring selected from phenyl, pyridyl, pyrimidinyl, pyrazinyl, pyridazinyl, thiazolyl, oxazolyl, imidazolyl and thienyl, which ring is unsubstituted or substituted with 1-3 substituents each independently selected from:
  (1) —C$_{1-4}$alkyl, which is unsubstituted or substituted with 1-3 substituents where the substituents are each independently selected from: halo, —O—C$_{1-6}$alkyl, —CO$_2$R$^9$, —NR$^{10}$R$^{11}$ and —CONR$^{10a}$R$^{11a}$,
  (2) phenyl or heterocycle, wherein heterocycle is selected from: pyridyl, pyrimidinyl, pyrazinyl, pyrrolidinyl, azetidinyl, piperidinyl and morpholinyl, which phenyl or heterocycle is unsubstituted or substituted with 1-3 substituents each independently selected from: —C$_{1-4}$alkyl, which is unsubstituted or substituted with 1-5 fluoro, —O—C$_{1-4}$alkyl, which is unsubstituted or substituted with 1-3 fluoro, halo and hydroxyl,
  (3) halo,
  (4) hydroxy,
  (5) —O—C$_{1-6}$alkyl which is unsubstituted or substituted with 1-5 halo,
  (6) —CN,
  (7) —NR$^{10}$R$^{11}$,
  (8) —CONR$^{10a}$R$^{11a}$, and
  (9) oxo.

In an embodiment of the present invention $R^{6a}$ and $R^{6b}$ and the atom(s) to which they are attached join to form a ring selected from phenyl, pyridyl, and pyrimidinyl, which ring is unsubstituted or substituted with 1-3 substituents each independently selected from: —C$_{1-4}$alkyl which is unsubstituted or substituted with 1-3 fluoro, halo, hydroxy and —O—C$_{1-4}$alkyl.

In an embodiment of the present invention $R^{6a}$ and $R^{6b}$ and the atom(s) to which they are attached join to form a ring selected from pyridyl and pyrimidinyl.

In an embodiment of the present invention $R^7$ is selected from:
  (1) hydrogen;
  (2) —C$_{1-4}$alkyl, which is unsubstituted or substituted with 1-5 substituents where the substituents are each independently selected from:
    (a) halo,
    (b) —OC$_{1-6}$alkyl,
    (c) —C$_{3-6}$cycloalkyl,
    (d) phenyl or heterocycle, wherein heterocycle is selected from: pyridyl and pyrimidinyl, which phenyl or heterocycle is unsubstituted or substituted with 1-3 substituents each independently selected from: —CN, —C$_{1-6}$alkyl, —OC$_{1-6}$alkyl, halo, hydroxy, trifluoromethyl and —OCF$_3$,
    (e) —NR$^{10}$R$^{11}$,
    (f) —(NR$^{10a}$)CO$_2$R$^9$,
    (g) —(NR$^9$)(CO)NR$^{10a}$R$^{11a}$,
    (h) —CN, and
    (i) hydroxy,
  (3) phenyl or heterocycle, wherein heterocycle is selected from: pyridyl, pyrimidinyl, pyrazinyl and tetrahydrofuryl, which phenyl or heterocycle is unsubstituted or substituted with 1-3 substituents each independently selected from:
    (a) —C$_{1-4}$alkyl which is unsubstituted or substituted with 1-5 fluoro,
    (b) halo,
    (c) hydroxy,
    (d) —OC$_{1-6}$alkyl which is unsubstituted or substituted with 1-5 fluoro,
    (e) —C$_{3-6}$cycloalkyl,
    (f) phenyl, and
    (g) —CN,
  (4) —C$_{3-6}$cycloalkyl, which is unsubstituted or substituted with 1-7 substituents each independently selected from: halo, hydroxy, —OC$_{1-6}$alkyl, trifluoromethyl and phenyl.

In an embodiment of the present invention $R^7$ is selected from:
  (1) hydrogen;
  (2) —C$_{1-4}$alkyl, which is unsubstituted or substituted with 1-5 substituents each independently selected from:
    (a) halo,
    (b) —OC$_{1-2}$alkyl,
    (c) —C$_{3-6}$cycloalkyl,
    (d) phenyl or heterocycle, wherein heterocycle is selected from: pyridyl and pyrimidinyl,
    (e) —NR$^{10}$R$^{11}$,
    (f) —CN, and
    (g) hydroxy,
  (3) phenyl or pyridyl, which phenyl or pyridyl is unsubstituted or substituted with 1-3 substituents each independently selected from:

(a) —$C_{1-4}$alkyl which is unsubstituted or substituted with 1-5 fluoro,
(b) halo,
(c) hydroxy,
(d) —$OC_{1-6}$alkyl which is unsubstituted or substituted with 1-5 fluoro, and
(e) —CN, and
(4) —$C_{3-6}$cycloalkyl, which is unsubstituted or substituted with 1-7 substituents each independently selected from: halo, hydroxy, —$OC_{1-6}$alkyl, trifluoromethyl and phenyl.

In an embodiment of the present invention $R^9$ is selected from:
(1) hydrogen,
(2) —C1-6alkyl, which is unsubstituted or substituted with 1-6 substituents, substituents each independently selected from: halo and hydroxy,
(3) phenyl or heterocycle, wherein heterocycle is selected from: pyridinyl, pyrimidinyl, pyrazinyl, pyridazinyl, piperidinyl, piperazinyl, and morpholinyl, which phenyl or heterocycle is unsubstituted or substituted with 1-5 substituents each independently selected from:
(a) halo,
(b) —C1-6alkyl, which is unsubstituted or substituted with 1-5 halo,
(c) —OC1-6alkyl, which is unsubstituted or substituted with 1-5 halo,
(d) —C3-6cycloalkyl,
(e) oxo,
(f) —CN,
(g) hydroxy, and
(h) phenyl.

In an embodiment of the present invention $R^9$ is selected from:
(1) hydrogen,
(2) —$C_{1-4}$alkyl, which is unsubstituted or substituted with 1-4 substituents, substituents each independently selected from: halo and hydroxy,
(3) phenyl or heterocycle, wherein heterocycle is selected from: pyridinyl, piperidinyl, piperazinyl, and morpholinyl, which phenyl or heterocycle is unsubstituted or substituted with 1-5 substituents each independently selected from:
(a) halo,
(b) trifluoromethyl,
(c) —$OCF_3$
(e) oxo,
(f) —CN, and
(g) hydroxy.

In an embodiment of the present invention $R^{10}$ and $R^{11}$ are independently selected from:
(1) hydrogen,
(2) —$C_{1-6}$alkyl, which is unsubstituted or substituted with 1-6 substituents each independently selected from:
(a) halo,
(b) hydroxy,
(c) —$OCF_3$,
(d) —$C_{3-6}$cycloalkyl, and
(e) phenyl,
(3) —C4-6cycloalkyl,
(4) phenyl, which is unsubstituted or substituted with 1-5 substituents each independently selected from:
(a) —$C_{1-6}$alkyl, which is unsubstituted or substituted with 1-5 halo,
(b) —$OC_{1-6}$alkyl, which is unsubstituted or substituted with 1-5 halo,
(c) halo,
(d) hydroxy,
(e) trifluoromethyl,
(f) —$OCF_3$, and
(g) —CN,
(5) benzyl, which is unsubstituted or substituted with 1-5 substituents each independently selected from:
(a) —$C_{1-6}$alkyl, which is unsubstituted or substituted with 1-5 halo,
(b) —$OC_{1-6}$alkyl, which is unsubstituted or substituted with 1-5 halo,
(c) halo, and
(d) trifluoromethyl,
(6) —$COR^9$, and
(7) —$SO_2R^{12}$.

In an embodiment of the present invention $R^{10}$ and $R^{11}$ are independently selected from:
(1) hydrogen,
(2) —$C_{1-6}$alkyl, which is unsubstituted or substituted with 1-6 substituents each independently selected from:
(a) halo,
(b) —$C_{3-6}$cycloalkyl, and
(c) phenyl,
(3) —$C_{4-6}$cycloalkyl,
(4) phenyl, which is unsubstituted or substituted with 1-5 substituents each independently selected from:
(a) halo,
(b) hydroxy,
(c) trifluoromethyl,
(d) —$OCF_3$, and
(e) —CN,
(5) —$COR^9$.

In an embodiment of the present invention $R^{10a}$ and $R^{11a}$ are independently selected from:
(1) hydrogen,
(2) —$C_{1-4}$ alkyl, which is unsubstituted or substituted with 1-4 substituents each independently selected from:
(a) halo,
(b) hydroxy, and
(c) phenyl,
(3) —$C_{5-6}$ cycloalkyl, which is unsubstituted or substituted with 1-5 halo,
(4) phenyl, which is unsubstituted or substituted with 1-5 substituents each independently selected from:
(a) halo,
(b) hydroxy,
(c) trifluoromethyl,
(d) —$OCF_3$, and
(e) —CN,
or where $R^{10a}$ and $R^{11a}$ join to form a ring selected from azetidinyl, pyrrolidinyl, piperidinyl, azepanyl, piperazinyl and morpholinyl, which ring is unsubstituted or substituted with 1-5 substituents each independently selected from: halo and hydroxy.

In an embodiment of the present invention $R^{12}$ is selected from:
(1) —$C_{1-6}$alkyl, which is unsubstituted or substituted with 1-6 fluoro,
(2) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
which phenyl or heterocycle is unsubstituted or substituted with 1-5 substituents each independently selected from:
(a) halo,
(b) hydroxy,
(c) trifluoromethyl, (d) —OCF$_3$, and
(e) —CN.

In an embodiment of the present invention R$^{13}$ and R$^{14}$ are independently selected from:
(1) hydrogen,
(2) C$_{1-6}$ alkyl, which is unsubstituted or substituted with 1-5 substituents each independently selected from:
  (a) —C$_{3-6}$cycloalkyl,
  (b) —OC$_{1-6}$alkyl,
  (c) halo,
  (d) hydroxy, and
  (e) phenyl,
(3) hydroxy, and
(4) halo.

In an embodiment of the present invention R$^{13}$ and R$^{14}$ are independently selected from: hydrogen and hydroxy.

In an embodiment of the present invention R$^{15}$ is selected from:
(1) hydrogen,
(2) —C$_{1-4}$alkyl which is unsubstituted or substituted with 1-4 substituents where the substituents are independently selected from:
  (a) halo,
  (b) hydroxy,
  (c) —O—C$_{1-6}$alkyl,
  (d) —C$_{3-6}$cycloalkyl,
  (e) phenyl, and
  (f) —NR$^{10}$R$^{11}$,
(3) phenyl or heterocycle, wherein heterocycle is selected from: pyridyl, pyrimidinyl, pyrazinyl, or thienyl, which phenyl or heterocycle is unsubstituted or substituted with 1-5 substituents where the substituents are independently selected from:
  (a) —C$_{1-6}$alkyl,
  (b) —O—C$_{1-6}$alkyl,
  (c) halo,
  (d) hydroxy, and
  (e) trifluoromethyl.

In an embodiment of the present invention R$^{15}$ is selected from:
(1) hydrogen,
(2) —C$_{1-4}$alkyl which is unsubstituted or substituted with 1-4 substituents where the substituents are independently selected from:
  (a) halo,
  (b) hydroxy,
  (c) —O—C$_{1-6}$alkyl, and
  (d) —NR$^{10}$R$^{11}$.

In an embodiment of the present invention m is 1.
In an embodiment of the present invention n is 1.
In an embodiment of the present invention n is 2.

It is to be understood that where one or more of the above recited structures or substructures recite multiple substituents having the same designation each such variable may be the same or different from each similarly designated variable. For example, if R$^{12}$ is recited multiple times in certain configurations formula I, each such R$^{12}$ may independently be any of the substructures defined under R$^{12}$, and the invention is not limited to structures and substructures wherein each R$^{12}$ must be the same for a given structural configuration. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein on or more hydrogen atoms are replaced by deuterium.

Tautomers of compounds defined in Formula I are also included within the scope of the present invention. For example, compounds including carbonyl —CH$_2$C(O)— groups (keto forms) may undergo tautomerism to form hydroxyl —CH═C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Individual enantiomers of known absolute stereochemistry may be labeled as R or S, whereas those with unknown absolute stereochemistry may be designated by a different label, such as A or B. Similarly, diastereomers of unknown absolute stereochemistry may be labeled, for example, A or B. A racemic mixture may be labeled as ±.

Alternatively, any enantiomer of a compound may be obtained by stereoselective synthesis using optically pure starting materials or reagents of known configuration by methods well known in the art.

As will be appreciated by those of skill in the art, not all of the R$^{10}$ and R$^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no carbon-to-carbon double or triple bonds. Thus C$_{1-6}$alkyl is defined to identify the group as having 1, 2, 3, 4, 5 or 6 carbons in a linear or branched arrangement, such that C$_{1-6}$alkyl specifically includes, but is not limited to, methyl, ethyl, n-propyl, iso-propyl, n-butyl, iso-butyl, tert-butyl, pentyl and hexyl.

"Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_pC_{1-3}$ alkyl" this means that when there is one carbon, there are up to 2(1)+1=3 fluorines. When there are two carbons, there are up to 2(2)+1=5 fluorines, and when there are three carbons there are up to 2(3)+1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified (ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3'PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)^{nH}}$$
$$(Y_{max} - Y_{min})(\% \, I_{max} - \%_{Imin}/100) +$$

Where Y is observed CPM bound, $Y_{max}$ is total bound counts, $Y_{min}$ is non specific bound counts, ($Y_{max}-Y_{min}$) is specific bound counts, % $I_{max}$ is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 details the synthesis of the key indane-based spirohydantoin intermediates.

SCHEME 1

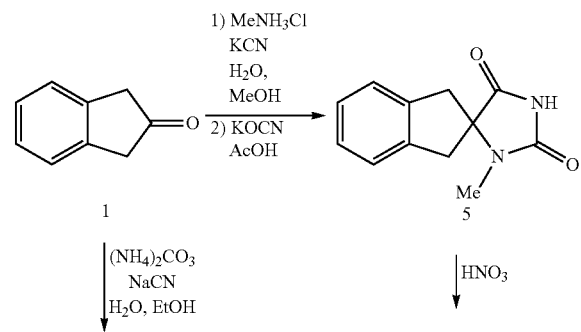

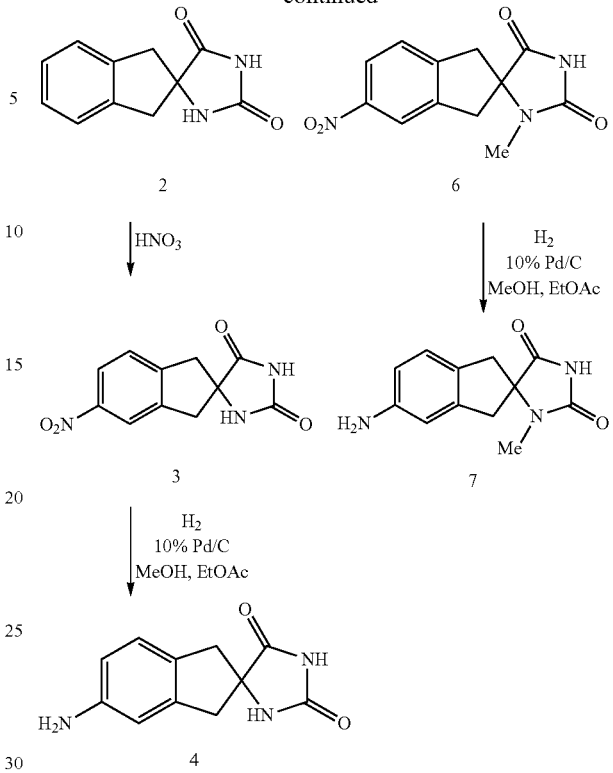

2-Indanone (1) is converted to the spirohydantoin 2 via Bucherer-Bergs chemistry as shown. Treatment of 2 with nitric acid provides the 5-nitroindane derivative 3, which may be reduced to the corresponding aniline 4 under catalytic hydrogenation conditions. Alternatively, a two-step process can be employed to convert 2-indanone (1) into the N-methylspirohydantoin 5. Treatment of 1 with potassium cyanide and methylamine hydrochloride affords an amino nitrile which is converted to the spirohydantoin 5 using potassium cyanate and acetic acid. Subjection of 5 to the nitration-reduction sequence used for 2 leads to the corresponding aniline 7, as detailed in Scheme 1.

Spirohydantoin intermediates may be resolved to give pure enantiomers using techniques familiar to those skilled in the art. For example, chromatography of the nitro intermediate 6 on a ChiralPak AD column can be used to provide the individual enantiomers (+)-6 and (−)-6, and these enantiomers may be reduced to the corresponding anilines [(+)-7 and (−)-7] by catalytic hydrogenation. Use of standard coupling procedures using enantiomerically pure anilines affords the individual enantiomers of the final products. Resolution may be effected by other methodologies, such as fractional crystallization of diastereomeric salts, and it may be carried out on other synthetic intermediates or on the final products. Alternatively, an assymetric synthesis of a key intermediate, such as an amino acid precursor of a spirohydantoin, could be used to provide an enantiomerically enriched final product.

Scheme 2 illustrates a route to spiroimide derivative 13. Ethyl indane-2-carboxylate (8) may be alkylated with tert-butyl bromoacetate to form the diester 9. Subjection of 9 to basic, then acidic hydrolysis conditions can provide the diacid 10. Treatment of the diacid 10 with a number of different reagents can provide imide 11 or a derivative thereof. In Scheme 2, heating 10 in the presence of acetyl chloride, followed by reaction with ammonia affords spiroimide 11.

Reaction with sodium nitrite in trifluoroacetic acid, followed by hydrogenation over palladium can provide the aniline 13.

shown in Scheme 3 is not limited to azaoxindoles such as 17, but may be applied to a variety of suitably protected heterocyclic systems to give the corresponding spiro compounds.

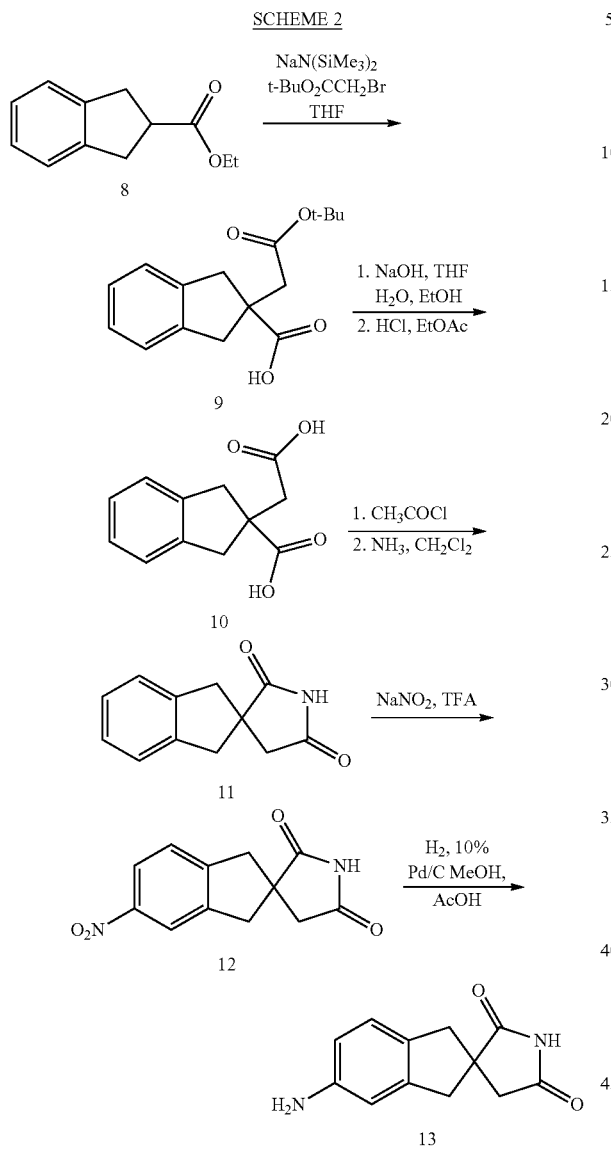

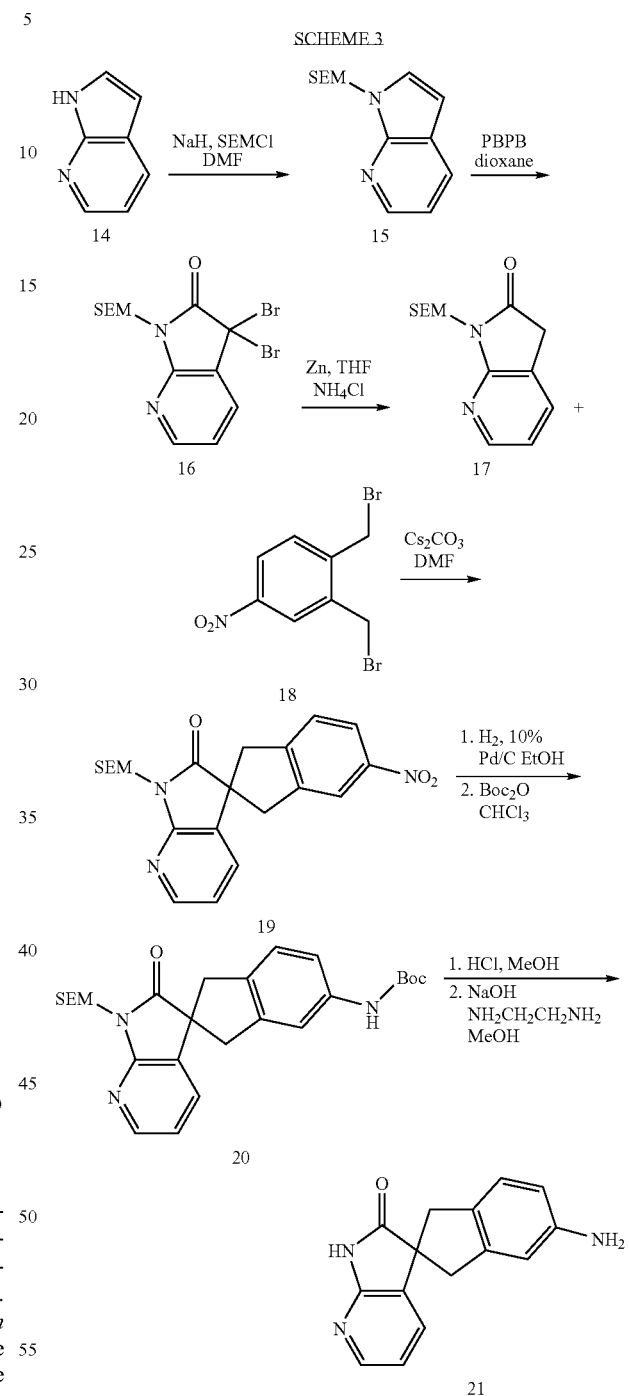

A representative synthesis of a spiroazaoxindole intermediate is shown in Scheme 3. 7-Azaindole (14) may be protected with a variety of protecting groups, such as the (trimethylsilyl)ethoxymethyl group shown in Scheme 3. Following the method of Marfat and Carter (*Tetrahedron Lett.*, 1987, 28, 4027-4030), treatment of 15 with pyridine hydrobromide perbromide provides the dibromoazaoxindole 16, which may be reduced to the corresponding azaoxindole 17 by reaction with zinc. The key alkylation of 17 with 1,2-bis(bromomethyl)-4-nitrobenzene (18, Cava et al., *J. Org. Chem.* 2000, 65, 5413-5415) is carried out using cesium carbonate in DMF to afford the spiroazaoxindole 19. A variety of other bases and solvents may be employed in this alkylation reaction, and use of an alternative alkylating agent to the dibromide shown here can lead to different products. Reduction of the nitro compound 19, for example using hydrogenation over palladium, and a two-step deprotection affords the corresponding aniline 21. The methodology Spiroazaoxindole intermediates, such as those illustrated in Scheme 3, may be resolved to give pure enantiomers using techniques familiar to those skilled in the art. For example, chromatography of the protected intermediate 20 on a Chiral-Pak AD column can be used to provide the individual enantiomers (+)-20 and (−)-20, and these enantiomers may be converted to the corresponding anilines [(+)-21 and (−)-21] by the two-step deprotection. In the case of compound 21, the dextro isomer is the (R)-enantiomer and the levo isomer (S)- enantiomer, i.e. (+)-21 is (R)-21 and (−)-21 is (S)-21. Use of standard coupling procedures using enantiomerically pure anilines can provide the individual enantiomers of the final products. Resolution may be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

The synthesis of some heterocyclic amine intermediates may be conducted as described in Schemes 4-6. The methodology shown in these schemes is not limited to the azaoxindoles shown but may be applied to a variety of heterocyclic systems to give the corresponding spiro compounds. Related intermediates bearing a variety of substituents may be prepared by employing appropriately substituted starting materials or by derivatization of any intermediates and/or final products as desired by methods known in the art.

Scheme 4 illustrates a route to the 3-aminopyridine 30. 7-Azaindole (22) may be protected with a variety of protecting groups, such as the 2-(trimethylsilyl)ethoxymethyl group shown in Scheme 4. Following the method of Marfat and Carter [(1987) *Tetrahedron Lett.* 28, 4027], treatment of 23 with pyridine hydrobromide perbromide provides the dibromoazaoxindole 24, which may be reduced to the corresponding azaoxindole 25 by reaction with zinc. Bis-alkylation of the azaoxindole 25 with allyl bromide, followed by ring closing metathesis and oxidation provides the cyclopentanone 26. Condensation of ketone 26 with ammonia and 1-methyl-3,5-dinitropyridin-2(1H)-one [Tohda et al. (1990) *Bull. Chem. Soc. Japan* 63, 2820] in refluxing methanol leads to the 3-nitropyridine derivative 28. Catalytic hydrogenation may be used to provide the corresponding amine 29. Standard deprotection of 29 using sequential acid and base treatments affords the 3-aminopyridine intermediate 30.

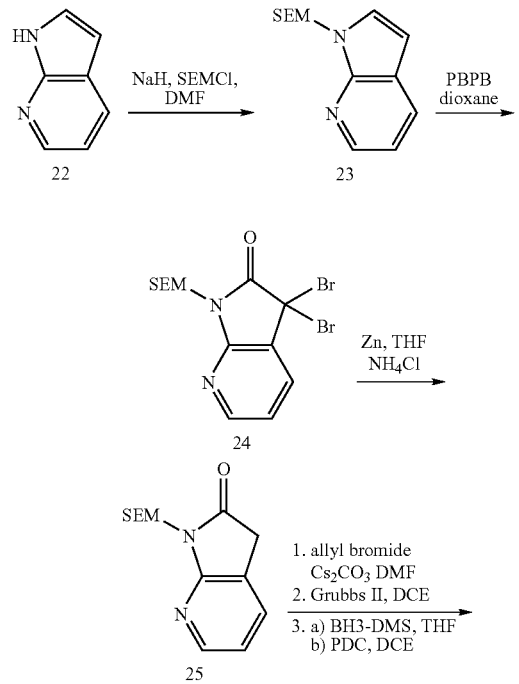

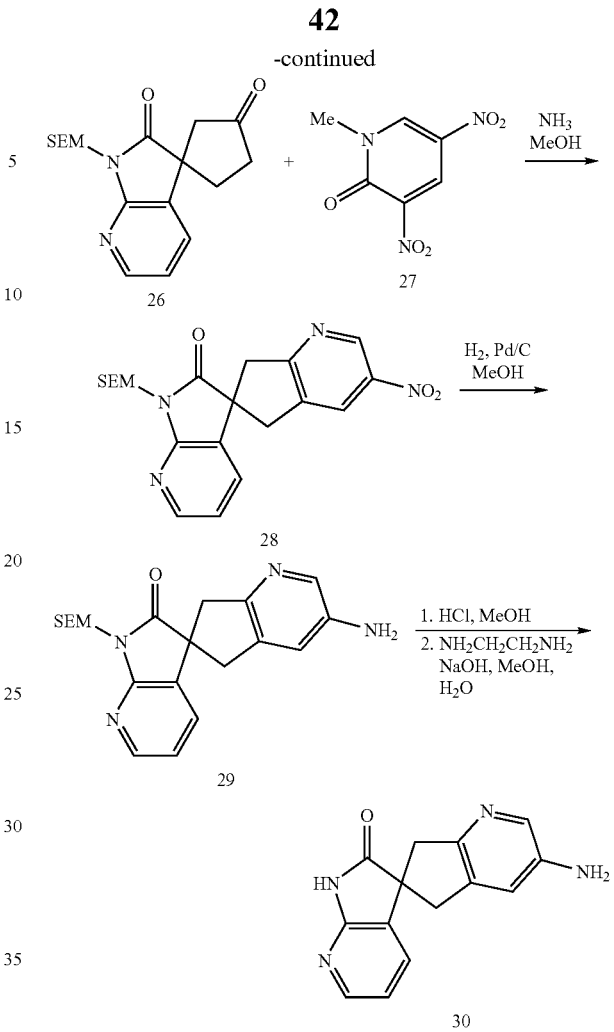

A representative synthesis of an isomer of compound 30, the 2-aminopyridine 36, is shown in Scheme 5. The known pyridine diester 31 [Hashimoto et al. (1997) *Heterocycles* 46, 581] may be reduced to the corresponding diol 32 with lithium borohydride. This diol can be converted to the dibromide 33 by reaction with phosphorus tribromide in THF. The previously described azaoxindole [Marfat & Carter (1987) *Tetrahedron Lett.* 28, 4027] may be reacted with dibromide 33 using lithium hydroxide in aqueous THF to afford the spiroazaoxindole 34. A variety of other bases and solvents may be employed in this alkylation reaction, and use of a different alkylating agent than the dibromide shown here can lead to other products. Treatment of compound 34 with aqueous NaOH at reflux effects hydrolysis of the nitrile, affording the carboxylate salt 35. This carboxylic acid salt may be subjected to known Curtius rearrangement conditions to provide, after deprotection, aminopyridine 36.

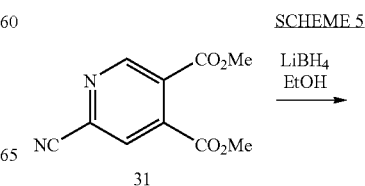

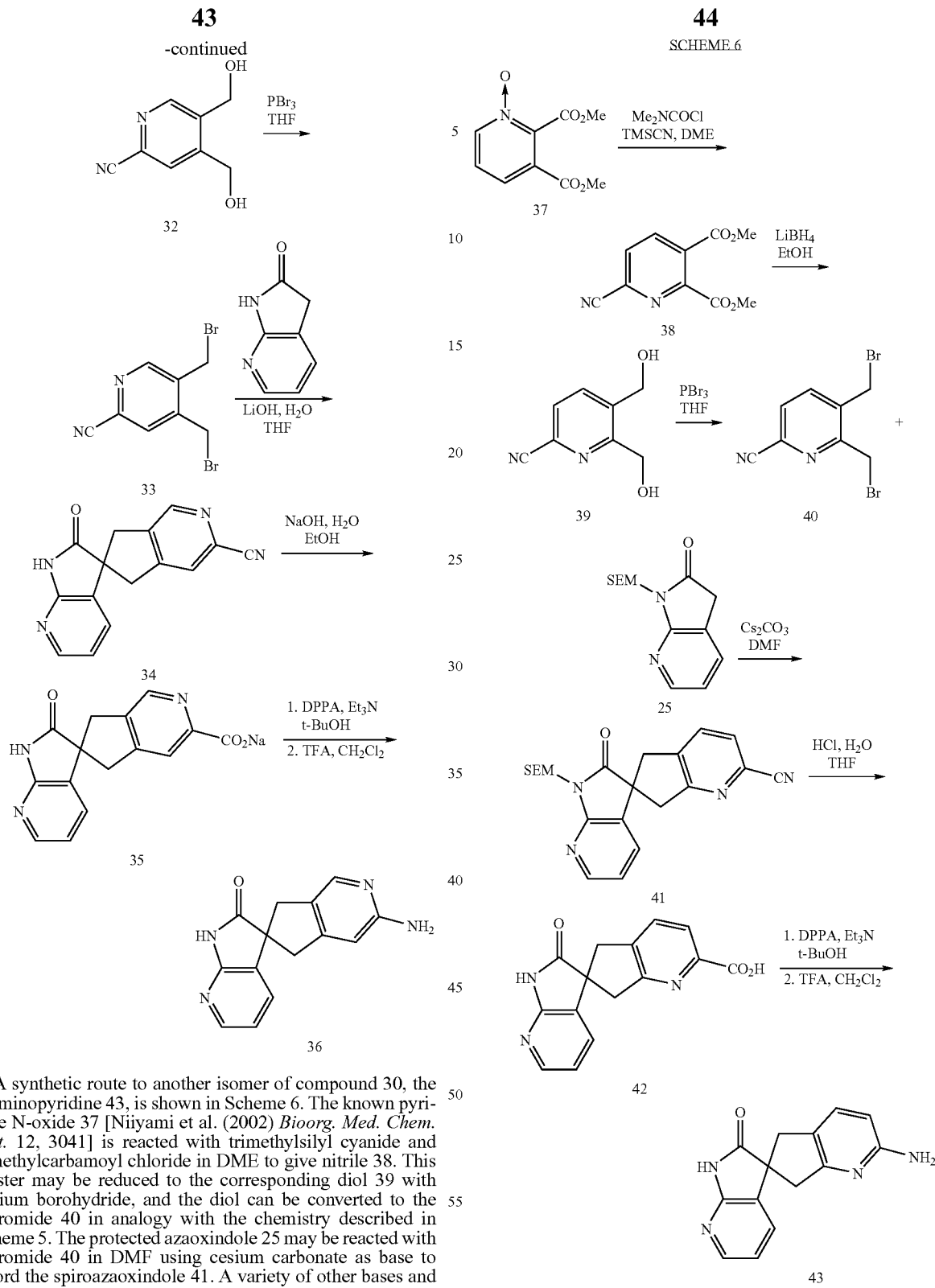

A synthetic route to another isomer of compound 30, the 2-aminopyridine 43, is shown in Scheme 6. The known pyridine N-oxide 37 [Niiyami et al. (2002) *Bioorg. Med. Chem. Lett.* 12, 3041] is reacted with trimethylsilyl cyanide and dimethylcarbamoyl chloride in DME to give nitrile 38. This diester may be reduced to the corresponding diol 39 with lithium borohydride, and the diol can be converted to the dibromide 40 in analogy with the chemistry described in Scheme 5. The protected azaoxindole 25 may be reacted with dibromide 40 in DMF using cesium carbonate as base to afford the spiroazaoxindole 41. A variety of other bases and solvents may be employed in this alkylation reaction, and use of a different alkylating agent than the dibromide shown here can lead to other products. Treatment of compound 41 with aqueous HCl at reflux effects simultaneous hydrolysis of the nitrile and deprotection of the azaoxindole, affording the key acid intermediate 42. This carboxylic acid may be subjected to a similar Curtius rearrangement and subsequent deprotection to that shown in Scheme 5 to afford the desired aminopyridine 43.

Spiroazaoxindole intermediates, such as those illustrated in these schemes (vide supra), may be resolved to give pure enantiomers using techniques familiar to those skilled in the art. For example, chromatography of the suitable intermediates on a chiral column can be used to provide the individual stereoisomers. Resolution may also be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

The synthesis of a number of hydantoin carboxylic acid intermediates may be conducted as described in Schemes 7-8.

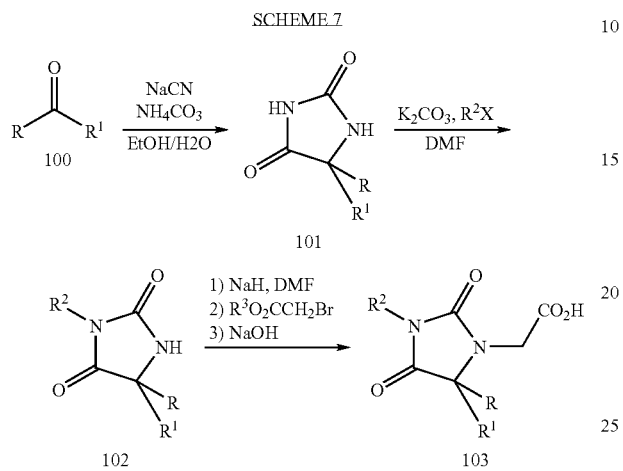

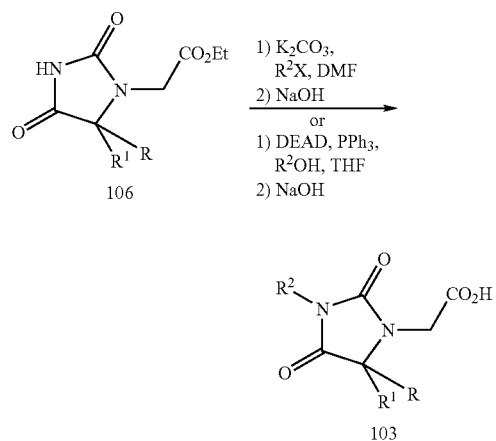

Readily available ketones (or aldehydes when R═H) may be converted to the spirohydantoin 101 under Bucherer-Bergs conditions, using ammonium carbonate and either sodium cyanide or potassium cyanide. The spirohydantoin 101 may be alkylated selectively on the imide nitrogen with, for example, iodomethane using potassium carbonate as base to provide the derivative 102 ($R^2$=Me). The spirohydantoin may be further alkylated with, for example, methylbromoacetate ($R^3$=Me) using sodium hydride as base and the intermediate ester can be saponified in situ using sodium hydroxide to provide the desired carboxylic acid derivative 103.

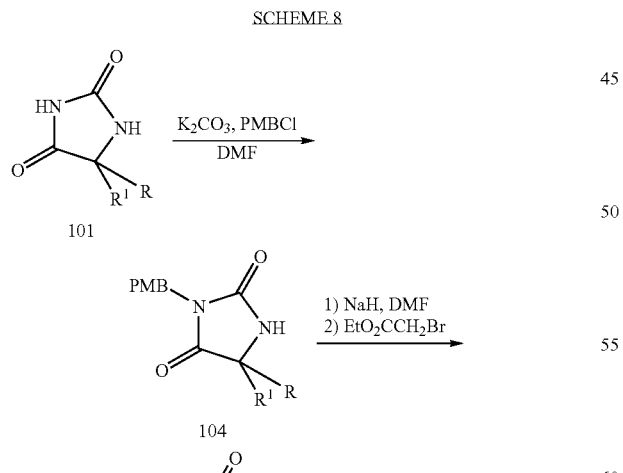

An alternative route to spirohydantoins of general structure 103 is shown in Scheme 8. In this case, spirohydantoin 101, may be protected on the imide nitrogen with, for example, 4-methoxybenzyl chloride using potassium carbonate as base to provide the intermediate 104. The spirohydantoin may be further alkylated with, for example, ethyl bromoacetate, to provide the desired ester derivative 105. The PMB protecting group can be removed under a variety of conditions, including oxidative deprotection using ammonium cerium nitrate. Intermediate 106 may then be alkylated on the imide nitrogen with, for example, ethyl iodide ($R^2$=Et) using potassium carbonate as base, followed by hydrolysis to provide the desired carboxylic acid derivative 103. Alternatively, the alkylation could be completed under Mitsonobu conditions using triphenylphosphine, DEAD, and an alcohol, such as 2-butanol.

The racemic spirohydantoin intermediates may be resolved to give pure enantiomers using techniques familiar to those skilled in the art. For example, chromatography of intermediate 106 on a ChiralPak AD column can be used to provide the individual enantiomers (+)-106 and (−)-106, and these enantiomers may be alkylated and hydrolyzed to the corresponding acids [(+)-103 and (−)-103]. Use of standard coupling procedures using enantiomerically pure anilines affords the individual enantiomers of the final products. Resolution may be effected by other methodologies, such as fractional crystallization of diastereomeric salts, and it may be carried out on other synthetic intermediates or on the final products. Alternatively, an assymetric synthesis of a key intermediate, such as an amino acid precursor of a spirohydantoin, could be used to provide an enantiomerically enriched final product.

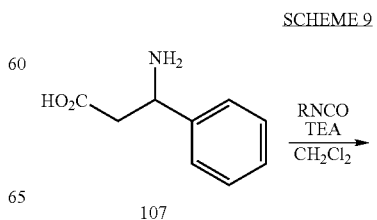

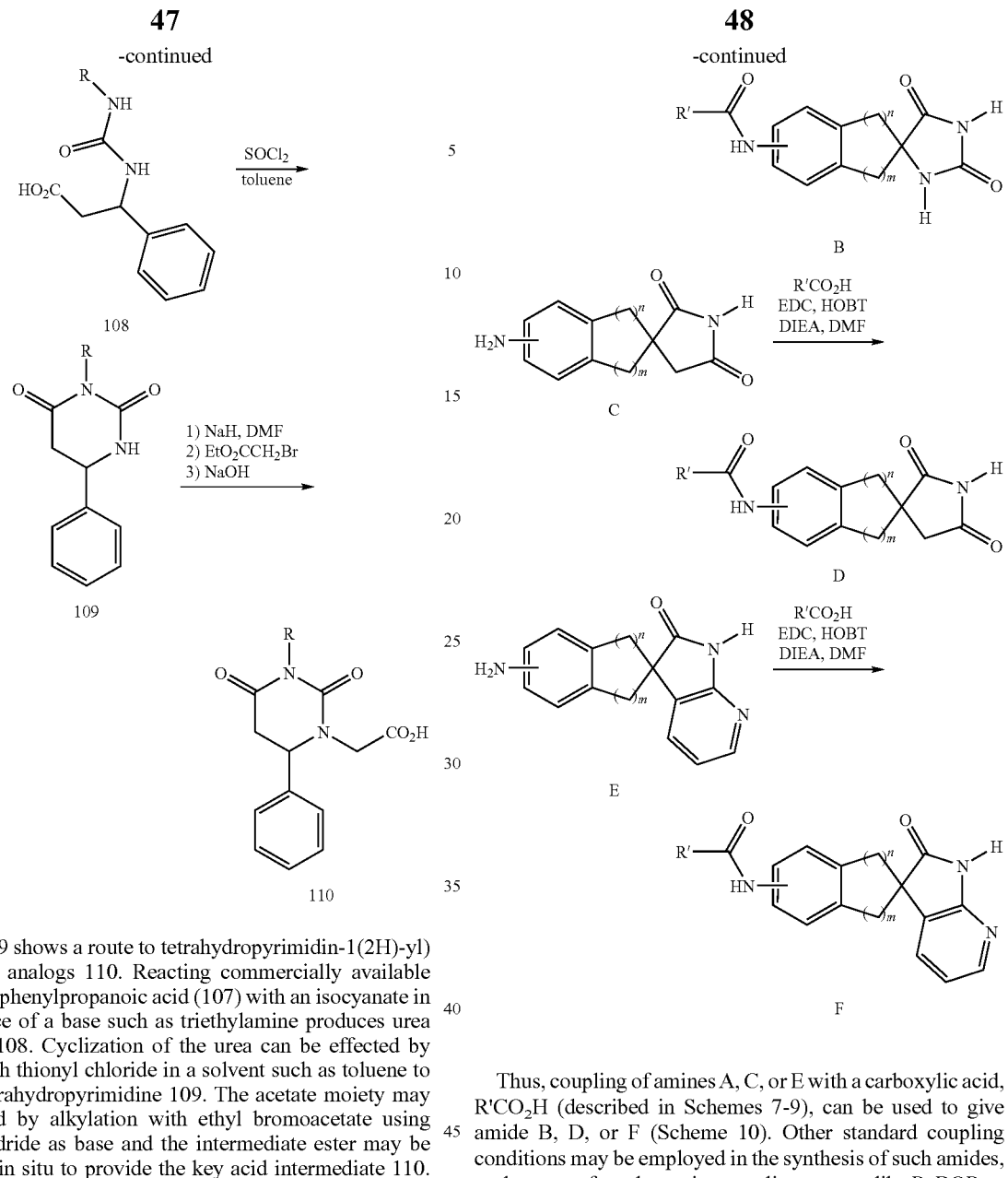

Scheme 9 shows a route to tetrahydropyrimidin-1(2H)-yl) acetic acid analogs 110. Reacting commercially available 3-amino-3-phenylpropanoic acid (107) with an isocyanate in the presence of a base such as triethylamine produces urea derivative 108. Cyclization of the urea can be effected by heating with thionyl chloride in a solvent such as toluene to provide tetrahydropyrimidine 109. The acetate moiety may be installed by alkylation with ethyl bromoacetate using sodium hydride as base and the intermediate ester may be saponified in situ to provide the key acid intermediate 110. Alternatively, the individual enantiomers (+)-110 and (−)-110 could be prepared in a similar manner by starting with a chiral 3-amino-3-phenylpropanoic acid [(+)-107 or (−)-107] or by chiral resolution of the intermediates or final carboxylic acid.

Carboxylic acid intermediates, such as those described in Schemes 7-9, may be further elaborated by techniques familiar to one skilled in the art to provide a variety of final products, for example amides, as shown in Scheme 10.

SCHEME 10

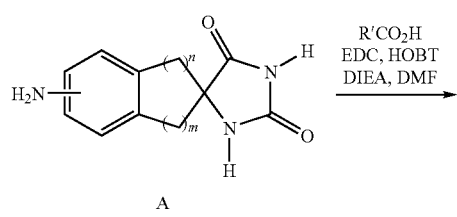

Thus, coupling of amines A, C, or E with a carboxylic acid, R'CO₂H (described in Schemes 7-9), can be used to give amide B, D, or F (Scheme 10). Other standard coupling conditions may be employed in the synthesis of such amides, such as use of an alternative coupling reagent like PyBOP, or activation of the carboxylic acid as an acid anhydride or acid chloride.

Simple modifications of these routes, including different protecting group strategies, application of well-precedented methodology, and the use of starting materials and reagents other than those described in the foregoing schemes, may be used to provide other acids of interest.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

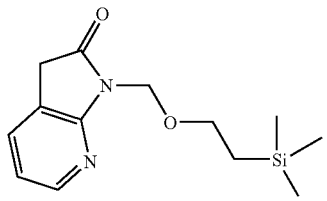

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc—90:10, to give the title compound. MS: m/z=265 (M+1).

INTERMEDIATE 2

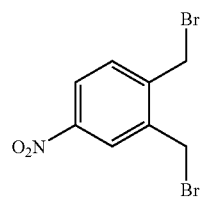

1,2-Bis(bromomethyl)-4-nitrobenzene

Step A. (4-Nitro-1,2-phenylene)dimethanol

A solution of 4-nitrophthalic acid (40 g, 189.5 mmol) in THF (500 mL) was added dropwise over 1.5 h to a solution of borane-THF complex (1 M, 490 mL, 490 mmol), keeping the reaction temperature between 0° C. and 5° C. After the addition, the reaction mixture was allowed to warm slowly to ambient temperature and stirred for 18 h. MeOH (100 mL) was added carefully and the precipitated solid dissolved. The mixture was concentrated in vacuo to about 500 mL, cooled to 0° C., and 10 N NaOH was added to adjust the pH to 10-11. This mixture was extracted with EtOAc (3×600 mL) and the combined organic layers were washed with brine, dried over $Na_2SO_4$, filtered, and concentrated in vacuo to give the title compound. MS: m/z=207 (M–OH+$CH_3CN$).

Step B. 1,2-Bis(bromomethyl)-4-nitrobenzene

Phosphorus tribromide (20.1 mL, 212 mmol) in $Et_2O$ (250 mL) was added dropwise over 1.5 h to a solution of (4-nitro-1,2-phenylene)dimethanol from Step A (35.3 g, 193 mmol) in $Et_2O$ (750 mL). After 18 h, the reaction mixture was cooled to 0° C. and quenched with $H_2O$ (100 mL). The layers were separated and the organic layer was washed with $H_2O$ (2×200 mL), then saturated aqueous $NaHCO_3$, dried over $Na_2SO_4$, filtered, and concentrated in vacuo to give the title compound. MS: m/z=309 (M+1).

INTERMEDIATE 3

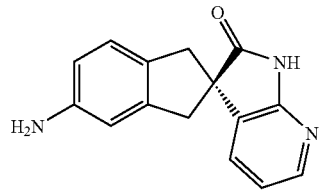

(R)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 2) and 1-{[2-

(trimethylsilyl)ethoxy]methyl}-1,3-dihydro-2H-pyrrolo[2,3-b]pyridin-2-one (31.5 g, 119 mmol, described in Intermediate 1) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and H₂O (1 L). The organic layer was washed with H₂O (1 L), then brine (500 mL), then dried over Na₂SO₄, filtered, and concentrated in vacuo. The crude product was purified by silica gel chromatography, eluting with a gradient of hexane:EtOAc—100:0 to 0:100, to give the title compound. MS: m/z=412 (M+1).

Step B. (±)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the title compound. MS: m/z=382 (M+1).

Step C. tert-Butyl (R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate A solution of (±)-5-amino-1'-{[2-(trimethylsilyl)ethoxy]methyl}-1,3-dihydrospiro[indene-2,3'-pyrrolo[2,3-b]pyridin]-2'(1'H)-one from Step B (104 g, 273 mmol) and di-tert-butyl dicarbonate (71.5 g, 328 mmol) in CHCl₃ (1 L) was heated to reflux for 17 h. The cooled mixture was concentrated in vacuo and the residue was purified by silica gel chromatography, eluting with hexane:EtOAc—100:0 to 50:50, to give the racemic product. The enantiomers were resolved by HPLC, utilizing a ChiralPak AD column and eluting with EtOH. The first major peak to elute was tert-butyl (S)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, and the second major peak to elute was tert-butyl (R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, the title compound. MS: m/z=482 (M+1).

Step D. (R)-5-Amino-1,3-dihydrospiro[indene-2,3'-pyrrolo[2,3-b]pyridin]-2'(1'H)-one A solution of tert-butyl (R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate from Step C (13.4 g, 27.8 mmol) in MeOH (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (1.9 mL, 27.8 mmol) and 10 N sodium hydroxide (6 mL, 60 mmol) to adjust the mixture to pH 10. After 30 min, the mixture was diluted with H₂O (400 mL) and extracted with CHCl₃ (1 L). The organic layer was dried over Na₂SO₄, filtered, and concentrated in vacuo. The crude material was triturated with MeOH (35 mL) to give the title compound. MS: m/z=252 (M+1).

INTERMEDIATE 4

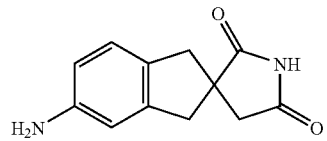

(+)-5-Amino-1,3-dihydro-2'H,5'H-spiro[indene-2,3'-pyrrolidine]-2',5'-dione

Step A. (±)-Ethyl 2-(2-tert-butoxy-2-oxoethyl)indane-2-carboxylate

To a solution of ethyl indane-2-carboxylate [Schaaf et al., J. Med. Chem. 1983, 26, 328-334] (2.00 g, 10.5 mmol) in THF at −78° C. was added sodium bis(trimethylsilyl)amide (15.8 mL of a 1.0 M solution in THF, 15.8 mmol) drop wise over 10 min. The mixture was stirred for 15 min, then tert-butyl bromoacetate (3.08 g, 15.8 mmol) was added drop wise over 30 min. The resulting mixture was stirred for 30 min at −78° C., then poured into brine (20 mL) and extracted with EtOAc (50 mL). The organic layer was dried over Na₂SO₄, filtered, and concentrated in vacuo. The crude product was purified by silica gel chromatography, eluting with a gradient of hexane:EtOAc—100:0 to 90:10, to give the title compound. MS: m/z=368 (M+Na+CH₃CN).

Step B. (±)-2-(2-tert-Butoxy-2-oxoethyl)indane-2-carboxylic acid

A mixture of (±)-ethyl 2-(2-tert-butoxy-2-oxoethyl)indane-2-carboxylate from Step A (2.48 g, 8.15 mmol) and 1.0 N sodium hydroxide (8.96 mL, 8.96 mmol) in THF (50 mL), H₂O (10 mL), and EtOH (20 mL) was stirred at ambient temperature for 18 h. The mixture was acidified with hydrochloric acid to about pH 3 and extracted with EtOAc (3×50 mL). The combined organic layers were dried over Na₂SO₄, filtered, and concentrated in vacuo to give the title compound as a white solid. MS: m/z=340 (M+Na+CH₃CN).

Step C. (±)-(Carboxymethyl)indane-2-carboxylic acid

A solution of (±)-2-(2-tert-butoxy-2-oxoethyl)indane-2-carboxylic acid from Step B (1.50 g, 5.43 mmol) in EtOAc (100 mL) was saturated with HCl (g) and aged at ambient temperature for 1 h, then concentrated to dryness in vacuo to give the title compound as a white solid. MS: m/z=284 (M+Na+CH₃CN).

Step D. (±)-1,3-Dihydro-2'H,5'H-spiro[indene-2,3'-pyrrolidine]-2',5'-dione

A solution of (±)-2-(carboxymethyl)indane-2-carboxylic acid from Step C (1.10 g, 4.99 mmol) in acetyl chloride (18 mL) was heated at reflux for 18 h, then concentrated in vacuo. The residue was recrystallized from toluene to give 1',3'-dihydrospiro[furan-3,2'-indene]-2,5(4H)-dione as an ivory solid. This solid was dissolved in CH₂Cl₂ (25 mL) and NH₃ (g) was bubbled into the mixture for 20 min. After a further 30 min, the solvent was evaporated under reduced pressure. The resulting solid was dried under high vacuum for 1 h, then resuspended in acetyl chloride (20 mL) and heated to reflux for 18 h. The solvent was removed in vacuo and the crude solid was recrystallized from EtOH:Et$_2$O to afford the title compound as a white solid. MS: m/z=202 (M+1).

Step E. (+)-5-Amino-1,3-dihydro-2'H,5'H-spiro[indene-2,3'-pyrrolidine]-2',5'-dione To a solution of (±)-1,3-dihydro-2'H,5'H-spiro[indene-2,3'-pyrrolidine]-2',5'-dione from Step D (400 mg, 1.99 mmol) in CF$_3$CO$_2$H (10 mL) was added sodium nitrite (411 mg, 5.96 mmol) and the mixture was heated to 55° C. for 2 h. The mixture was cooled and diluted with H$_2$O (10 mL), then extracted with EtOAc (2×30 mL). The combined organic layers were dried over Na$_2$SO$_4$, filtered, and concentrated in vacuo, to give 5-nitro-1,3-dihydro-2'H,5'H-spiro[indene-2,3'-pyrrolidine]-2',5'-dione, which contained some of the isomeric 4-nitro-1,3-dihydro-2'H,5'H-spiro[indene-2,3'-pyrrolidine]-2',5'-dione. This solid was dissolved in EtOH (30 mL), then AcOH (0.55 mL) and 10% Pd/C (55 mg) were added. The mixture was stirred vigorously under an atmosphere of hydrogen (ca. 1 atm) for 2 h, then filtered through a pad of Celite, and concentrated in vacuo. The crude product was purified by silica gel chromatography, eluting with a gradient of CH$_2$Cl$_2$:EtOAc—95:5 to 10:90, to give racemic title compound as a white solid. The enantiomers were resolved by HPLC, utilizing a ChiralPak OD column and eluting with MeOH. The first major peak to elute was (−)-5-amino-1,3-dihydro-2'H,5'H-spiro[indene-2,3'-pyrrolidine]-2',5'-dione and the second major peak to elute was (+)-5-amino-1,3-dihydro-2'H,5'H-spiro[indene-2,3'-pyrrolidine]-2',5'-dione, the title compound. MS: m/z=217 (M+1).

INTERMEDIATE 5

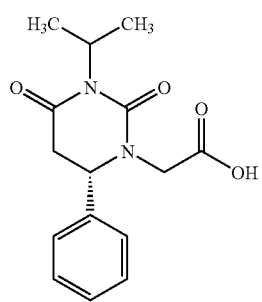

(S)-(3-Isopropyl-2,4-dioxo-6-phenyltetrahydropyrimidin-1(2H)-yl)acetic acid

Step A. (S)-3-{[(Isopropylamino)carbonyl]amino}-3-phenylpropanoic acid

To a stirred suspension of (S)-3-amino-3-phenylpropionic acid (1.22 g, 7.3 mmol) and TEA (1.24 mL, 8.86 mmol) in CH$_2$Cl$_2$ (30 mL) at ambient temperature was added isopropyl isocyanate (0.798 mL, 8.12 mmol). The reaction mixture was stirred for 3 h, diluted with 1M HCl (25 mL), and extracted with CH$_2$Cl$_2$ (3×25 mL). The combined CH$_2$Cl$_2$ extracts were dried over Na$_2$SO$_4$, filtered, and concentrated in vacuo to provide the title compound. MS: m/z=251 (M+1).

Step B. (S)-3-Isopropyl-6-phenyldihydropyrimidine-2,4(1H,3H)-dione

A solution of (S)-3-{[(isopropylamino)carbonyl]amino}-3-phenylpropanoic acid from Step A (465 mg, 1.86 mmol) and thionyl chloride (0.270 mL, 3.72 mmol) in toluene (19 mL) was heated at reflux for 1 h. The reaction mixture was cooled, diluted with water (25 mL), and extracted with CH$_2$Cl$_2$ (3×25 mL). The combined CH$_2$Cl$_2$ extracts were dried over Na$_2$SO$_4$, filtered, and concentrated in vacuo to provide the title compound. MS: m/z=233 (M+1).

Step C. (S)-3-Isopropyl-2,4-dioxo-6-phenyltetrahydropyrimidin-1(2H)-yl)acetic acid To a stirred solution of (S)-3-isopropyl-6-phenyldihydropyrimidine-2,4(1H,3H)-dione from Step B (310 mg, 1.34 mmol) in THF (6 mL) at 0° C. was added NaH (45.0 mg of a 60% dispersion in oil, 1.87 mmol). After 15 min, methyl bromoacetate (0.202 mL, 2.14 mmol) was added and the mixture was stirred at ambient temperature for 16 h. NaOH (4.00 mL of a 1M solution) was added and the mixture was stirred at ambient temperature for 2 h. A 10% citric acid solution (20 mL) was added and the mixture was extracted with CH$_2$Cl$_2$ (3×20 mL). The combined CH$_2$Cl$_2$ extracts were dried over Na$_2$SO$_4$, filtered, and concentrated in vacuo to provide the title compound. MS: m/z=291 (M+1).

INTERMEDIATE 6

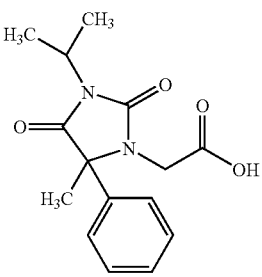

(3-Isopropyl-5-methyl-2,4-dioxo-5-phenylimidazolin-1-yl)acetic acid, isomer B

Step A. (±)-3-Isopropyl-5-methyl-5-phenylimidazoline-2,4-dione

To a stirred solution of (±)-5-methyl-5-phenylhydantoin (3.0 g, 15.7 mmol) in DMF (20 mL) was added potassium carbonate (2.6 g, 18.9 mmol) and 2-iodopropane (3.2 g, 18.9 mmol). The reaction was stirred at ambient temperature for 18 h and then partitioned between EtOAc (100 mL) and H$_2$O (100 mL). The layers were separated and the aqueous phase was extracted further with EtOAc (2×100 mL). The combined organic extracts were washed with brine (100 mL), dried over MgSO$_4$, filtered and concentrated under reduced pressure. The crude product was purified by silica gel chromatography, eluting with a gradient of hexane:EtOAc—75:25 to 50:50, to give the title compound. MS: m/z=233 (M+1).

Step B. Methyl (3-isopropyl-5-methyl-2,4-dioxo-5-phenylimidazolin-1-yl)acetate, isomer B To a stirred solution of (t)-3-isopropyl-5-methyl-5-phenyl imidazoline-2,4-dione from Step A (1.0 g, 4.3 mmol) in THF (50 mL) at 0° C. was added NaH (220 mg of a 60% dispersion in oil, 5.6 mmol). After 5 min, methyl bromoacetate (0.69 g, 4.52 mmol) was added and the mixture was stirred for 1 h. The reaction mixture was warmed to ambient temperature and then poured into saturated aqueous NaHCO$_3$ (200 mL) and extracted with EtOAc (2×250 mL). The combined organic extracts were washed with brine (100 mL), dried over MgSO₄, filtered and concentrated under reduced pressure. The crude product was purified by silica gel chromatography, eluting with a gradient of hexane:EtOAc—90:10 to 50:50, to give racemic title compound. The enantiomers were resolved by HPLC, utilizing a ChiralPak OD column and eluting with hexane:EtOH 60:40. The first major peak to elute was methyl (3-isopropyl-5-methyl-2,4-dioxo-5-phenylimidazolin-1-yl)acetate, isomer A, and the second major peak to elute was methyl (3-isopropyl-5-methyl-2,4-dioxo-5-phenylimidazolin-1-yl)acetate, isomer B, the title compound. MS: m/z=305 (M+1).

Step C. (−)-(3-Isopropyl-5-methyl-2,4-dioxo-5-phenylimidazolin-1-yl)acetic acid, isomer B To a stirred solution of methyl (3-isopropyl-5-methyl-2,4-dioxo-5-phenylimidazolin-1-yl)acetate, isomer B from Step B (700 mg, 2.3 mmol) in MeOH (20 mL) was added 1 N aqueous NaOH (5.0 mL, 5.0 mmol) and the resulting mixture was stirred at ambient temperature for 18 h. The reaction was quenched by addition of 1 N HCl (5 mL) and the reaction was poured into water (100 mL) and the mixture was adjusted to pH 3 with 1 N HCl. The aqueous mixture was extracted with EtOAc (2×50 mL). The combined organic extracts were washed with brine (50 mL), dried over MgSO₄, filtered and concentrated under reduced pressure to give the title compound. MS: m/z=291 (M+1).

INTERMEDIATE 7

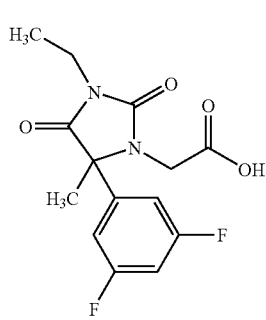

[5-(3,5-Difluorophenyl)-5-methyl-2,4-dioxo-3-ethylimidazolidin-1-yl]acetic acid, isomer A Step A. (±)-5-(3,5-Difluorophenyl)-5-methylimidazolidine-2,4-dione A suspension of 3',5'-difluoroacetophenone (5.00 g, 32.0 mmol), sodium cyanide (4.71 g, 96.1 mmol), and ammonium carbonate (30.8 g, 320 mmol) was heated at 70° C. in EtOH (60 mL) and water (60 mL) for 4 h. The reaction mixture was cooled to ambient temperature and the resulting precipitate filtered and rinsed with water to produce a white solid. The filtrate was extracted with EtOAc (2×250 mL). The combined organic extracts were washed with brine (100 mL), dried over MgSO₄, filtered and concentrated under reduced pressure. The crude product was combined with the solid collected above to provide the title compound. MS: m/z=227 (M+1).

Step B. (±)-5-(3,5-Difluorophenyl)-3-(4-methoxybenzyl)-5-methylimidazolidine-2,4-dione To a stirred solution of (±)-5-(3,5-difluorophenyl)-5-methylimidazolidine-2,4-dione from Step A (6.53 g, 28.9 mmol) in DMF (60 mL) was added potassium carbonate (4.39 g, 31.8 mmol) and 4-methoxybenzyl chloride (3.92 mL, 28.9 mmol). The reaction was stirred at ambient temperature for 16 h and at 50° C. for 1 h and then quenched with H₂O (100 mL). The resulting precipitate was filtered and rinsed with water to provide the title compound. MS: m/z=347 (M+1).

Step C. (±)-Ethyl[5-(3,5-difluorophenyl)-3-(4-methoxybenzyl)-5-methyl-2,4-dioxoimidazolidin-1-yl] acetate To a stirred solution of (±)-5-(3,5-difluorophenyl)-3-(4-methoxybenzyl)-5-methylimidazolidine-2,4-dione from Step B (9.99 g, 28.8 mmol) in DMF (60 mL) at ambient temperature was added NaH (831 mg of a 60% dispersion in oil, 34.6 mmol). After 30 min, ethyl bromoacetate (3.84 mL, 34.6 mmol) was added and the mixture was stirred for 16 h. The reaction mixture was quenched with H₂O (100 mL) and the resulting precipitate was filtered and rinsed with water to provide the title compound. MS: m/z=433 (M+1).

Step D. Ethyl[5-(3,5-difluorophenyl)-5-methyl-2,4-dioxoimidazolidin-1-yl]acetate, isomer A To a stirred solution of (±)-ethyl[5-(3,5-difluorophenyl)-3-(4-methoxybenzyl)-5-methyl-2,4-dioxoimidazolidin-1-yl] acetate from Step C (11.4 g, 26.3 mmol) in CH₃CN (150 mL) was added drop wise a solution of ammonium cerium (IV) nitrate (43.2 g, 78.8 mmol) in water (100 mL) and the resulting mixture was stirred at ambient temperature for 3 h. The reaction was diluted with water (300 mL) and extracted with EtOAc (3×250 mL). The combined organic extracts were washed with water (50 mL), saturated NaHCO₃ (50 mL), and brine (50 mL), dried over MgSO₄, filtered and concentrated under reduced pressure. The crude product was purified by silica gel chromatography, eluting with a gradient of hexane: EtOAc—100:0 to 50:50, to give the racemic title compound. The enantiomers were resolved by HPLC, utilizing a ChiralPak AD column and eluting with hexane:EtOH:DEA 40:60:1. The first major peak to elute was ethyl[5-(3,5-difluorophenyl)-5-methyl-2,4-dioxoimidazolidin-1-yl]acetate, isomer A, the title compound, and the second major peak to elute was ethyl[5-(3,5-difluorophenyl)-5-methyl-2,4-dioxoimidazolidin-1-yl]acetate, isomer B. MS: m/z=313 (M+1).

Step E. [5-(3,5-Difluorophenyl)-5-methyl-2,4-dioxo-3-ethylimidazolidin-1-yl]acetic acid, isomer A To a stirred solution of ethyl[5-(3,5-difluorophenyl)-5-methyl-2,4-dioxoimidazolidin-1-yl]acetate, isomer A from Step D (50.0 mg, 0.160 mmol) in DMF (1 mL) was added potassium carbonate (33.0 mg, 0.192 mmol) and iodoethane (0.015 mL, 0.192 mmol). The reaction was stirred at ambient temperature for 18 h and then a solution of 1 N NaOH (0.480 mL, 0.480 mmol) was added and stirring continued for 3 h. The reaction mixture was diluted with DMSO (1 mL), filtered, and purified directly by HPLC using a reversed phase C18 column and eluting with a gradient of H₂O:CH₃CN:CF₃CO₂H—90: 10:0.1 to 5:95:0.1. Lyophilization provided the racemic title compound. MS: m/z=313 (M+1).

Intermediates 8-43

Essentially following analogous procedures to those outlined for Intermediates 5-7, the compounds listed in Table 1 were prepared. The requisite starting materials were commercially available, described in the literature, or readily synthesized by one skilled in the art of organic synthesis. In some cases, straightforward protecting group strategies were applied.

TABLE 1

| Intermediate | R$^c$ | MS (M + 1) | Stereochemistry |
|---|---|---|---|
| 8 | (3-isopropyl-2,4-dioxo-hexahydropyrimidin-6-yl)phenyl | 291 | ± |
| 9 | 5-cyclobutyl-5-phenyl-3-(2,2,2-trifluoroethyl)hydantoin | 371 | ± |
| 10 | 5-ethyl-5-phenyl-3-(2,2,2-trifluoroethyl)hydantoin | 345 | ± |
| 11 | 3-(2,2,2-trifluoroethyl)-1,3-diazaspiro[4.6]undecane-2,4-dione | 323 | none |

TABLE 1-continued

| Intermediate | R$^c$ | MS (M + 1) | Stereochemistry |
|---|---|---|---|
| 12 | spiro[indane-2,5'-hydantoin]-3'-(2,2,2-trifluoroethyl) | 343 | none |
| 13 | 3-isopropyl-5-methyl-5-phenylhydantoin | 291 | ± |
| 14 | 3-isopropyl-5-methyl-5-phenylhydantoin | 291 | A |
| 15 | 5-methyl-5-phenyl-3-(2,2,2-trifluoroethyl)hydantoin | 331 | ± |
| 16 | 5-methyl-5-phenyl-3-(2,2,2-trifluoroethyl)hydantoin | 331 | A |

TABLE 1-continued
$$R^c\!\!-\!\!\overset{O}{\underset{OH}{\parallel}}$$
| Inter-mediate | R$^c$ | MS (M + 1) | Stereo-chemistry |
|---|---|---|---|
| 17 | 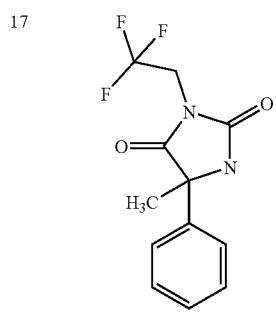 | 331 | B |
| 18 | 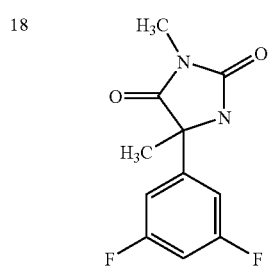 | 299 | A |
| 19 | 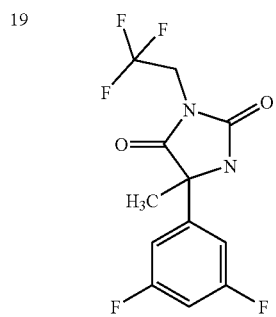 | 367 | ± |
| 20 | 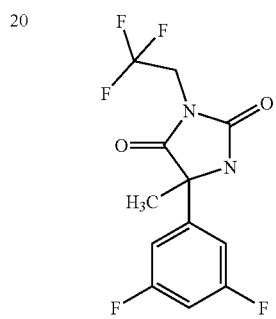 | 367 | A |
TABLE 1-continued
$$R^c\!\!-\!\!\overset{O}{\underset{OH}{\parallel}}$$
| Inter-mediate | R$^c$ | MS (M + 1) | Stereo-chemistry |
|---|---|---|---|
| 21 | 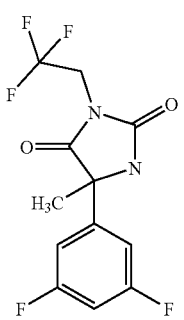 | 367 | B |
| 22 | 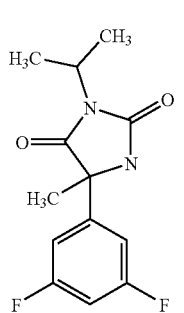 | 327 | A |
| 23 | 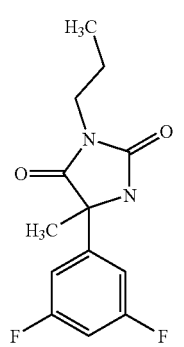 | 327 | A |
| 24 | 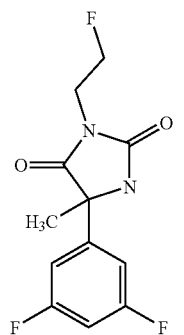 | 331 | A |

TABLE 1-continued
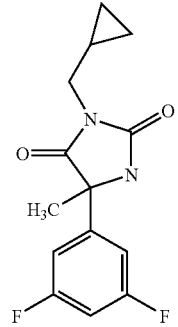
| Intermediate | $R^c$ | MS (M + 1) | Stereochemistry |
|---|---|---|---|
| 25 | 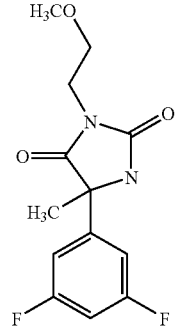 | 339 | A |
| 26 |  | 343 | A |
| 27 | 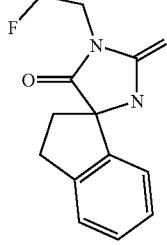 | 343 | ± |
| 28 | 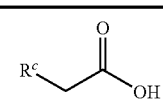 | 343 | A |
| 29 | 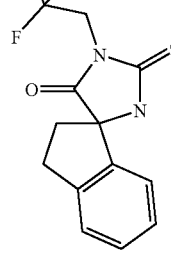 | 343 | B |
| 30 |  | 357 | ± |
| 31 | 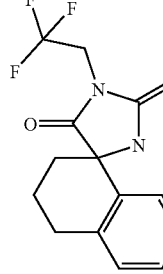 | 357 | A |
| 32 | 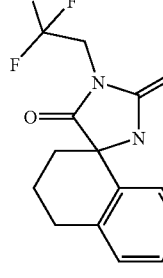 | 357 | B |
| 33 | 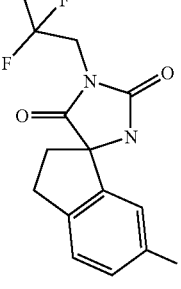 | 361 | ± |

TABLE 1-continued $$R^c\text{—CH}_2\text{—C(=O)—OH}$$

| Intermediate | $R^c$ | MS (M + 1) | Stereochemistry |
|---|---|---|---|
| 34 | 2,2,2-trifluoroethyl-substituted spiro[indane-hydantoin] with F on indane ring | 361 | A |
| 35 | 2,2,2-trifluoroethyl-substituted spiro[indane-hydantoin] with two F on indane ring | 379 | ± |
| 36 | 2,2,2-trifluoroethyl-substituted spiro[indane-hydantoin] with two F on indane ring | 379 | A |
| 37 | 2,2,2-trifluoroethyl-substituted spiro[indane-hydantoin] with F on indane ring | 361 | A |
| 38 | 2,2,2-trifluoroethyl-substituted spiro[indane-hydantoin] with F on indane ring | 361 | ± |
| 39 | isopropyl-substituted spiro[indane-hydantoin] | 303 | A |
| 40 | 2,2,2-trifluoroethyl-substituted spiro[chromane-hydantoin] | 359 | ± |
| 41 | 2,2,2-trifluoroethyl-substituted spiro[chromane-hydantoin] with F on aromatic ring | 377 | ± |

TABLE 1-continued

R<sup>c</sup>—CH<sub>2</sub>—C(=O)—OH

| Intermediate | R<sup>c</sup> | MS (M + 1) | Stereochemistry |
|---|---|---|---|
| 42 | (2,2,2-trifluoroethyl-substituted spiro hydantoin with benzocycloheptane) | 371 | ± |
| 43 | (isopropyl-substituted 5-phenyl hydantoin) | 277 | ± |

INTERMEDIATE 44

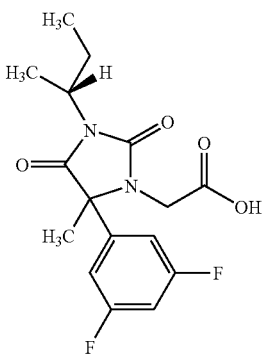

(3R)-[5-(3,5-Difluorophenyl)-5-methyl-2,4-dioxo-3-(2-butyl)imidazolidin-1-yl]acetic acid, isomer A Step A. (3R)-[5-(3,5-Difluorophenyl)-5-methyl-2,4-dioxo-3-(2-butyl)imidazolidin-1-yl]acetic acid, isomer A To a stirred solution of ethyl[5-(3,5-difluorophenyl)-5-methyl-2,4-dioxoimidazolidin-1-yl]acetate, isomer A (50.0 mg, 0.160 mmol, described in Intermediate 7), (S)-2-butanol (24.0 mg, 0.320 mmol), and triphenylphosphine (84.0 mg, 0.320 mmol) in THF (1.4 mL) was added a solution of DEAD (0.058 mL, 0.320 mmol) in THF (0.2 mL). The reaction was stirred at ambient temperature for 18 h and then a solution of 1 N NaOH (0.480 mL, 0.480 mmol) was added and stirring continued for 3 h. The reaction mixture was diluted with DMSO (1 mL), filtered, and purified directly by HPLC using a reversed phase C18 column and eluting with a gradient of H<sub>2</sub>O:CH<sub>3</sub>CN:CF<sub>3</sub>CO<sub>2</sub>H—90:10:0.1 to 5:95:0.1. Lyophilization provided the racemic title compound. MS: m/z=341 (M+1).

Intermediates 45-47

Essentially following analogous procedures to those outlined for Intermediate 43, the compounds listed in Table 2 were prepared. The requisite starting materials were commercially available, described in the literature, or readily synthesized by one skilled in the art of organic synthesis. In some cases, straightforward protecting group strategies were applied.

TABLE 2

R<sup>c</sup>—CH<sub>2</sub>—C(=O)—OH

| Intermediate | R<sup>c</sup> | MS (M + 1) |
|---|---|---|
| 45 | (sec-butyl-substituted 5-methyl-5-(3,5-difluorophenyl) hydantoin) | 341 |
| 46 | (cyclopentyl-substituted 5-methyl-5-(3,5-difluorophenyl) hydantoin) | 329 |
| 47 | (cyclopentyl-substituted spiro indane hydantoin) | 343 |

INTERMEDIATE 48

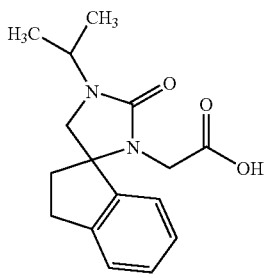

(±)-(1-Isopropyl-2-oxo-2',3'-dihydro-3H-spiro[imidazolidine-4,1'-inden]-3-yl)acetic acid

Step A. (±)-1-Isopropyl-2',3'-dihydro-2H-spiro[imidazolidine-4,1'-inden]-2-one To a stirred solution of (±)-2',3'-dihydro-2H-spiro[imidazolidine-4,1'-inden]-2-one (prepared according to Sarges, R. et al, J. Med. Chem., 1988, 31, 230-243) (100 mg, 0.531 mmol) in DMF (1 mL) at ambient temperature was added NaH (21.2 mg of a 60% dispersion in oil, 0.531 mmol). After 30 min, 2-iodopropane (0.053 mL, 0.531 mmol) was added and the mixture was stirred for 22 h. The reaction mixture was quenched with a drop of TFA and purified directly by HPLC using a reversed phase C18 column and eluting with a gradient of $H_2O:CH_3CN:CF_3CO_2H$—90:10:0.1 to 5:95:0.1. Lyophilization provided the title compound. MS: m/z=231 (M+1).

Step B. (±)-(1-Isopropyl-2-oxo-2',3'-dihydro-3H-spiro[imidazolidine-4,1'-inden]-3-yl)acetic acid To a stirred solution of (±)-1-isopropyl-2',3'-dihydro-2H-spiro[imidazolidine-4,1'-inden]-2-one from Step A (30.0 mg, 0.130 mmol) in DMF (1 mL) at 0° C. was added NaH (6.25 mg of a 60% dispersion in oil, 0.156 mmol). After 30 min, ethyl bromoacetate (0.017 mL, 0.156 mmol) was added and the mixture was stirred at ambient temperature for 67 h. NaOH (0.039 mL of a 10 M solution) was added and the mixture was stirred at ambient temperature for 16 h. The reaction mixture was filtered and purified directly by HPLC using a reversed phase C18 column and eluting with a gradient of $H_2O:CH_3CN:CF_3CO_2H$—90:10:0.1 to 5:95:0.1. Lyophilization provided the title compound. MS: m/z=289 (M+1).

INTERMEDIATE 49

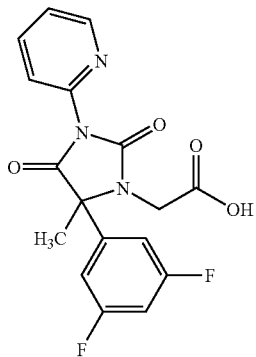

[5-(3,5-Difluorophenyl)-5-methyl-2,4-dioxo-3-pyridin-2-ylimidazolidin-1-yl]acetic acid, isomer A

Step A. Ethyl[5-(3,5-difluorophenyl)-5-methyl-2,4-dioxo-3-pyridin-2-ylimidazolidin-1-yl]acetate, isomer A A stirred solution of ethyl[5-(3,5-difluorophenyl)-5-methyl-2,4-dioxoimidazolidin-1-yl]acetate, isomer A (100 mg, 0.320 mmol, described in Intermediate 7), 2-bromopyridine (0.156 mL, 1.60 mmol), copper powder (71.2 mg, 1.12 mmol), copper (I) chloride (6.34 mg, 0.064 mmol), and potassium acetate (94.0 mg, 0.961 mmol) in pyridine (1.8 mL) was heated at 100° C. for 18 h. The cooled reaction mixture was poured onto 10% citric acid (20 mL) and with EtOAc (3×20 mL). The combined organic extracts were dried over $Na_2SO_4$, filtered and concentrated under reduced pressure. The crude product was purified by silica gel chromatography, eluting with a gradient of hexane:EtOAc—100:0 to 50:50, to provide the title compound. MS: m/z=390 (M+1).

Step B. [5-(3,5-Difluorophenyl)-5-methyl-2,4-dioxo-3-pyridin-2-ylimidazolidin-1-yl]acetic acid, isomer A To a stirred solution of ethyl[5-(3,5-difluorophenyl)-5-methyl-2,4-dioxo-3-pyridin-2-ylimidazolidin-1-yl]acetate, isomer A from Step A (67.0 mg, 0.172 mmol) in THF (2 mL) was added a solution of 1 N NaOH (0.516 mL, 0.516 mmol) and stirring continued for 16 h. The reaction mixture was diluted with DMSO (1 mL) and purified directly by HPLC using a reversed phase C18 column and eluting with a gradient of $H_2O:CH_3CN:CF_3CO_2H$—90:10:0.1 to 5:95:0.1. Lyophilization provided the racemic title compound. MS: m/z=362 (M+1).

INTERMEDIATE 50

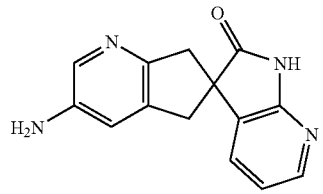

3-Amino-5,7-dihydrospiro[cyclopenta[b]pyridine-6,3'-pyrrolo[2,3-b]pyridin]-2'(1'H)-one, isomer A

Step A. 3,3-Diallyl-1-{[2-(trimethylsilyl)ethoxy]methyl}-1,3-dihydro-2H-pyrrolo[2,3-b]pyridin-2-one To a solution of 1-{[2-(trimethylsilyl)ethoxy]methyl}-1,3-dihydro-2H-pyrrolo[2,3-b]pyridin-2-one (1.00 g, 3.78 mmol, described in Intermediate 1) and cesium carbonate (3.70 g, 1.4 mmol) in DMF (10 mL) was added a solution of allyl bromide (0.720 mL, 8.32 mmol). After 6 h, the mixture was poured onto saturated $NaHCO_3$ (50 mL) and extracted with $CH_2Cl_2$ (3×30 mL). The combined organic layers were dried over $Na_2SO_4$, filtered, and concentrated in vacuo. The crude product was purified by silica gel chromatography, eluting with a gradient of hexane:EtOAc—100:0 to 50:50, to give the title compound. MS: m/z=345 (M+1).

Step B. 1'-{[2-(Trimethylsilyl)ethoxy]methyl}spiro[cyclopent-3-ene-1,3'-pyrrolo[2,3-b]pyridin]-2'(1'H)-one A mixture of 3,3-diallyl-1-{[2-(trimethylsilyl)ethoxy]methyl}-1,3-dihydro-2H-pyrrolo[2,3-b]pyridin-2-one from Step A (1.02 g, 2.96 mmol) and Grubbs second generation catalyst (37 mg, 0.045 mmol) in DCE (60 mL) was heated at reflux for 3.5 h. The mixture was concentrated in vacuo and purified by silica gel chromatography, eluting with a gradient of hexane:EtOAc—100:0 to 75:25, to give the title compound. MS: m/z=317 (M+1).

Step C. (±)-1'-{[2-(Trimethylsilyl)ethoxy]methyl}-3H-spiro[cyclopentane-1,3'-pyrrolo[2,3-b]pyridine]-2',3(1'H)-dione Borane-methyl sulfide complex (0.984 mL, 1.97 mmol, 2M in THF) was added drop wise to a solution of 1'-{[2-(trimethylsilyl)ethoxy]methyl}spiro[cyclopent-3-ene-1,3'-pyrrolo[2,3-b]pyridin]-2'(1'H)-one from Step B (208 mg, 0.656 mmol) in THF (3 mL) at 0° C. and the solution was slowly warmed to RT over 3.5 h. The reaction mixture was carefully quenched by the slow addition of water until hydrogen evolution ceased and then concentrated in vacuo. The resulting solid was dissolved in DMF (1 mL) and DCE (0.5 mL) and added drop wise to a suspension of PDC (740 mg, 1.97 mmol) in DCE (5 mL) at ambient temperature. The reaction mixture was heated at 65° C. for 21 h, with additional PDC (500 mg) added after 18 h. Celite was added to the reaction mixture until clumping occurred, and then it was diluted with Et$_2$O (50 mL). The mixture was filtered through a Celite plug, rinsing with additional Et$_2$O (4×50 mL) and the filtrate concentrated in vacuo. The crude product was purified by silica gel chromatography, eluting with a gradient of hexane:EtOAc—100:0 to 50:50, to give the title compound. MS: m/z=333 (M+1).

Step D. (±)-3-Nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of (±)-1'-{[2-(trimethylsilyl)ethoxy]methyl}-3H-spiro[cyclopentane-1,3'-pyrrolo[2,3-b]pyridine]-2',3(1'H)-dione from Step C (230 mg, 0.692 mmol) and 1-methyl-3,5-dinitropyridin-2(1H)-one (173 mg, 0.869 mmol, Tohda et. al., (1990) *Bull. Chem. Soc. Japan* 63(10), 2820-2827) in 2 M ammonia in MeOH (3.5 mL) was heated to reflux for 18 h. The mixture was concentrated in vacuo and purified by silica gel chromatography, eluting with a gradient of hexane:EtOAc—100:0 to 50:50, to give the title compound. MS: m/z=413 (M+1).

Step E. (±)-3-Amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of 10% Pd/C (20 mg) and (f)-3-nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step D (117 mg, 0.284 mmol) was stirred vigorously in MeOH (5 mL) under an atmosphere of hydrogen (ca. 1 atm). After 4.5 h, the mixture was filtered through a pad of Celite, washing extensively with MeOH, and the filtrate was concentrated in vacuo to give the title compound. MS: m/z=383 (M+1).

Step F. 3-Amino-5,7-dihydrospiro[cyclopenta[b]pyridine-6,3'-pyrrolo[2,3-b]pyridin]-2'(1'H)-one, isomer A A solution of (±)-3-amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step E (117 mg, 0.306 mmol) in MeOH (5 mL) was saturated with HCl (g). The mixture was stirred for 30 min and then concentrated in vacuo. The residue was dissolved in MeOH (3 mL) and treated with ethylenediamine (0.020 mL, 0.306 mmol) and 10 N sodium hydroxide to adjust the mixture to pH 10. After 1 h, the reaction mixture was purified directly by HPLC using a reversed phase. C18 column and eluting with a gradient of H$_2$O:CH$_3$CN:CF$_3$CO$_2$H—90:10:0.1 to 5:95:0.1. Lyophilization provided the racemic title compound as the TFA salt. The enantiomers were resolved by HPLC, utilizing a ChiralPak AD column and eluting with EtOH. The first major peak to elute was 3-amino-5,7-dihydrospiro[cyclopenta[b]pyridine-6,3'-pyrrolo[2,3-b]pyridin]-2'(1'H)-one, isomer A, the title compound, and the second major peak to elute was 3-amino-5,7-dihydrospiro[cyclopenta[b]pyridine-6,3'-pyrrolo[2,3-b]pyridin]-2'(1'H)-one, isomer B. MS: m/z=253 (M+1).

INTERMEDIATE 51

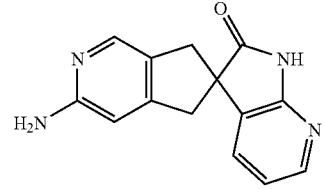

3-Amino-5,7-dihydrospiro[cyclopenta[c]pyridine-6,3'-pyrrolo[2,3-b]pyridin]-2'(1'H)-one, isomer A

Step A. 4,5-Bis(hydroxymethyl)pyridine-2-carbonitrile

To a solution of dimethyl 6-cyanopyridine-3,4-dicarboxylate (2.00 g, 9.08 mmol, Hashimoto et al. (1997) *Heterocycles* 46, 581) in EtOH (50 mL) was added lithium borohydride (4.54 mL of a 2 M solution in THF, 9.08 mmol) drop wise. The reaction mixture was stirred at ambient temperature for 3 h, and then cooled to 0° C. Saturated aqueous NaHCO$_3$ (20 mL) was added slowly and the quenched mixture was extracted with EtOAc (9×100 mL). The combined organic extracts were dried over Na$_2$SO$_4$, filtered, and concentrated in vacuo. The crude product was purified by silica gel chromatography, eluting with a gradient of CH$_2$Cl$_2$:MeOH—100:0 to 85:15, to give the title compound. MS: m/z=165 (M+1).

Step B. 4,5-Bis(bromomethyl)pyridine-2-carbonitrile

To a solution of 4,5-bis(hydroxymethyl)pyridine-2-carbonitrile from Step A (750 mg, 4.57 mmol) in THF (15 mL) was added phosphorus tribromide (1.61 g, 5.94 mmol) in THF (5 mL) drop wise. The reaction mixture was stirred at ambient temperature for 2 h, and then cooled to 0° C. Saturated aqueous NaHCO$_3$ (5 mL) was added slowly and the quenched mixture was extracted with CHCl$_3$ (2×30 mL). The combined organic extracts were dried over Na$_2$SO$_4$, filtered, and concentrated in vacuo. The crude product was purified by silica gel chromatography, eluting with a gradient of hexane: EtOAc—100:0 to 25:75, to give the title compound. MS: m/z=291 (M+1).

Step C. (±)-2'-Oxo-1',2',5,7-tetrahydrospiro[cyclopenta[c]pyridine-6,3'-pyrrolo[2,3-b]pyridine]-3-carbonitrile To a solution of 4,5-bis(bromomethyl)pyridine-2-carbonitrile from Step B (2.56 g, 8.83 mmol) and 1,3-dihydro-2H-pyrrolo[2,3-b]pyridin-2-one (1.18 g, 8.83 mmol, Marfat et al (1987) *Tetrahedron Lett*. 28, 4027) in THF (120 mL) and H$_2$O (60 mL) was added lithium hydroxide monohydrate (1.11 g, 26.5 mmol). After 20 min, the reaction mixture was poured onto water (100 mL) and extracted with EtOAc (3×100 mL). The combined organic extracts were dried over Na$_2$SO$_4$, filtered, and concentrated in vacuo. The crude product was purified by silica gel chromatography, eluting with a gradient of CH$_2$Cl$_2$:MeOH:NH$_4$OH—100:0:0 to 95:5:1, to give the title compound. MS: m/z=263 (M+1).

Step D. (±)-Sodium 2'-oxo-1',2',5,7-tetrahydrospiro [cyclopenta[c]pyridine-6,3'-pyrrolo[2,3-b]pyridine]-3-carboxylate To a solution of (±)-2'-oxo-1',2',5,7-tetrahydrospiro[cyclopenta[c]pyridine-6,3'-pyrrolo[2,3-b]pyridine]-3-carbonitrile from Step C (1.53 g, 5.83 mmol) in EtOH (20 mL) was added 5M aqueous NaOH (3.50 mL). The mixture was heated at reflux for 3 d, with additional 5M aqueous NaOH (2.00 mL) added at 6 h. The reaction mixture was allowed to cool and was concentrated to dryness in vacuo to afford the title compound in sufficient purity for use in subsequent steps. MS: m/z=282 (M+1).

Step E. (±)-tert-Butyl (2'-oxo-1',2',5,7-tetrahydrospiro[cyclopenta[c]pyridine-6,3'-pyrrolo[2,3-b] pyridin]-3-yl)carbamate To a suspension of (±)-sodium 2'-oxo-1',2',5,7-tetrahydrospiro[cyclopenta[c]pyridine-6,3'-pyrrolo[2,3-b]pyridine]-3-carboxylate from Step D (1.64 g, 5.83 mmol) and triethylamine (1.62 mL, 11.7 mmol) in tert-butanol (50 mL) was added diphenylphosphoryl azide (1.89 mL, 8.75 mmol) and the mixture was heated at reflux for 72 h. Additional diphenylphosphoryl azide (1.89 mL, 8.75 mmol) was added at 24 and 56 h. The reaction mixture was concentrated in vacuo and then partitioned between CH$_2$Cl$_2$ (75 mL) and saturated NaHCO$_3$ (100 mL). The organic layer was separated and the aqueous layer was further extracted with CH$_2$Cl$_2$ (2×50 mL). The combined organic layers were dried over Na$_2$SO$_4$, filtered, and concentrated in vacuo. The crude product was purified by silica gel chromatography, eluting with a gradient of CH$_2$Cl$_2$:MeOH:NH$_4$OH—100:0:0 to 95:5:1, to give the title compound. MS: m/z=353 (M+1).

Step F. 3-Amino-5,7-dihydrospiro[cyclopenta[c] pyridine-6,3'-pyrrolo[2,3-b]pyridin]-2'(1'H)-one, isomer A A solution of (±)-tert-butyl (2'-oxo-1',2',5,7-tetrahydrospiro[cyclopenta[c]pyridine-6,3'-pyrrolo[2,3-b]pyridin]-3-yl)carbamate from Step E (1.39 g, 3.94 mmol) was stirred in CH$_2$Cl$_2$ (10 mL) and TFA (3 mL) for 18 h and then concentrated in vacuo to provide the racemic title compound as the TFA salt. The enantiomers were resolved by HPLC, utilizing a ChiralPak AD column and eluting with MeOH. The first major peak to elute was 3-amino-5,7-dihydrospiro[cyclopenta[c]pyridine-6,3'-pyrrolo[2,3-b]pyridin]-2'(1'11)-one, isomer A, the title compound, and the second major peak to elute was 3-amino-5,7-dihydrospiro[cyclopenta[c]pyridine-6,3'-pyrrolo[2,3-b]pyridin]-2'(1'11)-one, isomer B. MS: m/z=253 (M+1).

INTERMEDIATE 52

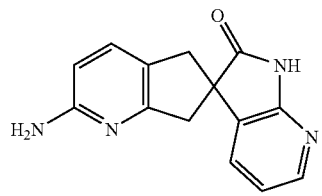

(±)-2-Amino-5,7-dihydrospiro[cyclopenta[b]pyridine-6,3'-pyrrolo[2,3-b]pyridin]-2'(1'11)-one Step A. Dimethyl 6-cyanopyridine-2,3-dicarboxylate To a solution of dimethylpyridine-2,3-dicarboxylate 1-oxide (15.3 g, 72.5 mmol, Niiyami et al. (2002) *Bioorg. Med. Chem. Lett*. 12, 3041) and trimethylsilyl cyanide (15.7 mL, 117 mmol) in DME (161 mL) was added dimethylcarbamoyl chloride (10.5 mL, 114 mmol). The reaction mixture was heated at reflux for 3 d, and then cooled to 0° C. Saturated aqueous NaHCO$_3$ (800 mL) was added slowly and the quenched mixture was extracted with EtOAc (2×1000 mL). The combined organic extracts were washed with brine (200 mL), dried over Na$_2$SO$_4$, filtered, and concentrated in vacuo. The crude product was purified by silica gel chromatography, eluting with a gradient of hexane:EtOAc—100:0 to 50:50, to give the title compound. MS: m/z=221 (M+1).

Step B. 5,6-Bis(hydroxymethyl)pyridine-2-carbonitrile

To a solution of dimethyl 6-cyanopyridine-2,3-dicarboxylate from Step A (13.0 g, 59.0 mmol) in EtOH (295 mL) was added lithium borohydride (29.5 mL of a 2 M solution in THF, 59.0 mmol) drop wise. The reaction mixture was stirred at ambient temperature for 4 h, and then cooled to 0° C. Saturated aqueous NaHCO$_3$ (200 mL) was added slowly and the quenched mixture was extracted with EtOAc (9×100 mL). The combined organic extracts were dried over Na$_2$SO$_4$, filtered, and concentrated in vacuo. The crude product was purified by silica gel chromatography, eluting with a gradient of CH$_2$Cl$_2$:MeOH—100:0 to 85:15, to give the title compound. MS: m/z=165 (M+1).

Step C. 5,6-Bis(bromomethyl)pyridine-2-carbonitrile

To a solution of 5,6-bis(hydroxymethyl)pyridine-2-carbonitrile from Step B (2.50 g, 15.2 mmol) in THF (76 mL) was added phosphorus tribromide (5.36 g, 19.8 mmol) in THF (20 mL) drop wise. The reaction mixture was stirred at ambient temperature for 2 h, and then cooled to 0° C. Saturated aqueous NaHCO₃ (20 mL) was added slowly and the quenched mixture was extracted with CH₂Cl₂ (2×200 mL) The combined organic extracts were dried over Na₂SO₄, filtered, and concentrated in vacuo. The crude product was purified by silica gel chromatography, eluting with a gradient of hexane: EtOAc—100:0 to 30:70, to give the title compound. MS: m/z=291 (M+1).

Step D. (±)-2'-Oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile To a solution of 5,6-bis(bromomethyl)pyridine-2-carbonitrile from Step C (1.80 g, 6.21 mmol) and 1-{[2-(trimethylsilyl)ethoxy]methyl}-1,3-dihydro-2H-pyrrolo[2,3-b]pyridin-2-one (1.64 g, 6.21 mmol, described in Intermediate 1) in DMF (207 mL) was added cesium carbonate (6.07 g, 18.6 mmol), portionwise, over 5 min. After 18 h, the mixture was partitioned between CH₂Cl₂ (100 mL), saturated aqueous NaHCO₃ (100 mL) and brine (200 mL). The organic layer was removed and the aqueous layer was extracted further with CH₂Cl₂ (2×100 mL). The combined organic extracts were dried over Na₂SO₄, filtered, and concentrated in vacuo. The crude product was purified by silica gel chromatography, eluting with a gradient of hexane:EtOAc—100:0 to 10:90, to give the title compound. MS: m/z=393 (M+1).

Step E. (±)-2'-Oxo-1',2',5,7-tetrahydrospiro[cyclopenta[b]pyridine-6,3'-pyrrolo[2,3-b]pyridine]-2-carboxylic acid To a solution of (±)-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile from Step D (690 mg, 1.76 mmol) in THF (5 mL) was added 3 N aqueous HCl (36 mL). The mixture was heated at reflux for 18 h, allowed to cool and concentrated to dryness in vacuo. The reaction mixture was dissolved in water (12 ml) and purified directly by HPLC using a reversed phase C18 column and eluting with a gradient of H₂O:CH₃CN:CF₃CO₂H—95:5:0.1 to 5:95:0.1. Lyophilization provided the title compound. MS: m/z=282 (M+1).

Step F. (±)-tert-Butyl (2'-oxo-1',2',5,7-tetrahydrospiro[cyclopenta[b]pyridine-6,3'-pyrrolo[2,3-b]pyridin]-2-yl)carbamate To a suspension of (±)-2'-oxo-1',2',5,7-tetrahydrospiro[cyclopenta[b]pyridine-6,3'-pyrrolo[2,3-b]pyridine]-2-carboxylic acid from Step E (224 mg, 0.796 mmol) and triethylamine (0.333 mL, 2.39 mmol) in tert-butanol (5 mL) was added diphenylphosphoryl azide (0.258 mL, 1.20 mmol) and the mixture was heated at reflux for 1 h. The reaction mixture was concentrated in vacuo and then partitioned between CH₂Cl₂ (20 mL) and saturated NaHCO₃ (20 mL). The organic layer was separated and the aqueous layer was further extracted with CH₂Cl₂ (2×20 mL). The combined organic layers were dried over Na₂SO₄, filtered, and concentrated in vacuo. The crude product was purified by silica gel chromatography, eluting with a gradient of CH₂Cl₂:MeOH: NH₄OH—100:0:0 to 95:5:1, to give the title compound. MS: m/z=353 (M+1).

Step G. (±)-2-Amino-5,7-dihydrospiro[cyclopenta[b]pyridine-6,3'-pyrrolo[2,3-b]pyridin]-2'(1'H)-one A solution of (±)-tert-butyl (2'-oxo-1',2',5,7-tetrahydrospiro[cyclopenta[b]pyridine-6,3'-pyrrolo[2,3-b]pyridin]-2-yl)carbamate from Step F (147 mg, 0.417 mmol) was stirred in CH₂Cl₂ (6 mL) and TFA (1 mL) for 3 h and then concentrated in vacuo to provide the title compound as the TFA salt. MS: m/z=253 (M+1).

Example 1

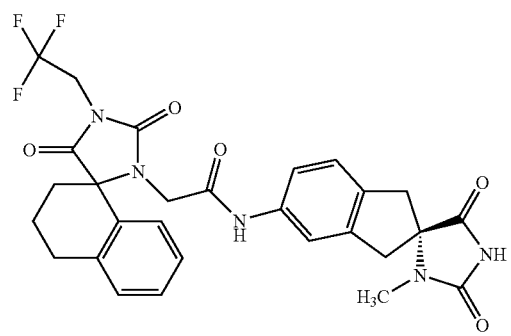

2-[2,5-Dioxo-1-(2,2,2-trifluoroethyl)-3',4'-dihydro-2'H,3H-spiro[imidazolidine-4,1'-naphthalen]-3-yl]-N-[(4S)-3-methyl-2,5-dioxo-1',3'-dihydrospiro[imidazolidine-4,2'-inden]-5'-yl]acetamide diastereomer B A solution of [2,5-dioxo-1-(2,2,2-trifluoroethyl)-3',4'-dihydro-2'H,3H-spiro[imidazolidine-4,1'-naphthalen]-3-yl] acetic acid, isomer B (100 mg, 0.281 mmol, described in Intermediate 32), HOBt (64.0 mg, 0.421 mmol) and (4S)-5'-amino-3-methyl-1',3'-dihydro-2H,5H-spiro[imidazolidine-4,2'-indene]-2,5-dione (65.0 mg, 0.281 mmol, prepared according to Bell, I. M., et al., PCT Int. Appl., WO 2004082605 A2), EDC (81.0 mg, 0.421 mmol), and N,N-diisopropylethylamine (0.244 mL, 1.40 mmol) in DMF (2 mL) was stirred at 50° C. for 2 h. The reaction mixture was purified directly by HPLC using a reversed phase C18 column and eluting with a gradient of H₂O:CH₃CN:CF₃CO₂H—90:10:0.1 to 5:95:0.1. Lyophilization provided the title compound. MS: m/z=570 (M+1). HRMS: m/z=570.1954; calculated m/z=570.1959 for C₂₈H₂₇F₃N₅O₅.

Examples 2-6

Essentially following the procedures outlined for Example 1, the compounds listed in Table 3 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 3

| Example | R^b | MS (M+1) | Stereochemistry of Acid | Acid Intermediate |
|---|---|---|---|---|
| 2 | (2,2,2-trifluoroethyl-hydantoin-spiroindane) | 556 | A | 28 |
| 3 | (2,2,2-trifluoroethyl-hydantoin-spiro-difluoroindane) | 592 | A | 36 |
| 4 | (2,2,2-trifluoroethyl-hydantoin-spiro-fluoroindane) | 574 | A | 37 |
| 5 | (2,2,2-trifluoroethyl-hydantoin-spiro-fluoroindane) | 574 | A | 34 |
| 6 | (isopropyl-dioxo-tetrahydropyrimidine-phenyl) | 504 | S | 5 |

Example 7

N-(2',5'-Dioxo-1,3-dihydrospiro[indene-2,3'-pyrrolidine]-5-yl)-2-[2,5-dioxo-1-(2,2,2-trifluoroethyl)-3',4'-dihydro-2'H,3H-spiro[imidazolidine-4,1'-naphthalen]-3-yl]acetamide, diastereomer B A mixture of [2,5-dioxo-1-(2,2,2-trifluoroethyl)-3',4'-dihydro-2'H,3H-spiro[imidazolidine-4,1'-naphthalen]-3-yl] acetic acid, isomer B (70.0 mg, 0.196 mmol, described in Intermediate 32), (+)-5-amino-1,3-dihydro-2'H,5'H-spiro[indene-2,3'-pyrrolidine]-2',5'-dione (42.5 mg, 0.196 mmol, described in Intermediate 4), HOBT (45.1 mg, 0.295 mmol), EDC (56.5 mg, 0.295 mmol), and N,N-diisopropylethylamine (0.172 mL, 0.982 mmol) in DMF (1 mL) was stirred at 50° C. for 2 h. The reaction mixture was diluted with water (10 mL) and extracted with EtOAc (3×10 mL). The combined organic layers were washed with $H_2O$ (10 mL), dried over $MgSO_4$, filtered, and concentrated under reduced pressure. The crude product was purified by silica gel chromatography, eluting with $CH_2Cl_2$:MeOH:$NH_4OH$—100:0:0 to 95:5:0.1, to give the title compound. MS: m/z=555 (M+1). HRMS: m/z=555.1845; calculated m/z=555.1850 for $C_{28}H_{25}F_3N_4O_5$.

Example 8

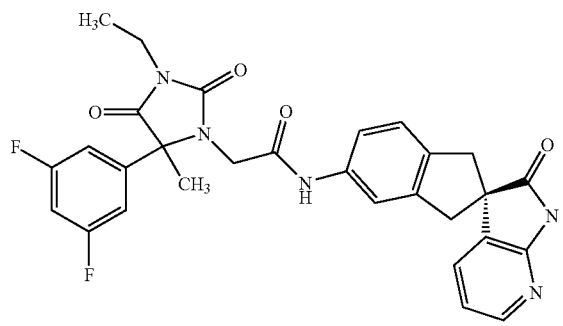

2-[5-(3,5-Difluorophenyl)-3-ethyl-5-methyl-2,4-dioxoimidazolidin-1-yl]-N-[(2R)-2'-oxo-1,1',2',3-tetrahydrospiro[indene-2,3'-pyrrolo[2,3-b]pyridin]-5-yl]acetamide, diastereomer A A mixture of [5-(3,5-difluorophenyl)-5-methyl-2,4-dioxo-3-ethylimidazolidin-1-yl]acetic acid, isomer A (18 mg, 0.058 mmol, described in Intermediate 17), (R)-5-amino-1,3-dihydrospiro[indene-2,3'-pyrrolo[2,3-b]pyridin]-2'(1'H)-one (14 mg, 0.058 mmol, described in Intermediate 3), HOBT (13 mg, 0.086 mmol), EDC (17 mg, 0.086 mmol), and N,N-diisopropylethylamine (0.050 mL, 0.29 mmol) in DMF (0.5 mL) was stirred at 50° C. for 2 h. The reaction mixture was purified directly by HPLC using a reversed phase C18 column and eluting with a gradient of $H_2O:CH_3CN:CF_3CO_2H$—90:10:0.1 to 5:95:0.1. Lyophilization provided the title compound. MS: m/z=546 (M+1). HRMS: m/z=546.1944; calculated m/z=546.1948 for $C_{29}H_{26}F_2N_5O_4$.

Examples 9-53

Essentially following the procedures outlined for Example 8, the compounds listed in Table 4 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 4

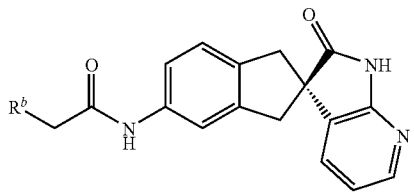

| Example | $R^b$ | MS (M + 1) | Stereochemistry of $R^b$ | Acid Intermediate |
|---|---|---|---|---|
| 9 | 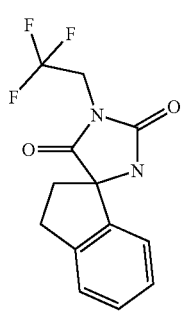 | 576 | ± | 27 |
| 10 | 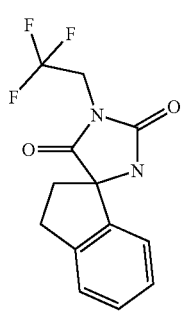 | 576 | A | 28 |
| 11 | 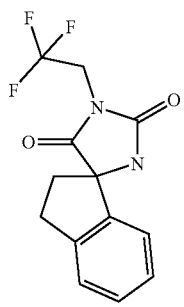 | 576 | B | 29 |
| 12 |  | 590 | ± | 30 |
| 13 | 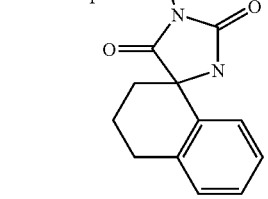 | 590 | A | 31 |

TABLE 4-continued

| Example | R^b | MS (M+1) | Stereochemistry of R^b | Acid Intermediate |
|---|---|---|---|---|
| 14 | | 590 | B | 32 |
| 15 | | 604 | ± | 42 |
| 16 | | 592 | ± | 40 |
| 17 | | 610 | ± | 41 |
| 18 | | 592 | ± | 35 |
| 19 | | 592 | A | 36 |
| 20 | | 594 | A | 37 |
| 21 | | 594 | ± | 33 |

TABLE 4-continued

| Example | R^b | MS (M+1) | Stereochemistry of R^b | Acid Intermediate |
|---|---|---|---|---|
| 22 | (2,2,2-trifluoroethyl-substituted spiro[indane-1,4'-imidazolidine]-2',5'-dione with 6-F) | 594 | A | 34 |
| 23 | (2,2,2-trifluoroethyl-substituted spiro[indane-1,4'-imidazolidine]-2',5'-dione with 6-F) | 594 | ± | 38 |
| 24 | (isopropyl-substituted spiro[indane-1,4'-imidazolidine]-2',5'-dione) | 536 | A | 39 |
| 25 | (isopropyl-substituted 4-phenyl-dihydropyrimidine-2,6-dione) | 504 | ± | 8 |

| Example | R^b | MS (M+1) | Stereochemistry of R^b | Acid Intermediate |
|---|---|---|---|---|
| 26 | (isopropyl-substituted 4-phenyl-dihydropyrimidine-2,6-dione) | 504 | S | 5 |
| 27 | (isopropyl-substituted 5-methyl-5-phenyl-imidazolidine-2,4-dione) | 524 | ± | 13 |
| 28 | (isopropyl-substituted 5-methyl-5-phenyl-imidazolidine-2,4-dione) | 524 | A | 14 |
| 29 | (isopropyl-substituted 5-methyl-5-phenyl-imidazolidine-2,4-dione) | 524 | B | 6 |

TABLE 4-continued

| Example | $R^b$ | MS (M + 1) | Stereo-chemistry of $R^b$ | Acid Intermediate |
|---|---|---|---|---|
| 30 | (2,2,2-trifluoroethyl)-methyl-phenyl hydantoin | 564 | ± | 15 |
| 31 | (2,2,2-trifluoroethyl)-methyl-phenyl hydantoin | 564 | A | 16 |
| 32 | (2,2,2-trifluoroethyl)-methyl-phenyl hydantoin | 564 | B | 17 |
| 33 | (2,2,2-trifluoroethyl)-cyclobutyl-phenyl hydantoin | 604 | ± | 9 |
| 34 | (2,2,2-trifluoroethyl)-ethyl-phenyl hydantoin | 578 | ± | 10 |
| 35 | (2,2,2-trifluoroethyl)-methyl-(3,5-difluorophenyl) hydantoin | 600 | ± | 19 |
| 36 | (2,2,2-trifluoroethyl)-methyl-(3,5-difluorophenyl) hydantoin | 600 | A | 20 |
| 37 | (2,2,2-trifluoroethyl)-methyl-(3,5-difluorophenyl) hydantoin | 600 | B | 21 |

TABLE 4-continued
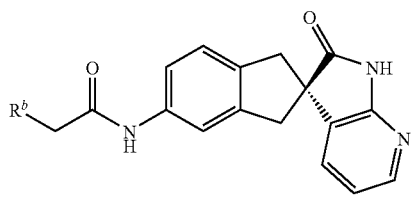
| Example | $R^b$ | MS (M + 1) | Stereochemistry of $R^b$ | Acid Intermediate |
|---|---|---|---|---|
| 38 | 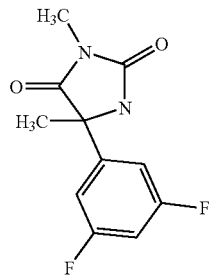 | 532 | A | 18 |
| 39 | 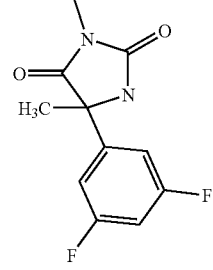 | 560 | A | 22 |
| 40 | 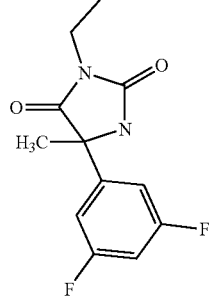 | 560 | A | 23 |
| 41 | 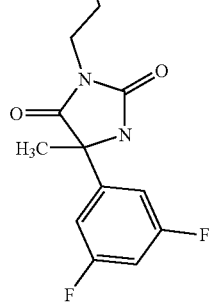 | 564 | A | 24 |
TABLE 4-continued
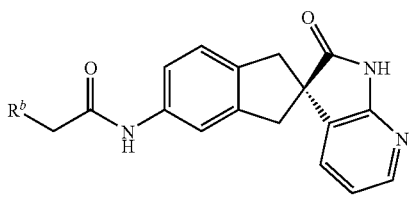
| Example | $R^b$ | MS (M + 1) | Stereochemistry of $R^b$ | Acid Intermediate |
|---|---|---|---|---|
| 42 | 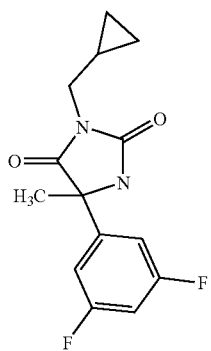 | 572 | A | 25 |
| 43 | 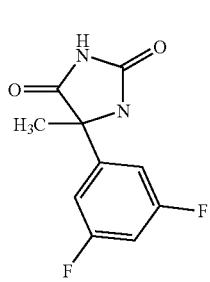 | 518 | A | 7 |
| 44 | 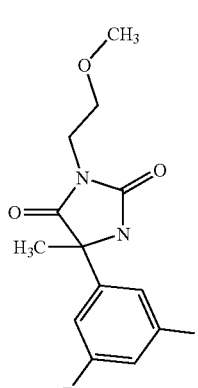 | 576 | A | 26 |
| 45 | 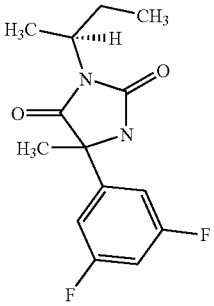 | 574 | B | 45 |

TABLE 4-continued

| Example | R^b | MS (M + 1) | Stereochemistry of R^b | Acid Intermediate |
|---|---|---|---|---|
| 46 | (structure) | 574 | B | 44 |
| 47 | (structure) | 522 | ± | 48 |
| 48 | (structure) | 556 | none | 11 |
| 49 | (structure) | 562 | A | 46 |
| 50 | (structure) | 576 | None | 12 |
| 51 | (structure) | 595 | A | 49 |
| 52 | (structure) | 562 | A | 47 |
| 53 | (structure) | 510 | ± | 43 |

Example 54

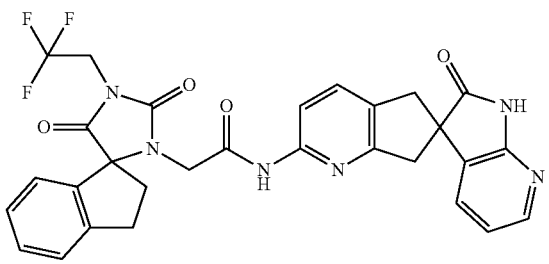

2-[2,5-Dioxo-1-(2,2,2-trifluoroethyl)-2',3'-dihydro-3H-spiro[imidazolidine-4,1'-inden]-3-yl]-N-(2'-oxo-1',2',5,7-tetrahydrospiro[cyclopenta[b]pyridine-6,3'-pyrrolo[2,3-b]pyridin]-2-yl)acetamide, diastereomer A A mixture of [2,5-dioxo-1-(2,2,2-trifluoroethyl)-2',3'-dihydro-3H-spiro[imidazolidine-4,1'-inden]-3-yl]acetic acid, isomer A (14 mg, 0.042 mmol, described in Intermediate 28), (±)-3-amino-5,7-dihydrospiro[cyclopenta[b]pyridine-6,3'-pyrrolo[2,3-b]pyridin]-2'(1'H)-one (20 mg, 0.042 mmol, described in Intermediate 52), PyClu (18 mg, 0.050 mmol), and N,N N-diisopropylethylamine (0.036 mL, 0.21 mmol) in THF (1 mL) was stirred at ambient temperature for 16 h. The reaction mixture was purified directly by HPLC using a reversed phase C18 column and eluting with a gradient of $H_2O:CH_3CN:CF_3CO_2H$—90:10:0.1 to 5:95:0.1. Lyophilization provided the title compound as the TFA salt. MS: m/z=577 (M+1). HRMS: m/z=577.1814; calculated m/z=577.1806 for $C_{29}H_{23}F_3N_6O_4$.

Example 55

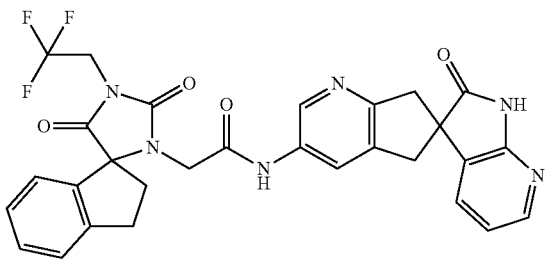

2-[2,5-Dioxo-1-(2,2,2-trifluoroethyl)-2',3'-dihydro-3H-spiro[imidazolidine-4,1'-inden]-3-yl]-N-(2'-oxo-1',2',5,7-tetrahydrospiro[cyclopenta[b]pyridine-6,3'-pyrrolo[2,3-b]pyridin]-3-yl)acetamide, diastereomer A

[2,5-dioxo-1-(2,2,2-trifluoroethyl)-2',3'-dihydro-3H-spiro[imidazolidine-4,1'-inden]-3-yl]acetic acid, isomer A (30 mg, 0.087 mmol, described in Intermediate 28), 3-amino-5,7-dihydrospiro[cyclopenta[b]pyridine-6,3'-pyrrolo[2, 3-1)]pyridin]-2'(1'H)-one, isomer A (25 mg, 0.087 mmol, described in Intermediate 50), HATU (36 mg, 0.095 mmol), and N-methylmorpholine (0.048 mL, 0.43 mmol) in DMF (1 mL) was stirred at ambient temperature for 16 h. The reaction mixture was diluted with saturated NaHCO$_3$ (10 mL) and extracted with CH$_2$Cl$_2$ (3×10 mL). The combined organic layers were dried over NaSO$_4$, filtered, and concentrated under reduced pressure. The crude product was purified by silica gel chromatography, eluting with CH$_2$Cl$_2$:MeOH:NH$_4$OH—100:0:0 to 90:10:0.1, to give the title compound. MS: m/z=577 (M+1). HRMS: m/z=577.1825; calculated m/z=577.1806 for $C_{29}H_{23}F_3N_6O_4$.

Example 56

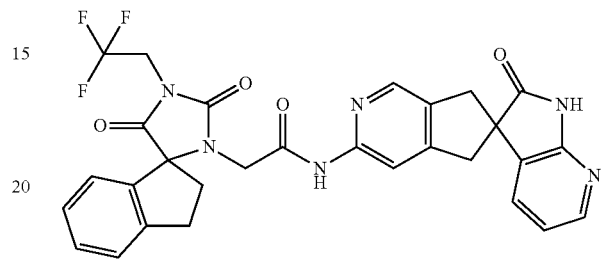

2-[2,5-Dioxo-1-(2,2,2-trifluoroethyl)-2',3'-dihydro-3H-spiro[imidazolidine-4,1'-inden]-3-yl]-N-(2'-oxo-1',2',5,7-tetrahydrospiro[cyclopenta[c]pyridine-6,3'-pyrrolo[2,3-b]pyridin]-3-yl)acetamide, diastereomer A

[2,5-dioxo-1-(2,2,2-trifluoroethyl)-2',3'-dihydro-3H-spiro[imidazolidine-4,1'-inden]-3-yl]acetic acid, isomer A (50 mg, 0.15 mmol, described in Intermediate 28), 3-amino-5,7-dihydrospiro[cyclopenta[c]pyridine-6,3'-pyrrolo[2,3-b]pyridin]-2'(1'H)-one, isomer A (37 mg, 0.15 mmol, described in Intermediate 51), chloro-N,N,N',N'-tetramethylformamidinium hexafluorophosphate (45 mg, 0.16 mmol), and N-methylmorpholine (0.048 mL, 0.44 mmol) in DMF (1 mL) was stirred at ambient temperature for 2.5 h. The reaction mixture was diluted with saturated water (10 mL) and extracted with CH$_2$Cl$_2$ (3×10 mL). The combined organic layers were dried over NaSO$_4$, filtered, and concentrated under reduced pressure. The crude product was purified by silica gel chromatography, eluting with CH$_2$Cl$_2$:MeOH:NH$_4$OH—100:0:0 to 95:5:0.1, to give the title compound. MS: m/z=577 (M+1). HRMS: m/z=577.1818; calculated m/z=577.1806 for $C_{29}H_{23}F_3N_6O_4$.

It will be appreciated by those with skill in the art that analogous compounds may be prepared using the other intermediates described herein, following the procedures outlined in Example 1 or other procedures ascertainable without undue experimentation.

What is claimed is:
1. A compound of the formula I:

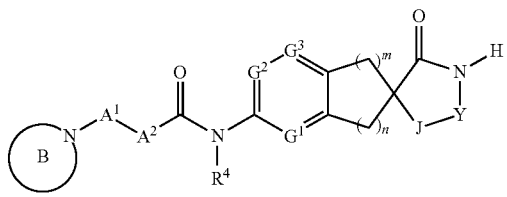

wherein:
B is a heterocycle selected from the group consisting of:

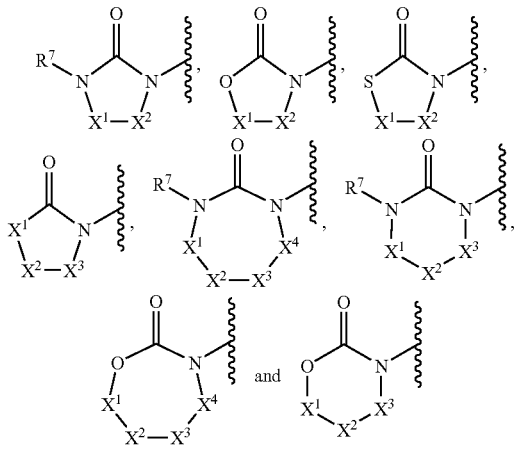

wherein $X^1$, $X^2$, $X^3$ and $X^4$ are each carbon, and one of $X^1$, $X^2$, $X^3$ and $X^4$ present on B is spirally substituted to form a ring or ring system selected from:
  indanyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, 2,3,4,5-tetrahydro-1-benzoxepinyl, 2,3,4,5-tetrahydro-1H-1-benzazepinyl, 2,3,4,5-tetrahydro-1-benzothiepinyl, 1,3,4,5-tetrahydro-2-benzoxepinyl, 2,3,4,5-tetrahydro-1H-2-benzazepinyl, 1,3,4,5-tetrahydro-2-benzothiepinyl, 1,2,4,5-tetrahydro-3-benzoxepinyl, 2,3,4,5-tetrahydro-1H-3-benzazepinyl, 1,2,4,5-tetrahydro-3-benzothiepinyl, cycloheptyl, morpholinyl, tetrahydropyranyl, tetrahydrofuranyl, thiepanyl, oxepanyl and azepanyl,
  which ring or ring system is unsubstituted or substituted with one or more substituents each independently selected from:
    (a) —$C_{1-6}$alkyl, which is unsubstituted or substituted with 1-3 substituents where the substituents are independently selected from: halo, hydroxy, —$OC_{1-6}$alkyl, —$C_{3-6}$cycloalkyl, —$CO_2R^9$, —$NR^{10}R^{11}$, —$SO_2R^{12}$, —$CONR^{10a}R^{11a}$, phenyl and heterocycle, wherein said heterocycle is selected from: pyridyl, pyrimidinyl, pyrazinyl, pyridazinyl, piperidinyl, piperazinyl, pyrrolidinyl, thienyl, and morpholinyl,
    (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{3-6}$cycloalkyl, —$C_{1-6}$alkyl (which is unsubstituted or substituted with 1-6 fluoro), and —$OC_{1-6}$alkyl (which is unsubstituted or substituted with 1-6 fluoro, halo, or hydroxyl),
    (c) —$SO_2R^{12}$,
    (d) hydroxy,
    (e) —$OC_{1-6}$alkyl, which is unsubstituted or substituted with 1-5 halo,
    (f) —$COR^{12}$,
    (g) —$NR^{10}R^{11}$,
    (h) halo,
    (i) —CN,
    (j) —$CONR^{10a}R^{11a}$,
    (k) oxo, and
    (l) —$C_{3-6}$cycloalkyl,
  and wherein the remaining members of the group $X^1$, $X^2$, $X^3$ and $X^4$ present on B are each independently unsubstituted or substituted with one or two substituents selected from $R^1$ and $R^2$, where:
  $R^1$ and $R^2$ are each independently selected from:
    (1) —$C_{1-6}$alkyl, which is unsubstituted or substituted with 1-7 substituents each independently selected from:
      (a) halo,
      (b) hydroxy,
      (c) —O—$C_{1-6}$alkyl,
      (d) —$C_{3-6}$cycloalkyl,
      (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
      (f) —$CO_2R^9$, and
      (g) —$CONR^{10a}R^{11a}$;
    (2) —$C_{3-6}$cycloalkyl, which is unsubstituted or substituted with 1-7 substituents each independently selected from: halo, hydroxy, —$OC_{1-6}$alkyl, trifluoromethyl and phenyl,
    (3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
      (a) —$C_{1-6}$alkyl, which is unsubstituted or substituted with 1-6 fluoro,
      (b) halo,
      (c) hydroxy,
      (d) —$OC_{1-6}$alkyl, which is unsubstituted or substituted with 1-6 fluoro,
      (e) —$C_{3-6}$cycloalkyl,
      (f) phenyl which is unsubstituted or substituted with 1-5 substituents each independently selected from: —$C_{1-6}$alkyl, —O—$C_{1-6}$alkyl, halo, hydroxyl and trifluoromethyl,
      (g) —$CO_2R^9$,
      (h) —$NR^{10}R^{11}$;
      (i) —$CONR^{10a}R^{11a}$, and
      (j) —$SO_2R^{12}$;
    (4) halo,
    (5) hydroxy,
    (6) —$OC_{1-6}$alkyl, which is unsubstituted or substituted with 1-5 halo,
    (7) —CN,
    (8) —$CO_2R^9$,
    (9) —$NR^{10}R^{11}$;
    (10) —$SO_2R^{12}$, and
    (11) —$CONR^{10a}R^{11a}$;
  or, wherein $X^1$, $X^2$, $X^3$ and $X^4$ are each carbon, and one of $X^1$, $X^2$, $X^3$ and $X^4$ present on B is —(C=O)—, wherein another one of the members of the group $X^1$, $X^2$, $X^3$ and $X^4$ present on B is optionally spirally substituted to form a ring or ring system selected from:
cyclopropyl, cyclobutyl, cyclopentyl, cyclohexyl, cycloheptyl, cyclooctyl, indanyl, azetidinyl, pyrrolidinyl, piperidinyl, piperazinyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, 2,3,4,5-tetrahydro-1-benzoxepinyl, 2,3,4,5-tetrahydro-1H-1-benzazepinyl, 2,3,4,5-tetrahydro-1-benzothiepinyl, 1,3,4,5-tetrahydro-2-benzoxepinyl, 2,3,4,5-tetrahydro-1H-2-benzazepinyl, 1,3,4,5-tetrahydro-2-benzothiepinyl, 1,2,4,5-tetrahydro-3-benzoxepinyl, 2,3,4,5-tetrahydro-1H-3-benzazepinyl, 1,2,4,5-tetrahydro-3-benzothiepinyl, morpholinyl, tetrahydropyranyl, tetrahydrofuranyl, thiepanyl, oxepanyl and azepanyl, which ring or ring system is unsubstituted or substituted with one or more substituents each independently selected from:
  (a) —$C_{1-6}$alkyl, which is unsubstituted or substituted with 1-3 substituents where the substituents are independently selected from: halo, hydroxy, —$OC_{1-6}$alkyl, —$C_{3-6}$cycloalkyl, —$CO_2R^9$, —$NR^{10}R^{11}$, —$SO_2R^{12}$, —$CONR^{10a}R^{11a}$ phenyl and heterocycle, wherein said heterocycle is selected from: pyridyl, pyrimidinyl, pyrazinyl, pyridazinyl, piperidinyl, piperazinyl, pyrrolidinyl, thienyl, and morpholinyl,
  (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{3-6}$cycloalkyl, —$C_{1-6}$alkyl (which is unsubstituted or substituted with 1-6 fluoro), and —$OC_{1-6}$alkyl (which is unsubstituted or substituted with 1-6 fluoro, halo, or hydroxyl),
  (c) —$SO_2R^{12}$,
  (d) hydroxy,
  (e) —$OC_{1-6}$alkyl, which is unsubstituted or substituted with 1-5 halo,
  (f) —$COR^{12}$,
  (g) —$NR^{10}R^{11}$,
  (h) halo,
  (i) —CN,
  (j) —$CONR^{10a}R^{11a}$,
  (k) oxo, and
  (l) —$C_{3-6}$cycloalkyl, and wherein the remaining members of the group $X^1$, $X^2$, $X^3$ and $X^4$ present on B are each independently unsubstituted or substituted with one or more substituents selected from $R^1$ and $R^2$ as defined, $A^1$ and $A^2$ are each independently selected from:
  (1) a bond, and
  (2) —$CR^{13}R^{14}$—,
wherein one of $A^1$ and $A^2$ is optionally absent;

$G^1$, $G^2$, and $G^3$ are each independently selected from:
  (1) —C($R^5$)=,
  (2) —N=, and
  (3) —($N^+$—$O^-$)=,
wherein at least two of $G^1$, $G^2$ and $G^3$ are —C($R^5$)=;

J is independently selected from:
  (1) =C($R^{6a}$)—,
  (2) —$CR^{13}R^{14}$—,
  (3) —N($R^{15}$)—, and
  (4) —C(=O)—;

Y is independently selected from:
  (1) =C($R^{6b}$)—,
  (2) —$CR^{13}R^{14}$—,
  (3) —C(=O)—,
  (4) —$SO_2$—,
  (5) =N—, and
  (6) —N($R^{6b}$)—;

$R^4$ is selected from:
  (1) hydrogen,
  (2) —$C_{1-6}$alkyl, which is unsubstituted or substituted with 1-5 substituents each independently selected from:
    (a) halo,
    (b) —$C_{3-6}$cycloalkyl,
    (c) —$CF_3$, and
    (d) —$OC_{1-6}$alkyl, which is unsubstituted or substituted with 1-5 halo,
  (3) —$C_{3-6}$cycloalkyl,
  (4) benzyl, and
  (5) phenyl;

$R^5$ is selected from:
  (1) hydrogen,
  (2) —$C_{1-6}$alkyl, which is unsubstituted or substituted with 1-7 substituents each independently selected from:
    (a) halo,
    (b) hydroxy,
    (c) —$OC_{1-6}$alkyl,
    (d) —$C_{3-6}$cycloalkyl,
    (e) phenyl,
    (f) —$CONR^{10a}R^{11a}$,
    (g) —$CO_2R^9$, and
    (h) —$NR^{10}R^{11}$,
  (3) —$C_{3-6}$cycloalkyl,
  (4) phenyl, which is unsubstituted or substituted with 1-3 substituents each independently selected from:
    (a) —$C_{1-4}$-alkyl, which is unsubstituted or substituted with 1-3 fluoro,
    (b) halo,
    (c) hydroxy, and
    (d) —O—$C_{1-6}$alkyl, which is unsubstituted or substituted with 1-6 fluoro,
  (5) halo,
  (6) hydroxy,
  (7) —$OC_{1-6}$alkyl, which is unsubstituted or substituted with 1-5 halo,
  (8) —CN,
  (9) —$CO_2R^9$,
  (10) —$NR^{10}R^{11}$,
  (11) —$SO_2R^{12}$,
  (12) —$CONR^{10a}R^{11a}$,
  (13) —$OCO_2R^9$, and
  (14) —($NR^{10a}$)$CO_2R^9$;

$R^{6a}$ and $R^{6b}$ are each independently selected from:
  (1) hydrogen;
  (2) —$C_{1-4}$alkyl, which is unsubstituted or substituted with 1-5 substituents each independently selected from:
    (a) halo,
    (b) —O—$C_{1-6}$alkyl,
    (c) —$C_{3-6}$cycloalkyl, and (d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from: —$C_{1-6}$alkyl, —O—$C_{1-6}$alkyl, halo, hydroxy, trifluoromethyl and —$OCF_3$, (3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from:
  (a) —$C_{1-4}$alkyl which is unsubstituted or substituted with 1-5 fluoro,
  (b) halo,
  (c) hydroxy,
  (d) —O—$C_{1-4}$alkyl which is unsubstituted or substituted with 1-5 fluoro,
  (e) —$C_{3-6}$cycloalkyl, and
  (f) phenyl, (4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$;

or where $R^{6a}$ and $R^{6b}$ and the atom(s) to which they are attached are joined to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —$C_{1-6}$alkyl which is unsubstituted or substituted with 1-3 substituents each independently selected from:
    (i) halo,
    (ii) hydroxy,
    (iii) —O—$C_{1-6}$alkyl,
    (iv) —$C_{3-6}$cycloalkyl,
    (v) phenyl or heterocycle, wherein heterocycle is selected from: pyridyl, pyrimidinyl, pyrazinyl, pyridazinyl, piperidinyl, piperazinyl, pyrrolidinyl, thienyl, or morpholinyl, which phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
    (vi) —$CO_2R^9$,
    (vii) —$NR^{10}R^{11}$,
    (viii) —$SO_2R^{12}$,
    (ix) —$CONR^{10a}R^{11a}$, and
    (x) —$(NR^{10a})CO_2R^9$,
  (b) phenyl or heterocycle, wherein heterocycle is selected from: pyridyl, pyrimidinyl, pyrazinyl, thienyl, pyrrolidinyl, azetidinyl, piperidinyl and morpholinyl, which phenyl or heterocycle is unsubstituted or substituted with 1-3 substituents are each independently selected from: —$C_{1-6}$alkyl which is unsubstituted or substituted with 1-6 fluoro, halo, hydroxy, —O—$C_{1-6}$alkyl, which is unsubstituted or substituted with 1-6 fluoro and —$C_{3-6}$cycloalkyl,
  (c) halo,
  (d) —$SO_2R^{12}$,
  (e) hydroxy,
  (f) —O—$C_{1-6}$alkyl, which is unsubstituted or substituted with 1-5 halo,
  (g) —CN,
  (h) —$COR^{12}$,
  (i) —$NR10R^{11}$,
  (j) —$CONR^{10a}R^{11a}$,
  (k) —$CO_2R^9$,
  (l) —$(NR^{10a})CO_2R^9$,
  (m) —$O(CO)NR^{10a}R^{11a}$,
  (n) —$(NR^9)(CO)NR^{10a}R^{11a}$, and
  (o) oxo;

$R^7$ is selected from:
  (1) hydrogen;
  (2) —$C_{1-4}$alkyl, which is unsubstituted or substituted with 1-5 substituents where the substituents are each independently selected from:
    (a) halo,
    (b) —$OC_{1-6}$alkyl,
    (c) —$C_{3-6}$cycloalkyl,
    (d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from: —CN, —$C_{1-6}$alkyl, —$OC_{1-6}$alkyl, halo, hydroxy, trifluoromethyl and —$OCF_3$,
    (e) —$COR^{12}$,
    (f) —$NR^{10}R^{11}$,
    (g) —$CONR^{10a}R^{11a}$,
    (h) —$CO_2R^9$,
    (i) —$(NR^{10a})CO_2R^9$,
    (j) —$O(CO)NR^{10a}R^{11a}$,
    (k) —$(NR^9)(CO)NR^{10a}R^{11a}$,
    (l) —CN, and
    (m) hydroxy,
  (3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from:
    (a) —$C_{1-4}$alkyl which is unsubstituted or substituted with 1-5 fluoro,
    (b) halo,
    (c) hydroxy,
    (d) —$OC_{1-6}$alkyl which is unsubstituted or substituted with 1-5 fluoro,
    (e) —$C_{3-6}$cycloalkyl, and
    (f) phenyl, and
    (g) —CN,
  (4) —$C_{3-6}$cycloalkyl, which is unsubstituted or substituted with 1-7 substituents each independently selected from: halo, hydroxy, —$OC_{1-6}$alkyl, trifluoromethyl and phenyl;

$R^9$ is independently selected from:
(1) hydrogen,
(2) —$C_{1-6}$ alkyl, which is unsubstituted or substituted with 1-6 substituents, substituents each independently selected from:
  (a) halo,
  (b) hydroxy,
  (c) —$OC_{1-6}$alkyl, which is unsubstituted or substituted with 1-5 halo,
  (d) —$C_{3-6}$cycloalkyl, and
  (e) phenyl, which is unsubstituted or substituted with 1-5 substituents each independently selected from:
    (i) —$C_{1-4}$alkyl,
    (ii) —$OC_{1-6}$alkyl,
    (iii) halo,
    (iv) trifluoromethyl, and
    (v) —$OCF_3$,
(3) —$C_{3-6}$cycloalkyl, which is unsubstituted or substituted with 1-6 substituents, substituents each independently selected from:
  (a) halo,
  (b) hydroxy,
  (c) —O—$C_{1-6}$alkyl, which is unsubstituted or substituted with 1-5 halo,
  (d) —$C_{1-6}$alkyl, which is unsubstituted or substituted with 1-5 halo, and
  (e) phenyl,
(4) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
  (a) halo,
  (b) —$C_{1-6}$alkyl, which is unsubstituted or substituted with 1-5 halo
  (c) —$OC_{1-6}$alkyl, which is unsubstituted or substituted with 1-5 halo
  (d) —$C_{3-6}$cycloalkyl,
  (e) oxo,
  (f) —CN,
  (g) hydroxy, and
  (h) phenyl;

$R^{10}$ and $R^{11}$ are each independently selected from:
(1) hydrogen,
(2) —$C_{1-6}$alkyl, which is unsubstituted or substituted with 1-6 substituents each independently selected from:
  (a) halo,
  (b) hydroxy,
  (c) —$OCF_3$,
  (d) —$C_{3-6}$cycloalkyl, and
  (e) phenyl,
(3) —$C_{4-6}$cycloalkyl,
(4) phenyl, which is unsubstituted or substituted with 1-5 substituents each independently selected from:
  (a) —$C_{1-6}$alkyl, which is unsubstituted or substituted with 1-5 halo,
  (b) —$OC_{1-6}$alkyl, which is unsubstituted or substituted with 1-5 halo,
  (c) halo,
  (d) hydroxy,
  (e) trifluoromethyl,
  (f) —$OCF_3$, and
  (g) —CN,
(5) benzyl, which is unsubstituted or substituted with 1-5 substituents each independently selected from:
  (a) —$C_{1-6}$alkyl, which is unsubstituted or substituted with 1-5 halo,
  (b) —$OC_{1-6}$alkyl, which is unsubstituted or substituted with 1-5 halo,
  (c) halo, and
  (d) trifluoromethyl,
(6) —$COR^9$, and
(7) —$SO_2R^{12}$;

$R^{10a}$ and $R^{11a}$ are each independently selected from:
(1) hydrogen,
(2) —$C_{1-6}$alkyl, which is unsubstituted or substituted with 1-6 substituents each independently selected from:
  (a) —O—$C_{1-6}$alkyl, which is unsubstituted or substituted with 1-5 halo,
  (b) halo,
  (c) hydroxy,
  (d) —$OCF_3$,
  (e) —$C_{3-6}$cycloalkyl, and
  (f) phenyl,
(3) —$C_{5-6}$cycloalkyl, which is unsubstituted or substituted with 1-5 halo,
(4) phenyl, which is unsubstituted or substituted with 1-5 substituents each independently selected from:
  (a) —$C_{1-6}$alkyl, which is unsubstituted or substituted with 1-5 halo,
  (b) —$OC_{1-6}$alkyl, which is unsubstituted or substituted with 1-5 halo,
  (c) halo,
  (d) hydroxy,
  (e) trifluoromethyl,
  (f) —$OCF_3$, and
  (g) —CN,
(5) benzyl, which is unsubstituted or substituted with 1-5 substituents each independently selected from:
  (a) —$C_{1-6}$alkyl, which is unsubstituted or substituted with 1-5 halo,
  (b) —$OC_{1-6}$alkyl, which is unsubstituted or substituted with 1-5 halo,
  (c) halo, and
  (d) trifluoromethyl,
or where $R^{10a}$ and $R^{11a}$ join to form a ring selected from azetidinyl, pyrrolidinyl, piperidinyl, azepanyl, piperazinyl and morpholinyl, which ring is unsubstituted or substituted with 1-5 substituents each independently selected from:
(1) —$C_{1-6}$alkyl, which is unsubstituted or substituted with 1-5 halo,
(2) —O—$C_{1-6}$alkyl, which is unsubstituted or substituted with 1-5 halo,
(3) halo
(4) hydroxy
(5) phenyl, which is unsubstituted or substituted with 1-5 substituents each independently selected from:
  (a) —$C_{1-4}$alkyl, which is unsubstituted or substituted with 1-3 halo,
  (b) —O—$C_{1-4}$alkyl, which is unsubstituted or substituted with 1-3 halo, and
  (c) halo,
(6) benzyl, which is unsubstituted or substituted with 1-5 substituents each independently selected from:

(a) —C$_{1-4}$alkyl, which is unsubstituted or substituted with 1-3 halo,
(b) —OC$_{1-4}$alkyl, which is unsubstituted or substituted with 1-3 halo, and
(c) halo,
(7) —COR$^9$, and
(8) —SO$_2$R$^{12}$;

R$^{12}$ is selected from:
(1) —C$_{1-6}$alkyl, which is unsubstituted or substituted with 1-6 fluoro,
(2) —C$_{3-6}$cycloalkyl,
(3) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
(a) —C$_{1-6}$alkyl, which is unsubstituted or substituted with 1-5 halo,
(b) —O—C$_{1-6}$alkyl, which is unsubstituted or substituted with 1-5 halo,
(c) halo,
(d) hydroxy,
(e) trifluoromethyl,
(f) —OCF$_3$,
(g) —CN, and
(h) benzyl, which is unsubstituted or substituted with 1-5 substituents each independently selected from:
(i) —C$_{1-6}$alkyl, which is unsubstituted or substituted with 1-5 halo,
(ii) —O—C$_{1-6}$alkyl, which is unsubstituted or substituted with 1-5 halo,
(iii) halo, and
(iv) trifluoromethyl;

R$^{13}$ and R$^{14}$ are each independently selected from:
(1) hydrogen,
(2) C$_{1-6}$alkyl, which is unsubstituted or substituted with 1-5 substituents each independently selected from:
(a) —C$_{3-6}$cycloalkyl,
(b) —OC$_{1-6}$alkyl,
(c) halo,
(d) hydroxy, and
(e) phenyl,
(3) hydroxy, and
(4) halo;

R$^{15}$ is selected from:
(1) hydrogen,
(2) —C$_{1-6}$alkyl which is unsubstituted or substituted with 1-7 substituents where the substituents are independently selected from:
(a) halo,
(b) hydroxy,
(c) —O—C$_{1-6}$alkyl,
(d) —C$_{3-6}$cycloalkyl,
(e) phenyl, and
(f) —NR$^{10}$R$^{11}$;
(3) phenyl or heterocycle, wherein heterocycle is selected from: pyridyl, pyrimidinyl, pyrazinyl, or thienyl, which is unsubstituted or substituted with 1-5 substituents where the substituents are independently selected from:
(a) —C$_{1-6}$alkyl,
(b) —O—C$_{1-6}$alkyl,
(c) halo,
(d) hydroxy, and
(e) trifluoromethyl;

m is 1; and
n is 1;
or a pharmaceutically acceptable salt thereof and individual enantiomers and diastereomers thereof.

2. A compound of claim 1 of the formula Ia:

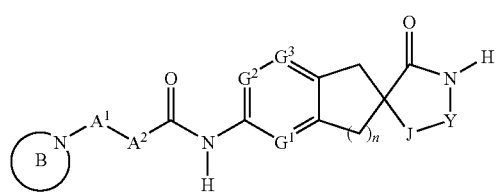

or a pharmaceutically acceptable salt thereof and individual enantiomers and diastereomers thereof.

3. A compound of claim 1 of the formula Ic:

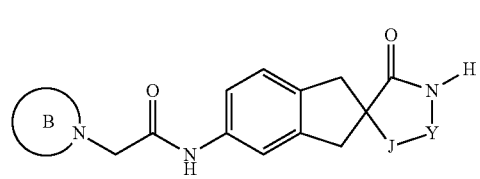

or a pharmaceutically acceptable salt thereof and individual enantiomers and diastereomers thereof.

4. A compound of claim 1 of the formula If:

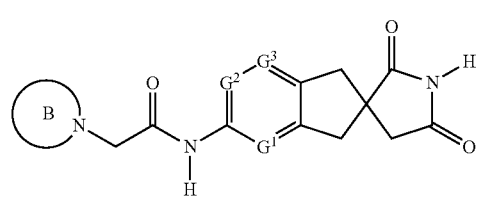

or a pharmaceutically acceptable salt thereof and individual enantiomers and diastereomers thereof.

5. A compound of claim 1 of the formula Ig:

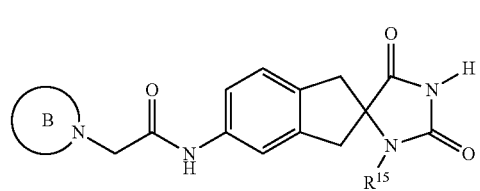

or a pharmaceutically acceptable salt thereof and individual enantiomers and diastereomers thereof.

6. A compound of claim 1 of the formula Ih:

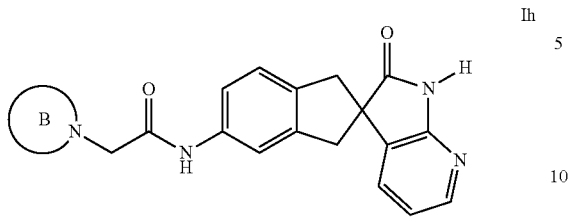

or a pharmaceutically acceptable salt thereof and individual enantiomers and diastereomers thereof.

7. A compound of claim 1 of the formula Ii:

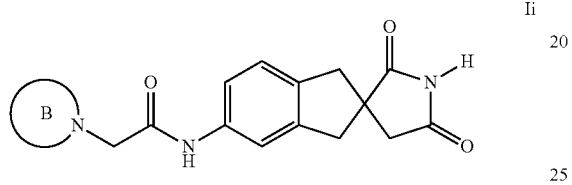

or a pharmaceutically acceptable salt thereof and individual enantiomers and diastereomers thereof.

8. The compound of claim 1 wherein B is selected from the group consisting of:

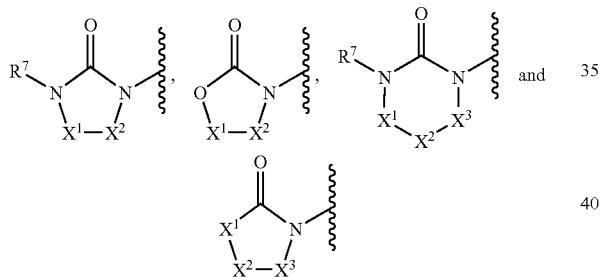

$X^1$, $X^2$, and $X^3$ are each carbon, and one of $X^1$, $X^2$, and $X^3$ present on B is spirally substituted to form a ring or ring system selected from:
indanyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, cycloheptyl, morpholinyl and tetrahydropyranyl,
which ring or ring system is unsubstituted or substituted with one or more substituents each independently selected from:
(a) —$C_{1-4}$alkyl, which is unsubstituted or substituted with 1-3 substituents where the substituents are independently selected from: halo, hydroxy, —$OC_{1-6}$alkyl, and —$C_{3-6}$cycloalkyl,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{1-6}$alkyl which is unsubstituted or substituted with 1-6 fluoro0, and —$OC_{1-6}$alkyl (which is unsubstituted or substituted with 1-6 fluoro, halo, or hydroxyl),
(c) hydroxy,
(d) —$OC_{1-6}$alkyl, which is unsubstituted or substituted with 1-5 halo,
(e) halo,
(f) —CN, and
(g) —$C_{3-6}$cycloalkyl,
and wherein the remaining members of the group $X^1$, $X^2$, and $X^3$ present on B are each independently unsubstituted or substituted with one or more substituents selected from $R^1$ and $R^2$, where:
$R^1$ and $R^2$ are each independently selected from:
(1) —$C_{1-4}$alkyl, which is unsubstituted or substituted with 1-4 substituents each independently selected from:
(a) halo,
(b) hydroxy,
(c) —O—$C_{1-6}$alkyl,
(d) —$C_{3-6}$cycloalkyl, and
(e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl,
which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
(2) —$C_{3-6}$cycloalkyl, which is unsubstituted or substituted with 1-7 substituents each independently selected from: halo, hydroxy, —$OC_{1-6}$alkyl, trifluoromethyl and phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
(a) —$C_{1-4}$alkyl, which is unsubstituted or substituted with 1-4 fluoro,
(b) halo,
(c) hydroxy,
(d) —$OC_{1-3}$alkyl, which is unsubstituted or substituted with 1-3 fluoro,
(e) —$C_{3-6}$cycloalkyl,
(4) halo,
(5) hydroxy,
(6) —$OC_{1-6}$alkyl, which is unsubstituted or substituted with 1-5 halo,
(7) —CN,
(8) —$CO_2R^9$,
(9) —$NR^{10}R^{11}$,
(10) —$SO_2R^{12}$, and
(11) —$CONR^{10a}R^{11a}$ or a pharmaceutically acceptable salt thereof and individual enantiomers and diastereomers thereof.

9. The compound of claim 1 wherein B is:

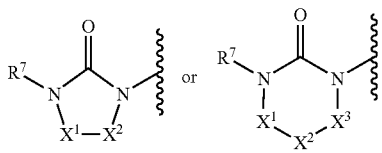

$X^1$, $X^2$, and $X^3$ are each carbon, and one of $X^1$, $X^2$, and $X^3$ present on B is spirally substituted to form a ring or ring system selected from:
  indanyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, thiochromanyl, 6,7,8,9-tetrahydro-5H-benzo[7]annulenyl and cycloheptyl,
  which ring or ring system is unsubstituted or substituted with one to five substituents each independently selected from:
    (a) —$C_{1-4}$alkyl, which is unsubstituted or substituted with 1-4 substituents each independently selected from: halo, hydroxy, —$OC_{1-6}$alkyl, and —$C_{3-6}$cycloalkyl,
    (b) hydroxy,
    (c) —$OC_{1-4}$ alkyl, which is unsubstituted or substituted with 1-4 halo,
    (d) halo, and
    (e) —CN,
and wherein the remaining members of the group $X^1$, $X^2$ and $X^3$ present on B are each independently unsubstituted or substituted with one or more substituents selected from $R^1$ and $R^2$, where:
$R^1$ and $R^2$ are each independently selected from:
  (1) —$C_{1-4}$alkyl, which is unsubstituted or substituted with 1-4 substituents each independently selected from:
    (a) halo,
    (b) hydroxy,
    (c) —O—$C_{1-6}$alkyl,
    (d) —$C_{3-6}$cycloalkyl, and
    (e) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
  (2) —$C_{3-6}$cycloalkyl, which is unsubstituted or substituted with 1-7 substituents each independently selected from: halo, hydroxy, —$OC_{1-6}$alkyl, trifluoromethyl and phenyl,
  (3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
    (a) —$C_{1-4}$alkyl, which is unsubstituted or substituted with 1-4 fluoro,
    (b) halo,
    (c) hydroxy,
    (d) —$OC_{1-3}$alkyl, which is unsubstituted or substituted with 1-3 fluoro, and
    (e) —$C_{3-6}$cycloalkyl,
  (4) halo,
  (5) hydroxy,
  (6) —$OC_{1-6}$alkyl, which is unsubstituted or substituted with 1-5 halo, and
  (7) —CN
or a pharmaceutically acceptable salt thereof and individual enantiomers and diastereomers thereof.

10. The compound of claim 1 wherein B is selected from the group consisting of:

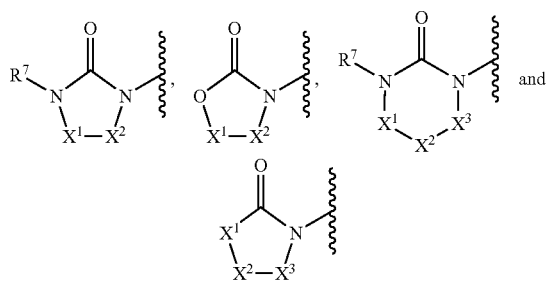

$X^1$, $X^2$ and $X^3$ are each carbon, and one of $X^1$, $X^2$ and $X^3$ present on B is —(C═O)—,
wherein another one of the members of the group $X^1$, $X^2$, $X^3$ and $X^4$ present on B is optionally spirally substituted to form a ring or ring system selected from:
  cyclopropyl, cyclobutyl, cyclopentyl, cyclohexyl, cycloheptyl, cyclooctyl, indanyl, azetidinyl, pyrrolidinyl, piperidinyl, piperazinyl, azaindanyl, 1,2,3,4-tetrahydronaphthalenyl, 5,6,7,8-tetrahydroquinolinyl, 5,6,7,8-tetrahydroisoquinolinyl, 2,3-dihydro-1-benzofuranyl, chromanyl, 3,4-dihydro-1H-isochromenyl, 2,3-dihydro-1-benzothiophenyl, thiochromanyl, 3,4-dihydro-1H-isothiochromenyl, 6,7,8,9-tetrahydro-5H-benzo[7]annulenyl, morpholinyl, tetrahydropyranyl, tetrahydrofuranyl, thiepanyl, oxepanyl and azepanyl,
  which ring or ring system is unsubstituted or substituted with one to seven substituents each independently selected from:
    (a) —$C_{1-4}$ alkyl, which is unsubstituted or substituted with 1-3 substituents where the substituents are independently selected from: halo, hydroxy, —$OC_{1-6}$alkyl, —$C_{3-6}$cycloalkyl phenyl and heterocycle, wherein said heterocycle is selected from: pyridyl, pyrimidinyl, pyrazinyl, pyridazinyl, piperidinyl, piperazinyl, pyrrolidinyl, thienyl, and morpholinyl,
    (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from: halo, hydroxy, —CN, —$C_{3-6}$cycloalkyl, —$C_{1-6}$alkyl which is unsubstituted or substituted with 1-6 fluoro, and —$OC_{1-6}$alkyl which is unsubstituted or substituted with 1-6 fluoro, halo, or hydroxyl,
    (c) hydroxy,
    (d) —$OC_{1-6}$alkyl, which is unsubstituted or substituted with 1-5 halo,
    (e) halo,
    (f) —CN, and
    (g) —$C_{3-6}$cycloalkyl, and wherein the remaining members of the group $X^1$, $X^2$ and $X^3$ present on B are each independently unsubstituted or substituted with one or more substituents selected from $R^1$ and $R^2$, where $R^1$ and $R^2$ are each independently selected from:
(1) —$C_{1-4}$alkyl, which is unsubstituted or substituted with 1-4 substituents each independently selected from:
 (a) halo,
 (b) hydroxy,
 (c) —O—$C_{1-6}$alkyl,
 (d) —$C_{3-6}$cycloalkyl, and
 (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
(2) —$C_{3-6}$cycloalkyl, which is unsubstituted or substituted with 1-7 substituents each independently selected from: halo, hydroxy, —$OC_{1-6}$alkyl, trifluoromethyl and phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
 (a) —$C_{1-4}$alkyl, which is unsubstituted or substituted with 1-4 fluoro,
 (b) halo,
 (c) hydroxy,
 (d) —$OC_{1-3}$alkyl, which is unsubstituted or substituted with 1-3 fluoro, and
 (e) —$C_{3-6}$cycloalkyl,
(4) halo,
(5) hydroxy,
(6) —$OC_{1-6}$alkyl, which is unsubstituted or substituted with 1-5 halo,
(7) —CN,
(8) —$CO_2R^9$,
(9) —$NR^{10}R^{11}$,
(10) —$SO_2R^{12}$, and
(11) —$CONR^{10a}R^{11a}$ or a pharmaceutically acceptable salt thereof and individual enantiomers and diastereomers thereof.

11. The compound of claim 1 wherein B is:

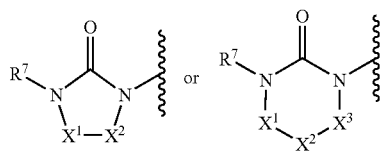

$X^1$, $X^2$ and $X^3$ are each carbon, and one of $X^1$, $X^2$ and $X^3$ present on B is —(C=O)—,
wherein another one of the members of the group $X^1$, $X^2$ and $X^3$ present on B is optionally spirally substituted to form a ring or ring system selected from:
cyclopropyl, cyclobutyl, cyclopentyl, cyclohexyl, cycloheptyl, indanyl, azetidinyl, pyrrolidinyl, piperidinyl, piperazinyl, azaindanyl, 1,2,3,4-tetrahydronaphthalenyl, 5,6,7,8-tetrahydroquinolinyl, chromanyl, thiochromanyl, 6,7,8,9-tetrahydro-5H-benzo[7]annulenyl, morpholinyl, tetrahydropyranyl, thiepanyl, oxepanyl and azepanyl
which ring or ring system is unsubstituted or substituted with one to five substituents each independently selected from:
 (a) —$C_{1-4}$alkyl, which is unsubstituted or substituted with 1-4 substituents where the substituents are independently selected from: halo, hydroxy, —$OC_{1-6}$alkyl, or —$C_{3-6}$cycloalkyl,
 (b) hydroxy,
 (c) —$OC_{1-4}$ alkyl, which is unsubstituted or substituted with 1-4 halo,
 (d) halo, and
 (e) —CN, and wherein the remaining members of the group $X^1$, $X^2$ and $X^3$ present on B are each independently unsubstituted or substituted with one or more substituents selected from $R^1$ and $R^2$, where:

$R^1$ and $R^2$ are each independently selected from:
(1) —$C_{1-4}$alkyl, which is unsubstituted or substituted with 1-4 substituents each independently selected from:
 (a) halo,
 (b) hydroxy,
 (c) —O—$C_{1-6}$alkyl,
 (d) —$C_{3-6}$cycloalkyl, and
 (e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from: —$C_{1-6}$alkyl, —$OC_{1-6}$alkyl, halo, hydroxy, trifluoromethyl, —CN, and —$OCF_3$,
(2) —$C_{3-6}$cycloalkyl, which is unsubstituted or substituted with 1-7 substituents each independently selected from: halo, hydroxy, —$OC_{1-6}$alkyl, trifluoromethyl and phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which phenyl or heterocycle is unsubstituted or substituted with 1-5 substituents each independently selected from:
 (a) —$C_{1-4}$alkyl, which is unsubstituted or substituted with 1-4 fluoro,
 (b) halo,
 (c) hydroxy,
 (d) —$OC_{1-3}$alkyl, which is unsubstituted or substituted with 1-3 fluoro, and
 (e) —$C_{3-6}$cycloalkyl,
(4) halo,
(5) hydroxy,
(6) —$OC_{1-6}$alkyl, which is unsubstituted or substituted with 1-5 halo, and
(7) —CN or a pharmaceutically acceptable salt thereof and individual enantiomers and diastereomers thereof.

12. The compound of claim 1 wherein B is 2-oxo-imidazolinyl, 2,4-dioxo-imidazolyl, or 2,4-dioxo-dihydropyrimidinyl, or a pharmaceutically acceptable salt thereof and individual enantiomers and diastereomers thereof.

13. The compound of claim 1, wherein $G^1$, $G^2$, and $G^3$ are each independently selected from: —C($R^5$)= and —N=, or a pharmaceutically acceptable salt thereof and individual enantiomers and diastereomers thereof.

14. The compound of claim 1, wherein J is =C(R$^{6a}$)—, —N(R$^{15}$)—, or —CH$_2$—, or a pharmaceutically acceptable salt thereof and individual enantiomers and diastereomers thereof.

15. The compound of claim 1, wherein Y is =C(R$^{6b}$)—, —CH$_2$— or —C(=O)—, or a pharmaceutically acceptable salt thereof and individual enantiomers and diastereomers thereof.

16. The compound of claim 1, wherein R$^5$ is hydrogen, C$_{1-6}$alkyl or halo, or a pharmaceutically acceptable salt thereof and individual enantiomers and diastereomers thereof.

17. A compound selected from:

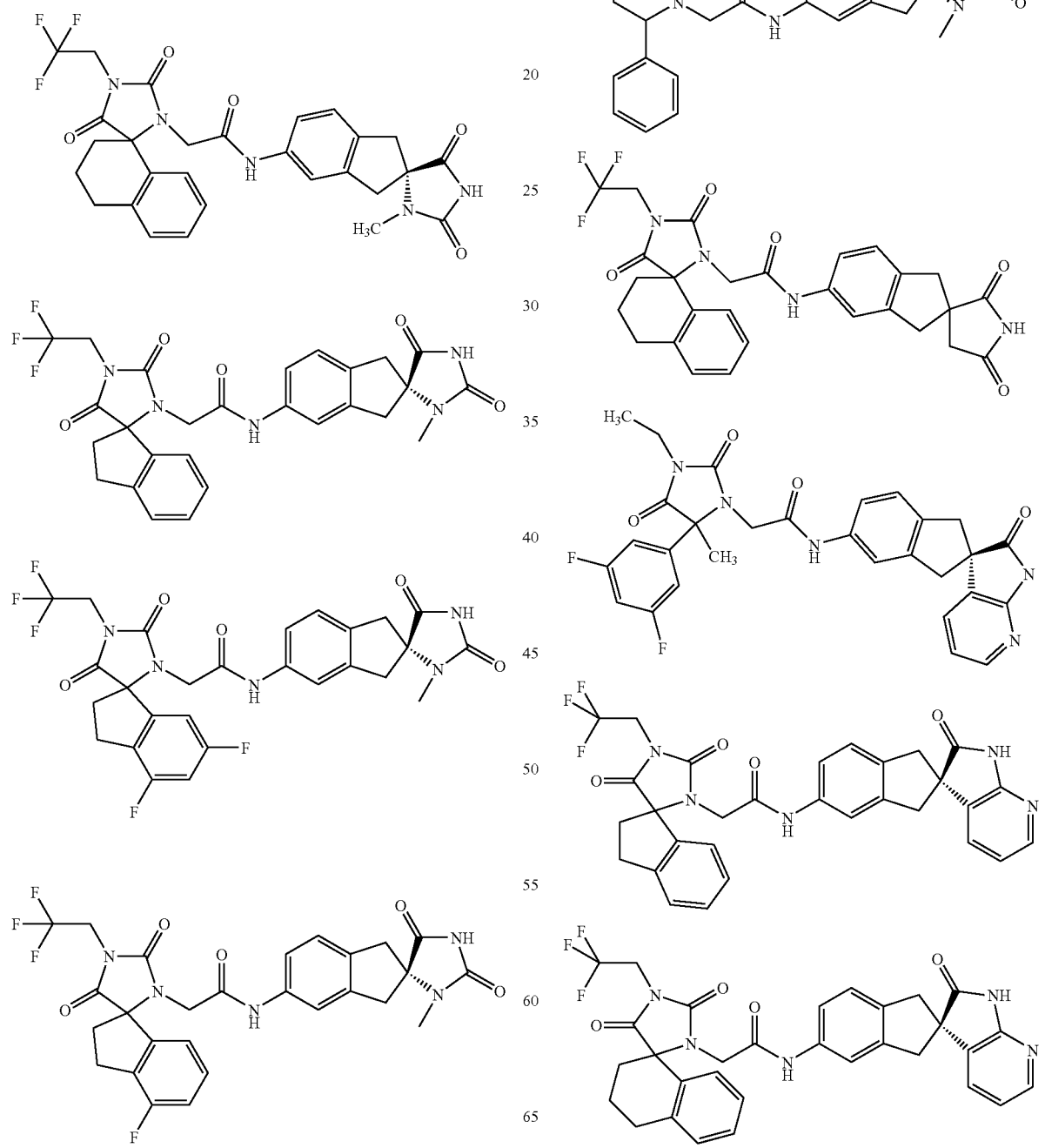

109
-continued
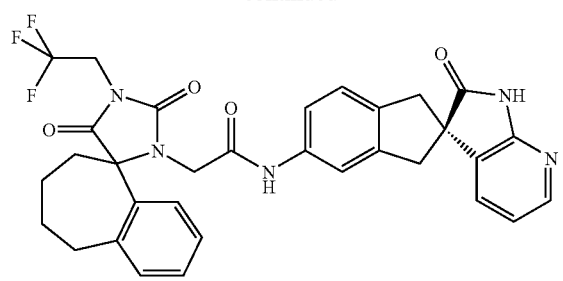
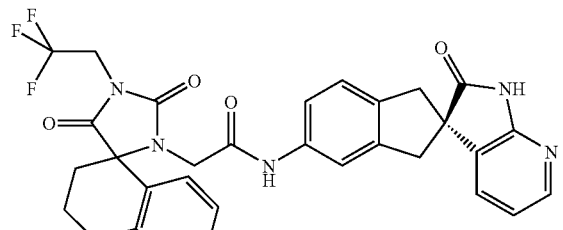
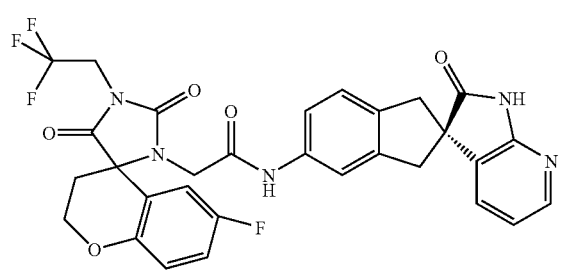
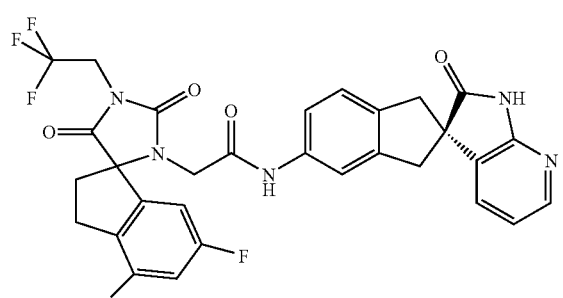
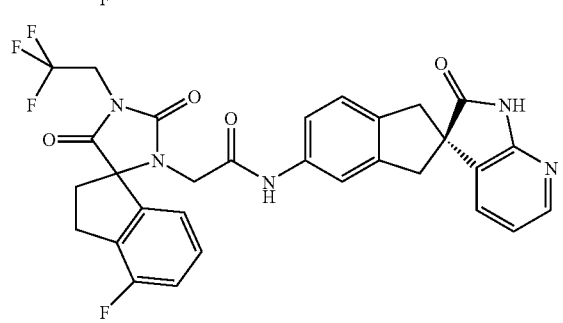
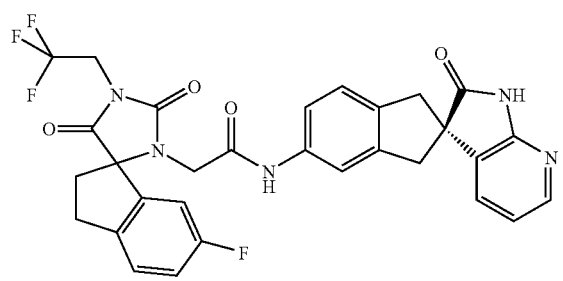
110
-continued
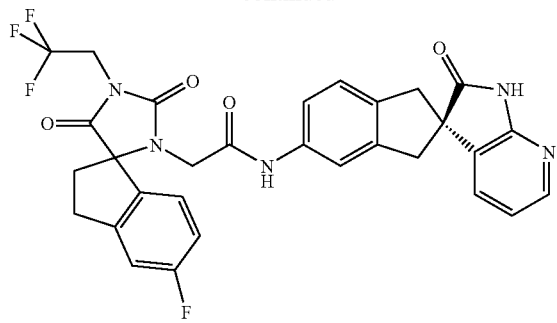
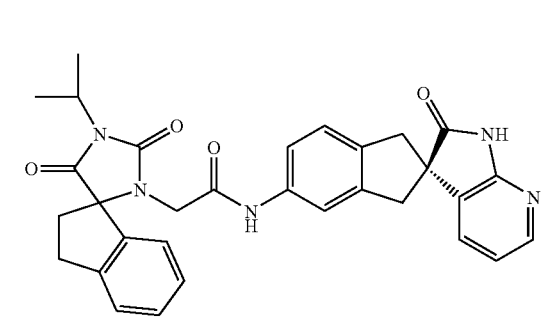
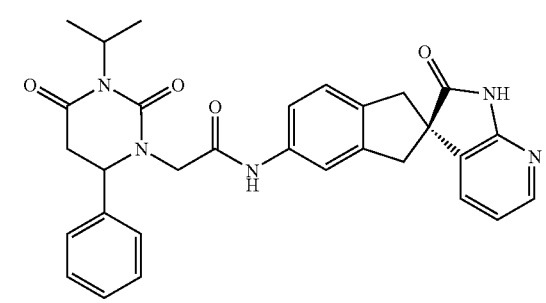
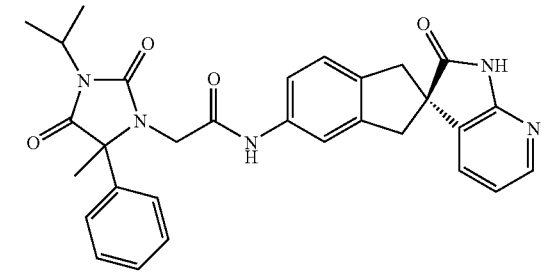
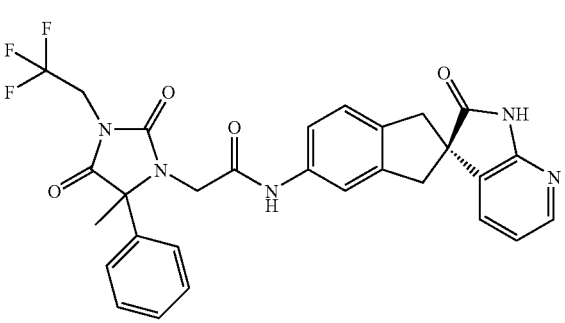

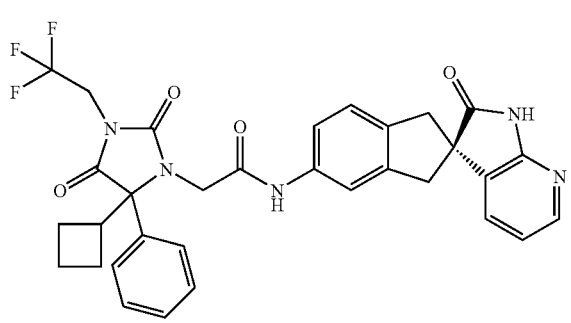
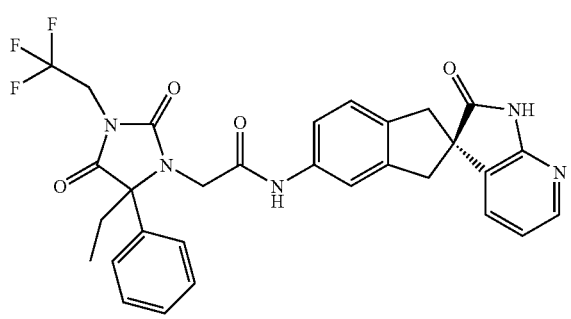
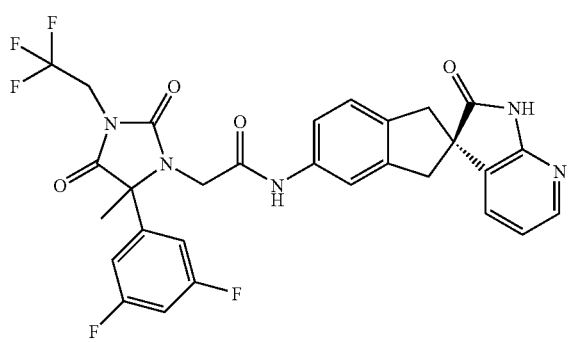
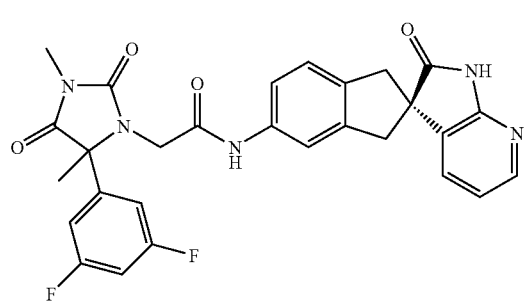
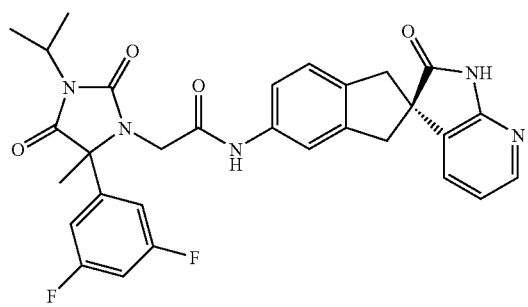
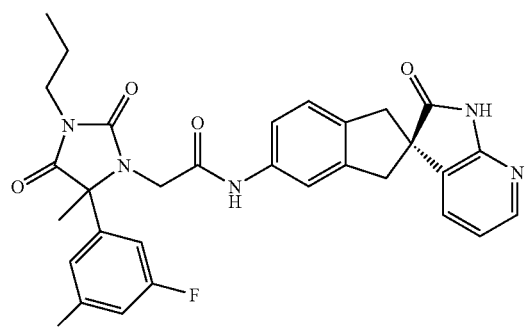
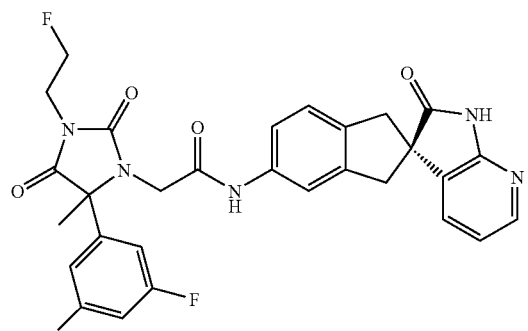
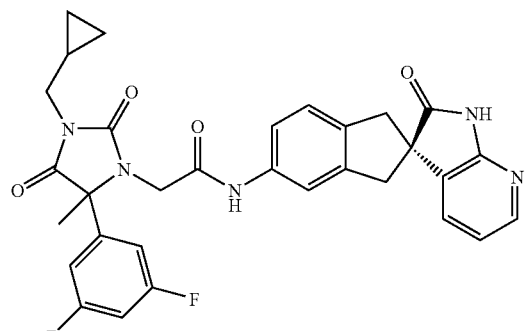
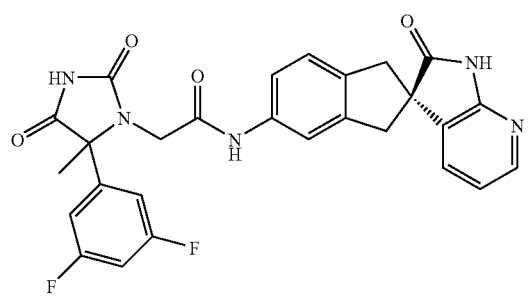
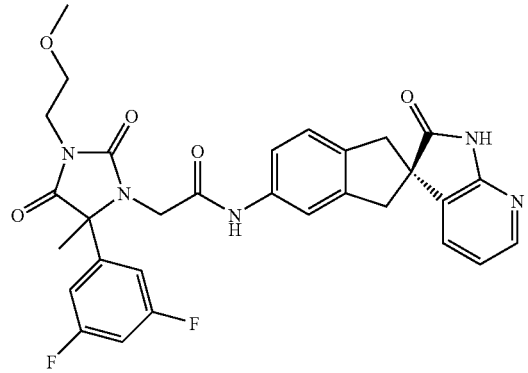

113
-continued
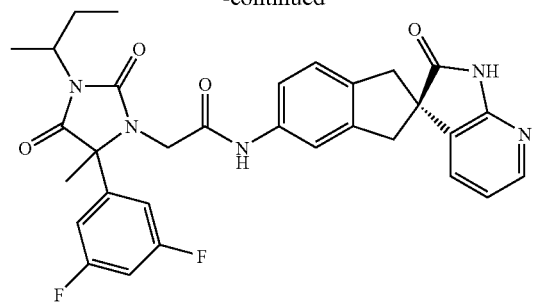
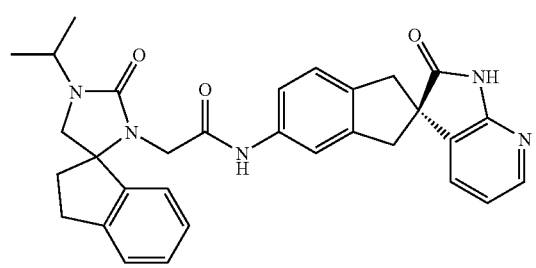
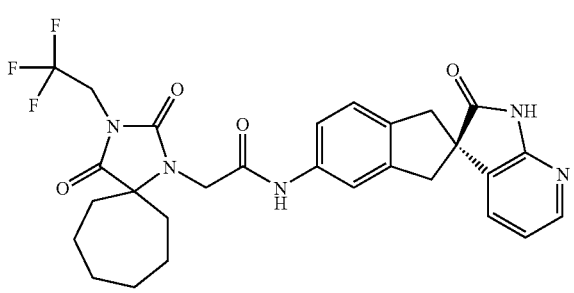
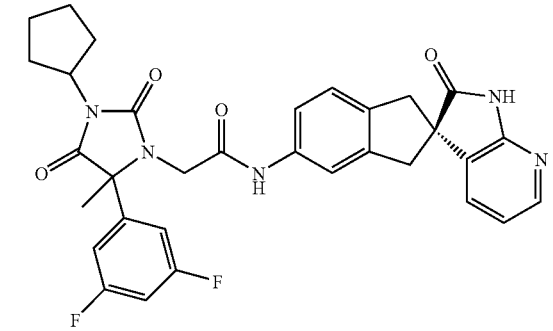
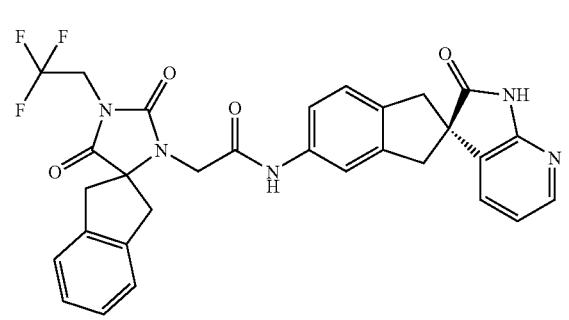
114
-continued
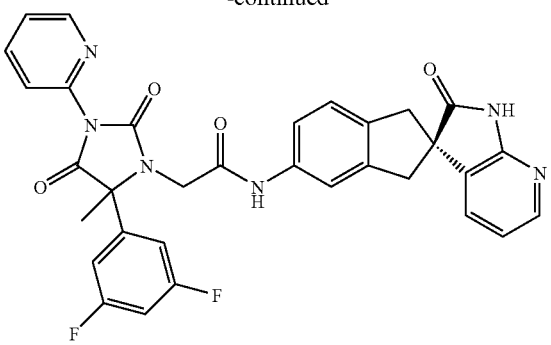
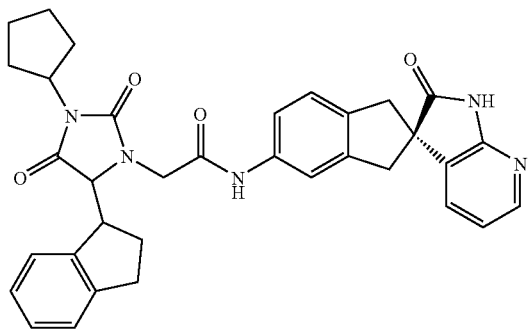
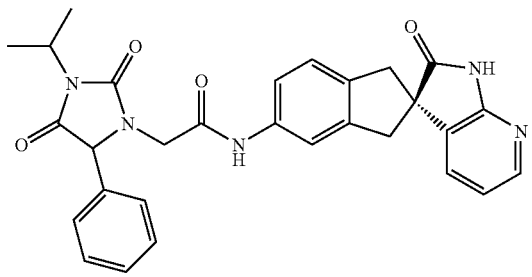
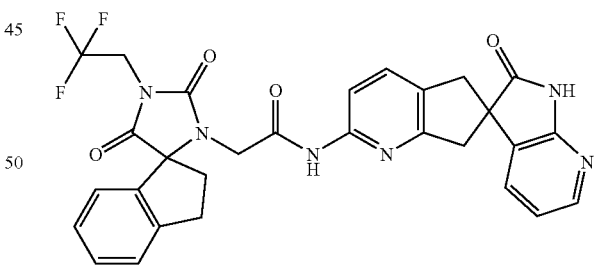
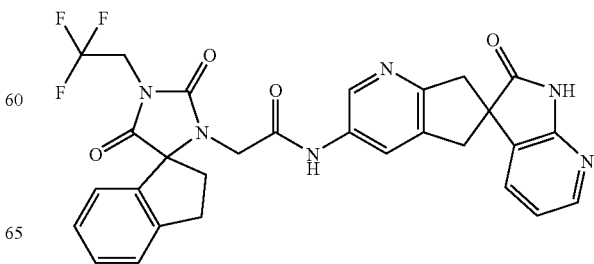

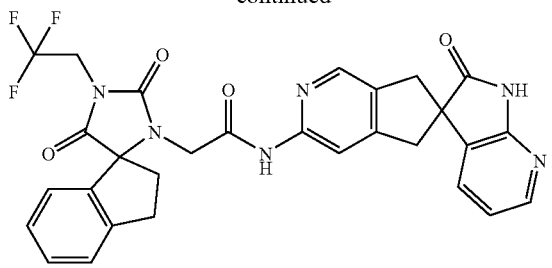

or a pharmaceutically acceptable salt thereof and individual diastereomers thereof.

18. A pharmaceutical composition which comprises an inert carrier and the compound of claim 1 or a pharmaceutically acceptable salt thereof and individual enantiomers and diastereomers thereof.

19. A method for treating migraine or cluster headache in a mammalian patient, which method comprises the step administering to a patient in need thereof a therapeutically effective amount of the compound of claim 1 or a pharmaceutically acceptable salt thereof and individual enantiomers and diastereomers thereof.

* * * * *